US011116819B2

(12) United States Patent
Scadden et al.

(10) Patent No.: US 11,116,819 B2
(45) Date of Patent: Sep. 14, 2021

(54) METHODS AND COMPOSITIONS FOR MOBILIZING STEM CELLS

(71) Applicants: President and Fellows of Harvard College, Cambridge, MA (US); The General Hospital Corporation, Boston, MA (US)

(72) Inventors: David T. Scadden, Weston, MA (US); Borja Saez, Boston, MA (US); Francesca Ferraro, Lansdale, PA (US); Jonathan Hoggatt, Cambridge, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/771,280

(22) PCT Filed: Feb. 28, 2014

(86) PCT No.: PCT/US2014/019596
§ 371 (c)(1),
(2) Date: Aug. 28, 2015

(87) PCT Pub. No.: WO2014/134539
PCT Pub. Date: Sep. 4, 2014

(65) Prior Publication Data
US 2016/0120947 A1 May 5, 2016

Related U.S. Application Data

(60) Provisional application No. 61/770,533, filed on Feb. 28, 2013, provisional application No. 61/828,568, (Continued)

(51) Int. Cl.
| | |
|---|---|
| *A61K 31/727* | (2006.01) |
| *A61K 35/28* | (2015.01) |
| *A61K 38/19* | (2006.01) |
| *A61K 38/20* | (2006.01) |
| *A61K 39/395* | (2006.01) |
| *C12N 5/0789* | (2010.01) |
| *C12N 15/113* | (2010.01) |
| *C12N 15/115* | (2010.01) |
| *A61K 45/06* | (2006.01) |
| *A61K 31/395* | (2006.01) |
| *A61K 38/17* | (2006.01) |
| *G01N 33/50* | (2006.01) |
| *C12N 5/0775* | (2010.01) |
| *A61K 36/00* | (2006.01) |
| *A61K 35/12* | (2015.01) |
| *A61K 39/00* | (2006.01) |

(52) U.S. Cl.
CPC .......... *A61K 38/195* (2013.01); *A61K 31/395* (2013.01); *A61K 31/727* (2013.01); *A61K 35/28* (2013.01); *A61K 38/1703* (2013.01); *A61K 38/193* (2013.01); *A61K 38/202* (2013.01); *A61K 39/3955* (2013.01); *A61K 45/06* (2013.01); *C12N 5/0662* (2013.01); *C12N 15/115* (2013.01); *G01N 33/5073* (2013.01); *A61K 36/00* (2013.01); *A61K 2035/124* (2013.01); *A61K 2039/505* (2013.01); *C12N 15/1136* (2013.01); *C12N 2310/11* (2013.01); *C12N 2310/16* (2013.01)

(58) Field of Classification Search
CPC ................ A61K 2300/00; A61K 35/28; A61K 2039/505; A61K 39/3955; A61K 38/00; A61K 2035/124; A61K 31/00; A61K 39/395; A61K 38/10; A61K 31/727; A61K 38/202; A61K 38/195; C07K 7/06; C07K 7/08; C07K 14/00; C07K 16/00; C12N 15/1138; C12N 15/113; C12N 15/115; C12N 2310/11; C12N 5/0662; C12N 2310/16
See application file for complete search history.

(56) References Cited

U.S. PATENT DOCUMENTS

| | | | |
|---|---|---|---|
| 6,162,427 | A | 12/2000 | Baumann et al. |
| 7,790,174 | B2 | 9/2010 | Gonthier et al. |

(Continued)

FOREIGN PATENT DOCUMENTS

| | | |
|---|---|---|
| JP | 2016-007216 A | 1/2016 |
| WO | WO 2006/020891 | 2/2006 |

(Continued)

OTHER PUBLICATIONS

Broxmeyer et al. AMD3100 and CD26 modulate mobilixation, engraftment, and survival of hematopoietic stem and progenitor cells mediated by the SDF-1/CXCL12-CXCR4 axis. Ann N.Y. Acad Sci 1106:1-19, 2007.*

(Continued)

*Primary Examiner* — Bridget E Bunner
(74) *Attorney, Agent, or Firm* — Morse, Barnes-Brown & Pendleton, P.C.; Lisa M. Warren, Esq.

(57) ABSTRACT

The present invention relates to methods and compositions for mobilizing hematopoietic stem cells and/or progenitor cells, and related methods of conditioning for engraftment of transplanted hematopoietic stem cells and/or progenitor cells, and methods of treating diseases requiring hematopoietic stem cell and/or progenitor cell transplantation.

10 Claims, 18 Drawing Sheets
(13 of 18 Drawing Sheet(s) Filed in Color)
Specification includes a Sequence Listing.

Related U.S. Application Data filed on May 29, 2013, provisional application No. 61/904,768, filed on Nov. 15, 2013.

(56) References Cited

U.S. PATENT DOCUMENTS

| | | |
|---|---|---|
| 2006/0035829 A1 | 2/2006 | Bridger et al. |
| 2007/0036747 A1 | 2/2007 | Gianni et al. |
| 2010/0178271 A1 | 7/2010 | Bridler et al. |
| 2011/0020274 A1 | 1/2011 | Zheng |
| 2011/0135651 A1 | 6/2011 | Geiger et al. |
| 2011/0166078 A1 | 7/2011 | Cabannes et al. |
| 2011/0305675 A1 | 12/2011 | Scadden et al. |
| 2012/0225028 A1 | 9/2012 | Cohen et al. |
| 2013/0028870 A1 | 1/2013 | Royal et al. |

FOREIGN PATENT DOCUMENTS

| | | |
|---|---|---|
| WO | WO 2008/019371 | 2/2008 |
| WO | WO-2011/030847 A1 | 3/2011 |
| WO | WO 2014/134539 A1 | 9/2014 |

OTHER PUBLICATIONS

Hoggatt et al. Mobilization of hematopoietic stem cells from the bone marrow niche to the blood compartment. Stem Cell Research and Therapy 2:13, 2011 (9 pages).*

Hoggatt et al. Hematopoietic stem cell mobilization with agents other than G-CSF. Stem Cell Mobilization: Methods and Protocols, Methods in Molec Biol vol. 904: 49-67, 2012.*

Pelus et al. Suprasynergistic peripheral blood stem cell mobilization in normal and fanconi anemia knockout mice by the combination of G-CSF plus the CXCR4 antagonist AMD3100 and the CXCR2 agonist GRObeta. Blood 108(11, Part 1): 909A, 2006.*

Chen et al. Mobilization as a preparative regimen for hematopoietic stem cell transplantation. Blood 107(9): 3764-3771,2006.*

Czechowicz et al. Purified Hematopoetic Stem Cell Transplantation: The next generation of blood and immune replacement. Hematol Oncol Clin N Am 25: 75-87, 2011.*

Hoggatt et al. Rapid mobilization reveals a highly engraftable hematopoietic stem cell. Cell 172: 191-204, 2018.*

King et al. Rapid mobilization of murine hematopoietic stesm cells with enhanced engraftment properties and evaluation of hematopoietic progenitor cell mobilization in rhesus monkeys by a single injection of SB-251353, a specific truncated form of the human CXC chemokine Grobeta. Blood 97: 1534-1542, 2001.*

Marquez-Curtis et al. The Ins and Outs of Hematopoietic Stem Cells: Studies to Improve Transplantation Outcomes. Stem Cell Rev and Rep 7: 590-607, 2011.*

Papayannopoulou et al. Peripheralization of hematopoietic progenitors in primates treated with anti-VLA4 integrin. Proc Natl Acad Sci USA 90: 9374-9378, 1993.*

Papayannopoulou et al. The VLA4/VCAM-1 adhesion pathway defines contrasting mechanisms of lodgement of transplanted murine hematopoietic progenitors between bone marrow and spleen. Proc Natl Acad Sci USA 92: 9647-9651, 1995.*

Saez et al. Hematopoietic stem/progenitor retention in the bone marrow depends on tissue specific heparan sulfate proteoglycans. Blood 120(21): 637, Nov. 16, 2012.*

Frenette et al. Sulfated glycans induce rapid hematopoietic progenitor cell mobilization: evidence for selectin-dependent and independent mechanisms. Blood 96: 2460-2468, 2000.*

Holley et al. Influencing hematopoietic differentiation of mouse embryonic stem cells using soluble heparin and heparain sulfate saccharides. J Biol Chem 286(8): 6241-6252, 2011.*

Kikuta et al. Mobilization of hematopoietic primitive and committed progenitor cells into blood in mice by antii-vascular adhesion molecule-1 antibody alone or in combination with granulocyte colony-stimulating factor. Exp Hematol 28: 311-317, 2000.*

Or et al. Low molecular weight heparin for the prevention of veno-occlusive disease of the liver in bone marrow transplantation patients. Transplantation 61(7): 1067-1071, 1996; text copy 12 pages.*

Papayannopoulou et al. Molecular pathways in bone marrow homing: dominant role of alpha4beta1 over beta2-integrins and selectins. Blood 98: 2403-2411,2001.*

Ramirez et al. BIO5192, a small molecule inhibitor of VLA-4, mobilizes hematopoietic stem and progenitor cells. Blood 114: 1340-1343, 2009.*

Sevilla et al. Heparin-based anticoagulation during peripheral blood stem cell collection may increase the CD34+ cell yield. Haematol 89(2): 249-251,2004.*

Zohren et al. The monoclonal anti-VLA-4 antibody natalizumab mobilizes CD34+ hematopoietic progenitor cells in humans. Blood 111:3893-3895,2008.*

Brennen, et al., "Heparan sulfate, an endogenous TLR4 agonist, promotes acute GCHD after allogenic stem cell transplantation," Blood Journal, 120(4): 2899-2907 (2012).

Di Giacomo,et al., "Heparan sulfate mimetics can efficiently mobilize long-term hematopoietic stem cells," Haematologica, 97(4): 491-499 (2012).

Ferraro,et al., "Diabetes Impairs Hematopoietic Stem Cell Mobilization by Altering Niche Function," Science Translation Medicine, 3(104): 1-13. Downloaded from http://stm.sciencemag.org/ on Feb. 3, 2016.

Fukuda, et al., "The chemokine GRO mobilizes early hematopoietic stem cells characterized by enhanced homing and engraftment," Blood, 110(3): 860-869 (2007).

Hematopoietic Stem Cell Mobilization and Apheresis: A Practical Guide for Nurses and Other Allied Health Care Professionals. European Group for Blood and Marrow Transplantation—Nurses Group (Mar. 2012).

Hoggat, et al., "Sowing the Seeds of a Fruitful Harvest: Hematopoietic Stem Cell Mobilization," Stem Cells, 31(12): 2599-2606. DOI: 10.1002/stem.1574. (Dec. 2013).

Kraushaar, et al., "Heparan Sulfate Is Required for Embryonic Stem Cells to Exit from Self-renewal," J. Biol. Chem., 285(8): 5907-5916 (2010).

Lemoli, et al. "Hematopoietic Stem Cell Mobilization," Haematoligica, 93(3): 321-324 (2008).

Pelus, "Peripheral blood stem cell mobilization: new regiments, new cells, where do we stand," Curr Opin Hematol., 15(4): 285-292, doi: 10.1097/MOH.0b013e328302f43a. (Jul. 2008).

Pelus, et al., "Chemokine-mobilized adult stem cells; defining a better hematopoietic graft," Leukemia, 22: 466-473 (2008).

Pelus, et al., "The Combination of AMD3100 Plus GROß Rapidly Mobilizes Hematopoietic Stem Cells with Enhanced Homing, Adhesion and Survival Properties," Oral and Poster Abstracts Oral Session: Experimental Transplantation—Basic Biology, Immune Function, and Engraftment Sunday, Dec. 7, 2008.

International Search Report for International Application PCT/US2014/019596, dated Aug. 8, 2014.

Albanese et al., "Glycosaminoglycan mimetics-induced mobilization of hematopoietic progenitors and stem cells into mouse peripheral blood: Structure/function insights," *Experimental Hematology*, 37:1072-1083, (2009).

Motabi et al., "Advances in stem cell mobilization," *Blood Reviews*, 26:267-268, (2012).

Pelus et al., "The CXCR4 antagonist AMD 3100 and the CXCR2 agonist GR0 beta synergistically mobilize hematopoetic stem cells (HSC) with short and long term repopulating activity," Database Biosis [Online], Database accession No. PREV200700257087, (2006).

Rankin, "Chemokines and adult bone marrow stem cells," *Immunology Letters*, 145:47-54, (2012).

Rettig et al., "Mobilization of hematopoietic stem and progenitor cells using inhibitors of CXCR4 and VLA-4," *Leukemia*, 26:34-53, (2012).

Schmit-Pokorny, "Explanding Indications for Stem Cell Transplantation," *Seminars in Oncology Nusring*, 25(2):105-114, (2009).

Supplemental European Search Report for European Application No. 14756575.8, dated Jul. 1, 2016.

(56) References Cited

OTHER PUBLICATIONS

Kang, et al., "Plerixafor (Mozobil®) Selectively Enhances Donor Hematopoietic Cell Engraftment," *Blood*, 114(22): 6 pages, (2009).

Karponi, et al., "Plerixafor+ G-CSF-Mobilized CD34+ Cells Represent an Optimal Graft Source for Thalassemia Gene Therapy," *Blood*, 126(5):616-619, (Jul. 30, 2015).

International Search Report from PCT/US2017/019778, dated Jul. 7, 2017.

Weissman, et al., "The Origins of the Identification and Isolation of Hematopoietic Stem Cells, and Their Capability to Induce Donor-Specific Transplantation Tolerance and Treat Autoimmune Diseases," *Blood*, 112(9):3543-3553, (Nov. 1, 2008).

Kikuchi et al., "The Hierarchy of Human Hematopoietic Stem Cells with Cellular and Molecular Signatures," *Hematology*, 69(4):562-567, (2014). English translation pp. 1-13.

Non-Final Office Action from U.S. Appl. No. 16/080,264, dated Feb. 16, 2021.

\* cited by examiner

METHODS AND COMPOSITIONS FOR MOBILIZING STEM CELLS

CROSS-REFERENCE TO RELATED APPLICATIONS

This application is a national stage filing under 35 U.S.C. 371 of International Application No. PCT/US2014/19596, filed Feb. 28, 2014, which claims the benefit of U.S. Provisional Application No. 61/770,533, filed Feb. 28, 2013, U.S. Provisional Application No. 61/828,568, filed May 29, 2013, and U.S. Provisional Application No. 61/904,768, filed Nov. 15, 2013. The entire teachings of the above applications are incorporated herein by reference. International Application PCT/US2014/19596 was published under PCT Article 21(2) in English.

GOVERNMENT SUPPORT

This invention was made with government support under DK050234, HL044851, HL097794, and HL009774 awarded by the National Institutes of Health. The government has certain rights in the invention.

BACKGROUND OF THE INVENTION

Hematopoietic stem cell (HSC) transplantation is a common life-saving medical procedure used to treat and cure approximately 60,000 patients per year globally. Despite its common use, there remain critical unmet needs to improve transplant efficiency and patient access, as only a fraction of patients who could benefit from an HSC transplant actually receive one. Mobilized HSCs are widely used for HSC transplantation and have improved outcomes compared to bone marrow-derived HSCs. While effective mobilization regiments exist (e.g., G-CSF), there remains a need to identify G-CSF sparing regimens or medicines that work in G-CSF recalcitrant populations.

SUMMARY OF THE INVENTION

There is a need for methods of enhancing mobilization of hematopoietic stem cells and/or progenitor cells in mobilization resistant populations (e.g., diabetes induced-mobilopathy), as well as non-cytotoxic methods of conditioning a subject for engraftment of transplanted hematopoietic stem cells and/or progenitor cells (e.g., in the absence of cytotoxic conditioning, such as chemotherapy and radiotherapy). The present invention is directed toward further solutions to address these needs, in addition to having other desirable characteristics.

Accordingly, in an aspect, the present invention provides a method of mobilizing hematopoietic stem cells and/or progenitor cells in a subject, the method comprising administering to a subject an effective amount of an agent that inhibits the level or activity of exostosin 1 (EXT1) in the subject, thereby mobilizing hematopoietic stem cells and/or progenitor cells in the subject.

In an aspect, the present invention provides a method of enhancing hematopoietic stem cell and/or progenitor cell mobilization in a subject who exhibits diabetes-induced hematopoietic stem cell and/or progenitor cell mobilopathy, the method comprising administering to the subject an effective amount of an agent that inhibits the level or activity of EXT-1, thereby enhancing hematopoietic stem cells and/or progenitor cell mobilization in the subject.

In an aspect, the present invention provides a method of conditioning a subject for engraftment of transplanted hematopoietic stem cells and/or progenitor cells in the absence of cytotoxic conditioning, the method comprising administering to a subject an amount of an agent that inhibits the level or activity of EXT1 effective to mobilize hematopoietic stem cells and/or progenitor cells in the subject, thereby conditioning the subject for engraftment of transplanted hematopoietic stem cells and/or progenitor cells in the absence of cytotoxic conditioning.

In an aspect, the present invention provides a method of treating a disease requiring transplantation of hematopoietic stem cells and/or progenitor cells in a subject in need of such treatment, the method comprising: (a) administering to a subject an amount of an agent that inhibits the level or activity of EXT1 effective to mobilize hematopoietic stem cells and/or progenitor cells in the subject, thereby conditioning the subject for engraftment of transplanted hematopoietic stem cells and/or progenitor cells in the absence of cytotoxic conditioning; and (b) transplanting hematopoietic stem cells and/or progenitor cells into the subject, wherein the transplanted hematopoietic stem cells engraft in the subject's bone marrow, thereby treating a disease requiring transplantation of hematopoietic stem cells and/or progenitor cells in the subject.

In an aspect, the present invention provides a method of mobilizing hematopoietic stem cells and/or progenitor cells in a subject, the method comprising administering to a subject an effective amount of an agent that inhibits the level or activity of heparan sulfate proteoglycans, thereby mobilizing hematopoietic stem cells and/or progenitor cells in the subject.

In an aspect, the present invention provides a method of enhancing hematopoietic stem cell and/or progenitor cell mobilization in a subject who exhibits diabetes-induced hematopoietic stem cell and/or progenitor cell mobilopathy, the method comprising administering to the subject an effective amount of an agent that inhibits the level or activity of heparan sulfate proteoglycans, thereby enhancing hematopoietic stem cells and/or progenitor cell mobilization in the subject.

In an aspect, the present invention provides a method of conditioning a subject for engraftment of transplanted hematopoietic stem cells and/or progenitor cells in the absence of cytotoxic conditioning, the method comprising administering to a subject an amount of an agent that inhibits the level or activity of heparan sulfate proteoglycans effective to mobilize hematopoietic stem cells and/or progenitor cells in the subject, thereby conditioning the subject for engraftment of transplanted peripheral blood stem cells and/or progenitor cells in the absence of cytotoxic conditioning.

In an aspect, the present invention provides a method of treating a disease requiring transplantation of hematopoietic stem cells and/or progenitor cells in a subject in need of such treatment, the method comprising: (a) administering to a subject an amount of an agent that inhibits the level or activity of heparan sulfate proteoglycans effective to mobilize hematopoietic stem cells and/or progenitor cells in the subject, thereby conditioning the subject for engraftment of transplanted hematopoietic stem cells and/or progenitor cells in the absence of cytotoxic conditioning; and (b) transplanting hematopoietic stem cells and/or progenitor cells into the subject, wherein the transplanted hematopoietic stem cells engraft in the subject's bone marrow, thereby treating a disease requiring transplantation of hematopoietic stem cells and/or progenitor cells in the subject.

The present invention contemplates inhibiting the level or activity of EXT1 or its products (heparan sulfates) in any cell, tissue, organ, or individual. In some embodiments, the agent inhibits the level or activity of heparan sulfate proteoglycans expressed in mesenchymal cells. In some embodiments, the agent inhibits the level or activity of heparan sulfate proteoglycans expressed in bone marrow mesenchymal cells. In some embodiments, the agent inhibits the level or activity of heparan sulfate proteoglycans expressed in Mx1+ skeletal stem cells and/or progenitor cells.

In some embodiments, the agent is selected from the group consisting of small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof. In some embodiments, the agent is selected from the group consisting of heparin sulfate or an analog or derivative thereof, protamine sulfate or an analog or derivative thereof, an agent that decreases the level or activity of EXT-1, and an agent that decreases the level or activity of VCAM-1.

In some embodiments, the stem cells and/or progenitor cells mobilized in the subject comprise $CD34^+$ peripheral blood stem cells and/or progenitor cells.

In some embodiments, the method includes harvesting the stem cells and/or progenitor cells mobilized in the subject.

In some embodiments, the method includes transplanting the harvested stem cells and/or progenitor cells into a subject in need of such transplantation.

In some embodiments, the stem cells and/or progenitor cells mobilized in the subject are harvested for autologous transplantation into the subject. In some embodiments, the stem cells and/or progenitor cells mobilized in the subject are harvested for allogeneic transplantation into a recipient subject. In some embodiments, the stem cells and/or progenitor cells are mobilized in the subject to condition the subject for subsequent engraftment of transplanted hematopoietic stem cells and/or progenitor cells.

In some embodiments, the subject is conditioned for subsequent engraftment of transplanted hematopoietic stem cells and/or progenitor cells in the absence of cytotoxic conditioning. In some embodiments, the subject is conditioned for engraftment without chemotherapy. In some embodiments, the subject is conditioned for engraftment without radiation.

In some embodiments, the method includes selecting a subject who exhibits poor mobilization in response to a conventional mobilization regimen. In some embodiments, the subject exhibits poor mobilization in response to granulocyte colony-stimulating factor (G-CSF).

In some embodiments, the method includes administering to the subject a cytokine selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof.

In some embodiments, the method includes administering to the subject a combination of G-CSF or a glycosylated or peglyated form thereof and heparin.

In some embodiments, the method comprises selecting a subject diagnosed with, suspected of having, or at risk of developing a hematological malignancy. In some embodiments, the disease requiring transplantation of hematopoietic stem cells and/or progenitor cells comprises a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the method includes selecting a subject diagnosed with, suspected of having, or at risk of developing a non-malignant disease. In some embodiments, the disease requiring transplantation of hematopoietic stem cells and/or progenitor cells comprises a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In some embodiments, the methods include selecting a subject diagnosed with, suspected of having, or at risk of developing diabetes. In some embodiments, the subject exhibits stem cell and/or progenitor cell mobilopathy. In some embodiments, the methods include selecting a subject who exhibits diabetes-induced hematopoietic stem cell and/or progenitor cell mobilopathy.

In an aspect, the present invention provides a method of mobilizing hematopoietic stem cells and/or progenitor cells in a subject, comprising administering to a subject a combination of two or more mobilization agents comprising (i) at least one heparan sulfate inhibitor and (ii) at least one of a CXCR2 agonist and a CXCR4 antagonist, in amounts effective to mobilize hematopoietic stem cells and/or progenitor cells into the subject's peripheral blood.

In some embodiments, the method of mobilizing hematopoietic stem cells and/or progenitor cells in a subject includes harvesting the peripheral blood stem cells mobilized in the subject. In some embodiments, the method of mobilizing hematopoietic stem cells and/or progenitor cells in a subject includes harvesting the peripheral blood stem cells via apheresis. In some embodiments, the hematopoietic stem cell mobilization and apheresis are performed on the same day. In some embodiments, a single session of apheresis collects enough peripheral blood stem cells for a cell dose of between about about $2\times10^6$/kg and $10\times10^6$/kg of the recipient's body weight. In some embodiments, the method of mobilizing hematopoietic stem cells and/or progenitor cells in a subject includes conditioning a subject in need of a stem cell transplantation for engraftment of transplanted stem cells by administering to the subject a combination of two or more mobilization agents comprising (i) at least one heparan sulfate inhibitor and (ii) at least one of a CXCR2 agonist and a CXCR4 antagonist, in amounts effective to deplete hematopoietic stem cells in the conditioned subject's stem cell niche for subsequent engraftment in the conditioned subject's stem cell niche of transplanted stem cells. In some embodiments, the method of mobilizing hematopoietic stem cells and/or progenitor cells in a subject includes transplanting the harvested peripheral blood stem cells into a subject in need of such transplantation.

In an aspect, the present invention provides a method of harvesting peripheral blood stem cells for transplantation in a subject in need of such cells, comprising: (a) administering to a peripheral blood stem cell donor a combination of two or more mobilization agents comprising (i) at least one heparan sulfate inhibitor and (ii) at least one of a CXCR2 agonist and a CXCR4 antagonist, in amounts effective to mobilize circulating peripheral blood stem cells in the donor; and (b) harvesting the mobilized circulating peripheral blood stem cells from the donor for transplantation in a subject.

In an aspect, the present invention provides a method of conditioning a subject for engraftment of transplanted peripheral blood stem cells, comprising: (a) administering to a subject a combination of two or more mobilization agents comprising (i) at least one heparan sulfate inhibitor and (ii) at least one of a CXCR2 agonist or a CXCR4 antagonist, in amounts effective to deplete hematopoietic stem cells from the subject's stem cell niche for subsequent engraftment in the subject's stem cell niche of transplanted peripheral blood stem cells, thereby conditioning the subject for engraftment of transplanted peripheral blood stem cells.

In an aspect, the present invention provides a method of treating a subject in need of a peripheral blood stem cell transplantation, comprising (a) administering to a subject a combination of two or more mobilization agents comprising (i) at least one heparan sulfate inhibitor and (ii) at least one of a CXCR2 agonist or a CXCR4 antagonist, in amounts effective to condition the subject's stem cell niche for subsequent engraftment of transplanted peripheral blood stem cells; and (b) transplanting peripheral blood stem cells into the subject.

In some embodiments, the combination of two or more mobilization agents is formulated as a composition. In some embodiments, the composition is formulated for subcutaneous administration.

In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1. In some embodiments, the at least one CXCR2 agonist is selected from the group consisting of (i) Gro-beta or an analog or derivative thereof and (ii) Gro-betaΔ4 or an analog or derivative thereof. In some embodiments, the at least one CXCR4 antagonist is Plerixafor or an analog or derivative thereof.

In some embodiments, administration of the combination of two or more mobilization agents mobilizes an amount of circulating peripheral blood stem cells in the subject to harvest a cell dose of between about $1\times10^6$/kg body weight and $10\times10^6$/kg body weight in a single apheresis session. In some embodiments, administration of the combination of two or more mobilization agents mobilizes an amount of circulating peripheral blood stem cells in the subject to harvest a cell dose of between about $2\times10^6$/kg body weight and $8\times10^6$/kg body weight in a single apheresis session. In some embodiments, administration of the combination of two or more mobilization agents mobilizes an amount of circulating peripheral blood stem cells in the subject to harvest a cell dose of between about $3\times10^6$/kg body weight and $6\times10^6$/kg body weight in a single apheresis session.

In some embodiments, the subject is conditioned for engraftment without chemotherapy. In some embodiments, the subject is conditioned for engraftment without radiation. In some embodiments, the subject is conditioned for engraftment without attenuating stromal cells. In some embodiments, the subject is conditioned for engraftment without administering G-CSF to the subject.

In some embodiments, a method of the invention includes administering to the subject a cytokine selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof. In some embodiments, a method of the invention includes administering to the subject at least one chemotherapeutic agent.

In some embodiments, the mobilized hematopoietic stem cells comprise $CD34^+$ peripheral blood stem cells.

It should be appreciated that the methods described herein can be used in connection with autologous stem cell transplantations or allogeneic stem cell transplantations. In the context of autologous stem cell transplantations, "donor" and "subject" refer to the same individual. In the context of allogeneic stem cell transplantations, "donor" and "subject" refer to different individuals. However, in some contexts which should be apparent to those skilled in the art, "subject" is used interchangeably with "donor" to refer to an individual who receives a hematopoietic stem cell mobilization agent or combination of hematopoietic stem cell mobilization agents described herein for subsequent harvesting and transplantation into a subject in need of such hematopoietic stem cells.

In some embodiments, the hematopoietic stem cells are mobilized in the subject for autologous transplantation. In some embodiments, the hematopoietic stem cells are mobilized in the subject for allogenic transplantation. In some embodiments, the subject is selected for exhibiting poor mobilization in response to administration of G-CSF alone. In some embodiments, the subject is selected for exhibiting poor mobilization in response to administration of Plerixafor alone. In some embodiments, the subject is selected for exhibiting poor mobilization in response to administration of a combination of G-CSF and Plerixafor.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In an aspect, the present invention provides a method of treating a disease requiring peripheral blood stem cell transplantation in a subject in need of such treatment, comprising: (a) administering to a peripheral blood stem cell donor a combination of two or more mobilization agents comprising i) at least one heparan sulfate inhibitor and at least one of a CXCR2 agonist and a CXCR4 antagonist, in amounts effective to mobilize circulating peripheral blood stem cells in the donor; and (b) transplanting the mobilized circulating peripheral blood stem cells from the donor into a subject in need of a peripheral blood stem cell transplantation.

In some embodiments, the combination of two or more mobilization agents are formulated as a composition. In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1. In some embodiments, the at least one CXCR2 agonist is selected from the group consisting of Gro-beta or an analog or derivative thereof and Gro-betaΔ4 or an analog or derivative thereof. In some embodiments, the at least one CXCR4 antagonist is Plerixafor or an analog or derivative thereof. In some embodiments, the method includes administering to the subject a cytokine selected from the group consisting of recombinant granulocyte colony-stimulating factor (G-CSF), granulocyte-macrophage colony-stimulating factor (GM-CSF), interleukin-3 (IL-3) and glycosylated or pegylated forms thereof.

In some embodiments, the mobilized hematopoietic stem cells comprise $CD34^+$ peripheral blood stem cells. In some embodiments, the method includes harvesting the $CD34^+$ peripheral blood stem cells from the donor prior to transplantation into the subject. In some embodiments, harvesting the mobilized hematopoietic stem cells comprises apheresis. In some embodiments, administration of the combination of two or more mobilization agents to the donor is performed on the same day as the apheresis procedure. In some embodiments, the apheresis procedure is performed within an hour of administration of the combination of two or more mobilization agents.

In some embodiments, the method includes conditioning the subject in need of the peripheral blood stem cell transplantation for engraftment of transplanted peripheral blood stem cells prior to transplantation of the peripheral blood stem cells. In some embodiments, conditioning comprises administering to the subject a combination of two or more mobilization agents comprising i) at least one heparan sulfate inhibitor and ii) at least one of a CXCR2 agonist and at least one CXCR4 antagonist, in amounts effective to deplete hematopoietic stem cells in the conditioned subject's stem cell niche for subsequent engraftment in the conditioned subject's stem cell niche of transplanted peripheral blood stem cells.

In some embodiments, the subject is not administered a chemotherapy or radiotherapy treatment prior to transplantation of the peripheral blood stem cells. In some embodiments, the donor and the subject are the same individual. In some embodiments, the donor and the subject are different individuals. In some embodiments, the donor and/or the subject is selected for exhibiting poor mobilization in response to administration of G-CSF alone. In some embodiments, the donor and/or the subject is selected for exhibiting poor mobilization in response to administration of Plerixafor alone. In some embodiments, the donor and/or the subject is selected for exhibiting poor mobilization in response to administration of a combination of G-CSF and Plerixafor.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia. In some embodiments, the method includes administering to the subject a therapeutically effective amount of a conventional treatment for the hematological malignancy.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome. In some embodiments, the method includes administering to the subject a therapeutically effective amount of a conventional treatment for the non-malignant disease.

In an aspect, the present invention provides a method of selecting a subject who would benefit from hematopoietic stem cell remobilization using a combination of two or more mobilization agents comprising (i) at least one heparan sulfate inhibitor and at least one of a CXCR2 agonist and a CXCR4 antagonist, comprising identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using a combination of two or more mobilization agents comprising (i) at least one heparan sulfate inhibitor and (ii) at least one of a CXCR2 agonist, and a CXCR4 antagonist.

In some embodiments, the method includes administering to the subject the combination of two or more mobilization agents to remobilize hematopoietic stem cells in the subject. In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1, the at least one CXCR2 agonist is selected from the group consisting of Gro-beta or an analog or derivative thereof and Gro-betaΔ4 or an analog or derivative thereof, and the at least one CXCR4 antagonist is Plerixafor or an analog or derivative thereof.

In an aspect, the present invention provides, a method of conditioning a subject for engraftment of transplanted peripheral blood stem cells, comprising administering to a subject a combination of two or more mobilization comprising i) at least one heparan sulfate inhibitor and ii) at least one of a CXCR2 agonist and a CXCR4 antagonist, in an amounts effective to deplete hematopoietic stem cells from the subject's stem cell niche for subsequent engraftment in the subject's stem cell niche of transplanted stem cells, thereby conditioning the subject for engraftment of transplanted stem cells. In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1, the at least one CXCR2 agonist is selected from the group consisting of Gro-beta or an analog or derivative thereof and Gro-betaΔ4 or an analog or derivative thereof, and the at least one CXCR4 antagonist is Plerixafor or an analog or derivative thereof.

In an aspect, the present invention provides a composition comprising two or more mobilization agents comprising i) at least one heparan sulfate inhibitor, and ii) at least one of a CXCR2 agonist and a CXCR4 antagonist. In some embodiments, the composition includes a cytokine selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof. In some embodiments, the composition includes at least one chemotherapeutic agent. In some embodiments, the composition includes at least one conventional treatment for a hematological malignancy selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia. In some embodiments, the composition includes at least one conventional treatment for a non-hematological malignancy selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome. In some embodiments, the composition is useful for mobilizing hematopoietic stem cells into peripheral blood. In some embodiments, the composition is useful for remobilizing hematopoietic stem cells in subjects who exhibit poor mobilization in response to administration of one or more of G-CSF alone, and Plerixafor. In some embodiments, the composition is useful for conditioning a subject for engraftment of transplanted stem cells. In some embodiments, the composition is useful for rapid mobilization of hematopoietic stem cells from the stem cell niche into peripheral blood. In some embodiments, the composition mobilizes hematopoietic stem cells from the stem cell niche into peripheral blood in as little as 15 minutes. In some embodiments, the combination of two or more mobilization agents are formulated for subcutaneous administration. In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1. In some embodiments, the at least one CXCR2 agonist is selected from the group consisting of Gro-beta or an analog or derivative thereof, and Gro-betaΔ4 or an analog or derivative thereof. In some embodiments, the at least one CXCR4 antagonist is Plerixafor or an analog or derivative thereof.

In an aspect, the present invention provides a method of identifying a hematopoietic stem cell mobilizing agent comprising: (a) providing a test agent; and (b) assessing the ability of the test agent to emulate the hematopoietic stem cell mobilizing effect of a combination of two or more mobilization agents comprising (i) at least one heparan sulfate inhibitor and (ii) at least one of a CXCR2 agonist, and a CXCR4 antagonist. In some embodiments, the at least one heparan sulfate inhibitor is selected from the group consisting of heparin sulfate or an analog or derivative thereof and protamine sulfate or an analog or derivative thereof, the at least one CXCR2 agonist is selected from the group consisting of Gro-beta or an analog or derivative thereof and Gro-betaΔ4 or an analog or derivative thereof, and the at least one CXCR4 antagonist is Plerixafor or an analog or derivative thereof.

In an aspect, the present invention provides a kit comprising: (a) a combination of two or more mobilization agents comprising (i) at least one heparan sulfate inhibitor, and (ii) at least one of a CXCR2 agonist and a CXCR4 antagonist; and (b) instructions for the administrating the combination of two or more mobilization agents to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted stem cells; and (iv) treating a disease requiring stem cell transplantation in the subject. In some embodiments, the at least one heparan sulfate inhibitor is selected from the group consisting of heparin sulfate or an analog or derivative thereof and protamine sulfate or an analog or derivative thereof, the at least one CXCR2 agonist is selected from the group consisting of Gro-beta or an analog or derivative thereof and Gro-betaΔ4 or an analog or derivative thereof, and the at least one CXCR4 antagonist is Plerixafor or an analog or derivative thereof. In some embodiments, the kit includes one or more medical devices for transplanting the mobilized peripheral blood stem cells into the subject.

In one aspect, the disclosure provides a method of mobilizing hematopoietic stem cells and/or progenitor cells in a subject, comprising administering to a subject a combination of two or more mobilization agents selected from the group consisting of at least one heparan sulfate inhibitor, at least one CXCR2 agonist, and at least one CXCR4 antagonist in amounts effective to mobilize hematopoietic stem cells and/or progenitor cells into the subject's peripheral blood.

In some embodiments, a method of mobilizing stem and/or progenitor cells (e.g., hematopoietic) further comprises administering to the subject a cytokine selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof.

In some embodiments, the mobilized hematopoietic stem cells comprise CD34+ peripheral blood stem cells.

In some embodiments, the method further comprises harvesting the CD34+ peripheral blood stem cells.

In some embodiments, harvesting the mobilized stem cells comprises apheresis, e.g., apheresis performed on the same day that the combination of two or more mobilization agents selected from the group consisting of at least one heparan sulfate inhibitor, at least one CXCR2 agonist and the CXCR4 antagonist are administered to the subject.

In some embodiments, administration of the combination of two or more mobilization agents selected from the group consisting of at least one heparan sulfate inhibitor, at least one CXCR2 agonist and CXCR4 antagonist mobilizes an amount of circulating peripheral blood stem cells in the subject sufficient to harvest a cell dose of between about $1 \times 10^6$/kg body weight and $10 \times 10^6$/kg body weight in a single apheresis session. In some embodiments, administration of the combination of two or more mobilization agents selected from the group consisting of at least one heparan sulfate inhibitor, at least one CXCR2 agonist and at least one CXCR4 antagonist mobilizes an amount of circulating peripheral blood stem cells in the subject sufficient to harvest a cell dose of between about $2 \times 10^6$/kg body weight and $8 \times 10^6$/kg body weight in a single apheresis session. In some embodiments, administration of the combination of two or more mobilization agents selected from the group consisting of the at least one heparan sulfate inhibitor, the at least one CXCR2 agonist and the at least one CXCR4 antagonist mobilizes an amount of circulating peripheral blood stem cells in the subject sufficient to harvest a cell dose of between about $3 \times 10^6$/kg body weight and $6 \times 10^6$/kg body weight in a single apheresis session.

In some embodiments, the method further comprises conditioning a subject in need of a stem cell transplantation for engraftment of transplanted stem cells. In some embodiments, conditioning the subject comprises administering to the subject a combination of two or more mobilization agents selected from the group consisting of at least one heparan sulfate inhibitor, at least one CXCR2 agonist and at least one CXCR4 antagonist in amounts effective to deplete hematopoietic stem cells in the conditioned subject's stem cell niche for subsequent engraftment in the conditioned subject's stem cell niche of transplanted stem cells. In some embodiments, conditioning the subject comprises administering to the subject a composition comprising a combination of two or more mobilization agents selected from the group consisting of at least one heparan sulfate inhibitor, at least one CXCR2 agonist and at least one CXCR4 antagonist in amounts effective to deplete stem cells in the conditioned subject's stem cell niche for subsequent engraftment in the conditioned subject's stem cell niche of transplanted stem cells. In some embodiments, the method further comprises administering to the subject at least one chemotherapeutic agent. In some embodiments, the subject is conditioned for engraftment without chemotherapy. In some embodiments, the subject is conditioned for engraftment without radiation. In some embodiments, the subject is conditioned for engraftment without attenuating stromal cells. In some embodiments, the subject is conditioned for engraftment without administering G-CSF to the subject.

In some embodiments, the method further comprises transplanting the harvested peripheral blood stem cells into a subject in need of such transplantation.

In some embodiments, the hematopoietic stem cells are mobilized in the subject for autologous transplantation. In some embodiments, the hematopoietic stem cells are mobilized in the subject for allogenic transplantation.

In some embodiments, the subject is selected for exhibiting poor mobilization in response to administration of one or more agents, e.g., G-CSF alone. In some embodiments, the subject is selected for exhibiting poor mobilization in response to administration of Plerixafor alone. In some embodiments, the subject is selected for exhibiting poor mobilization in response to administration of a combination of G-CSF and Plerixafor.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In another aspect, the disclosure provides a method of harvesting peripheral blood stem cells for transplantation in a subject in need of such cells, comprising: (a) administering to a peripheral blood stem cell donor a combination of two or more mobilization agents selected from the group consisting of at least one heparan sulfate inhibitor, at least one CXCR2 agonist and at least one CXCR4 antagonist in amounts effective to mobilize circulating peripheral blood stem cells in the donor; and (b) harvesting the mobilized circulating peripheral blood stem cells from the donor for transplantation in a subject.

In some embodiments, the circulating peripheral blood stem cells comprise CD34+ peripheral blood stem cells.

In some embodiments, harvesting the peripheral blood stem cells comprises apheresis and the hematopoietic stem cell mobilization and apheresis are performed on the same day. In some embodiments, a single session of apheresis collects enough CD34+ peripheral blood stem cells for a cell dose of between about $2 \times 10^6$/kg and $10 \times 10^6$/kg of the recipient's body weight.

In some embodiments, a method of harvesting peripheral blood stem cells for transplantation in a subject in need of such cells further comprises conditioning a subject in need of a peripheral blood stem cell transplantation for engraftment of transplanted peripheral blood stem cells by administering to the subject to be conditioned a combination of two or more mobilization agents selected from the group consisting of at least one heparan sulfate inhibitor, at least one CXCR2 agonist and at least one CXCR4 antagonist in amounts effective to deplete hematopoietic stem cells in the conditioned subject's stem cell niche for subsequent engraftment in the conditioned subject's stem cell niche of transplanted peripheral blood stem cells. In some embodiments, the subject is conditioned for engraftment without chemotherapy or radiation therapy.

In some embodiments, a method of harvesting peripheral blood stem cells for transplantation in a subject in need of such cells further comprises transplanting the harvested peripheral blood stem cells into a subject in need of such transplantation.

In some embodiments, the hematopoietic stem cells are mobilized in the subject for autologous transplantation. In some embodiments, the hematopoietic stem cells are mobilized in the subject for allogenic transplantation.

In some embodiments, the subject is selected for exhibiting poor mobilization in response to administration of one or more agents, e.g., G-CSF alone. In some embodiments, the subject is selected for exhibiting poor mobilization in response to administration of Plerixafor alone. In some embodiments, the subject is selected for exhibiting poor mobilization in response to administration of a combination of G-CSF and Plerixafor.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In some aspects, the disclosure provides a method of conditioning a subject for engraftment of transplanted peripheral blood stem cells, comprising: (a) administering to a subject a combination of two or more mobilization agents selected from the group consisting of at least one heparan sulfate inhibitor, at least one CXCR2 agonist, and at least one CXCR4 antagonist in amounts effective to deplete hematopoietic stem cells from the subject's stem cell niche for subsequent engraftment in the subject's stem cell niche of transplanted peripheral blood stem cells, thereby conditioning the subject for engraftment of transplanted peripheral blood stem cells.

In some embodiments, the method further comprises administering to the subject a cytokine selected from the group consisting of recombinant granulocyte colony-stimulating factor (G-CSF), granulocyte-macrophage colony-stimulating factor (GM-CSF), interleukin-3 (IL-3), and gyclosylated or pegylated forms thereof. In some embodiments, a cytokine selected from the group consisting of recombinant granulocyte colony-stimulating factor (G-CSF), granulocyte-macrophage colony-stimulating factor (GM-CSF), interleukin-3 (IL-3) and glycosylated or pegylated forms thereof, is not administered to the subject.

In some embodiments, the subject is conditioned for engraftment without chemotherapy or radiation therapy.

In some embodiments, the method further comprises transplanting CD34$^+$ peripheral blood stem cells into a subject in need of such transplantation.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In some aspects, the disclosure provides a method of treating a disease requiring peripheral blood stem cell transplantation in a subject in need of such treatment, comprising: (a) administering to a peripheral blood stem cell donor a combination of two or more mobilization agents selected from the group consisting of at least one heparan sulfate inhibitor, at least one CXCR2 agonist, and at least one CXCR4 antagonist in amounts effective to mobilize circulating peripheral blood stem cells in the donor; and (b) transplanting the mobilized circulating peripheral blood stem cells from the donor into a subject in need of a peripheral blood stem cell transplantation.

In some embodiments, the mobilized hematopoietic stem cells comprise CD34$^+$ peripheral blood stem cells. In some embodiments, the method further comprises harvesting the CD34$^+$ peripheral blood stem cells from the donor prior to transplantation into the subject.

In some embodiments, harvesting the mobilized hematopoietic stem cells comprises apheresis. In some embodiments, administration of the combination of two or more mobilization agents selected from the group consisting of the at least one heparan sulfate inhibitor, the at least one CXCR2 agonist, and the at least one CXCR4 antagonist to the donor is performed on the same day as the apheresis procedure.

In some embodiments, the apheresis procedure is performed within an hour of administration of the combination of two or more mobilization agents selected from the group consisting of the at least one heparan sulfate inhibitor, the at least one CXCR2 agonist, and the at least one CXCR4 antagonist.

In some embodiments, the method further comprises conditioning the subject in need of the peripheral blood stem cell transplantation for engraftment of transplanted peripheral blood stem cells prior to transplantation of the peripheral blood stem cells.

In some embodiments, conditioning comprises administering to the subject a combination of two or more mobilization agents selected from the group consisting of at least one heparan sulfate inhibitor, at least one CXCR2 agonist, and at least one CXCR4 antagonist in amounts effective to deplete hematopoietic stem cells in the conditioned subject's stem cell niche for subsequent engraftment in the conditioned subject's stem cell niche of transplanted peripheral blood stem cells.

In some embodiments, the subject is not administered a chemotherapy or radiotherapy treatment prior to transplantation of the peripheral blood stem cells.

In some embodiments, the donor and the subject are the same individual. In some embodiments, the donor and the subject are different individuals. In some embodiments, the donor and/or the subject is selected for exhibiting poor mobilization in response to administration of G-CSF alone. In some embodiments, the donor and/or the subject is selected for exhibiting poor mobilization in response to administration of Plerixafor alone. In some embodiments, the donor and/or the subject is selected for exhibiting poor mobilization in response to administration of a combination of G-CSF and Plerixafor.

In some embodiments, the subject is a patient presenting with a hematological malignancy. In some embodiments, the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the method further comprises administering to the subject a therapeutically effective amount of a conventional treatment for the hematological malignancy.

In some embodiments, the subject is a patient presenting with a non-malignant disease. In some embodiments, the non-malignant disease is selected from the group consisting of myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In some embodiments, the method further comprises administering to the subject a therapeutically effective amount of a conventional treatment for the non-malignant disease. In some aspects, the disclosure provides a method of selecting a subject who would benefit from hematopoietic stem cell remobilization using a combination of two or more mobilization agents selected from the group consisting of at least one heparan sulfate inhibitor, at least one CXCR2 agonist and at least one CXCR4 antagonist, comprising identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using a combination of two or more mobilization agents selected from the group consisting of at least one heparan sulfate inhibitor, at least one CXCR2 agonist, and at least one CXCR4 antagonist.

In some embodiments, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1, the at least one CXCR2 agonist is selected from the group consisting of Gro-beta or an analog or derivative thereof and Gro-betaΔ4 or an analog or derivative thereof, and the at least one CXCR4 antagonist is selected from the group consisting of Plerixafor or an analog or derivative thereof and Mozobil® or an analog or derivative thereof.

In some aspects, a method of conditioning a subject for engraftment of transplanted stem cells comprises administering to a subject at least one CXCR2 agonist in an amount effective to deplete hematopoietic stem cells from the subject's stem cell niche for subsequent engraftment in the subject's stem cell niche of transplanted stem cells, thereby conditioning the subject for engraftment of transplanted stem cells.

In some aspects, a method of conditioning a subject for engraftment of transplanted stem cells comprises administering to a subject at least one CXCR4 antagonist in an amount effective to deplete hematopoietic stem cells from the subject's stem cell niche for subsequent engraftment in the subject's stem cell niche of transplanted stem cells, thereby conditioning the subject for engraftment of transplanted stem cells.

In some aspects, a method of conditioning a subject for engraftment of transplanted stem cells comprises administering to a subject Gro-beta or an analog or derivative thereof, in an amount effective to deplete hematopoietic stem cells from the subject's bone marrow niche for subsequent engraftment in the subject's bone marrow niche of transplanted peripheral blood stem cells, thereby conditioning the subject for engraftment of transplanted peripheral blood stem cells.

In some aspects, a method of conditioning a subject for engraftment of transplanted peripheral blood stem cells comprises administering to a subject Gro-betaΔ4 or an analog or derivative thereof, in an amount effective to deplete hematopoietic stem cells from the subject's stem cell niche for subsequent engraftment in the subject's stem cell niche of transplanted stem cells, thereby conditioning the subject for engraftment of transplanted stem cells.

In some aspects, a method of conditioning a subject for engraftment of transplanted stem cells comprises administering to a subject Plerixafor or an analog or derivative thereof, in an amount effective to deplete hematopoietic stem cells from the subject's stem cell niche for subsequent engraftment in the subject's stem cell niche of transplanted stem cells, thereby conditioning the subject for engraftment of transplanted stem cells.

In some aspects, a method of conditioning a subject for engraftment of transplanted peripheral blood stem cells comprises administering to a subject a combination of two or more mobilization agents selected from the group consisting of at least one heparan sulfate inhibitor, at least one CXCR2 agonist, and at least one CXCR4 antagonist in an amounts effective to deplete hematopoietic stem cells from the subject's stem cell niche for subsequent engraftment in the subject's stem cell niche of transplanted stem cells, thereby conditioning the subject for engraftment of transplanted stem cells.

In some aspects, the disclosure provides a composition comprising a combination of two or more mobilization agents selected from the group consisting of at least one heparan sulfate inhibitor, at least one CXCR2 agonist, and at least one CXCR4 antagonist.

In some embodiments of this and other aspects of the disclosure, the combination of two or more mobilization agents selected from the group consisting of the at least one heparan sulfate inhibitor, the at least one CXCR2 agonist, and the at least one CXCR4 antagonist are selected from the group consisting of small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments of this and other aspects of the disclosure, the combination of two or more mobilization agents selected from the group consisting of the at least one heparan sulfate inhibitor, the at least one CXCR2 agonist, and the at least one CXCR4 antagonist are formulated for subcutaneous administration.

In some embodiments of this and other aspects of the disclosure, the at least one heparan sulfate inhibitor, the at least one CXCR2 agonist, and the at least one CXCR4 antagonist are selected from the group consisting of small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments of this and other aspects of the disclosure, the at least one CXCR2 agonist is Gro-beta or an analog or derivative thereof. In some embodiments of this and other aspects of the disclosure, the at least one CXCR2 agonist is Gro-beta$\Delta$4 or an analog or derivative thereof. In some embodiments of this and other aspects of the disclosure, the at least one CXCR4 antagonist is Plerixafor or an analog or derivative thereof. In some embodiments of this and other aspects of the disclosure, the at least one heparan sulfate inhibitor is selected from the group consisting of heparin sulfate or an analog or derivative thereof, protamine sulfate or an analog or derivative thereof, an agent that decreases the level or activity of EXT1, and an agent that decreases the level or activity of VCAM-1. In some embodiments of this and other aspects of the disclosure, the at least one CXCR2 agonist is selected from the group consisting of Gro-beta or an analog or derivative thereof and Gro-beta$\Delta$4 or an analog or derivative thereof. In some embodiments of this and other aspects of the disclosure, the at least one CXCR4 antagonist is Plerixafor or an analog or derivative thereof and Mozobil® or an analog or derivative thereof. In some embodiments of this and other aspects of the disclosure, the at least one CXCR2 agonist is Gro-beta or an analog or derivative thereof and the at least one CXCR4 antagonist is Plerixafor or an analog or derivative thereof. In some embodiments of this and other aspects of the disclosure, the at least one CXCR2 agonist is Gro-beta or an analog or derivative thereof and the at least one CXCR4 antagonist is Mozobil® or an analog or derivative thereof.

In some embodiments of this and other aspects of the disclosure, a composition or method described herein further comprises a cytokine, or administering to a subject a cytokine, selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof.

In some embodiments, the composition is useful for mobilizing hematopoietic stem cells into peripheral blood. In some embodiments, the composition is useful for remobilizing hematopoietic stem cells in subjects who exhibit poor mobilization in response to administration of one or more of G-CSF alone, and Plerixafor. In some embodiments, the composition is useful for conditioning a subject for engraftment of transplanted stem cells. In some embodiments, the composition is useful for rapid mobilization of hematopoietic stem cells from the stem cell niche into peripheral blood. In some embodiments, the composition mobilizes hematopoietic stem cells from the stem cell niche into peripheral blood in as little as 15 minutes.

In some aspects, a method of identifying a hematopoietic stem cell mobilizing agent comprises: (a) providing a CXCR2 protein or functional fragment thereof; (b) providing a test agent; and (c) assaying the ability of the test agent to agonize the CXCR2 protein or functional fragment thereof, wherein a test agent that agonizes the CXCR2 protein or functional fragment thereof is a candidate hematopoietic stem cell mobilizing agent.

In some aspects, a method of identifying a hematopoietic stem cell mobilizing agent comprises: (a) providing a CXCR4 protein or functional fragment thereof; (b) providing a CXCR4 binding partner; (c) providing a test agent; and (d) assaying the ability of the test agent to inhibit binding of the CXCR4 binding partner to the CXCR4 protein or functional fragment thereof, wherein a test agent inhibits binding of the CXCR4 binding partner to the CXCR4 protein or functional fragment thereof is a candidate hematopoietic stem cell mobilizing agent.

In some aspects, a method of identifying a hematopoietic stem cell mobilizing agent comprises: (a) providing a test agent; and (b) assessing the ability of the test agent to emulate the hematopoietic stem cell mobilizing effect of a combination of two or more mobilization agents selected from the group consisting of at least one heparan sulfate inhibitor, at least one CXCR2 agonist, and at least one CXCR4 antagonist.

In some embodiments, the at least one heparan sulfate inhibitor is selected from the group consisting of heparin sulfate or an analog or derivative thereof and protamine sulfate or an analog or derivative thereof, the at least one CXCR2 agonist is selected from the group consisting of Gro-beta or an analog or derivative thereof and Gro-beta$\Delta$4 or an analog or derivative thereof, and the at least one CXCR4 antagonist is selected from the group consisting of Plerixafor or an analog or derivative thereof and Mozobil® or an analog or derivative thereof.

In some aspects, the disclosure provides a kit comprising: (a) a combination of two or more mobilization agents selected from the group consisting of (i) at least one heparan sulfate inhibitor, (i) at least one CXCR2 agonist; and (iii) at least one CXCR4 antagonist; and (b) instructions for the administrating the combination of two or more mobilization agents selected from the group consisting of (i) at least one heparan sulfate inhibitor, (ii) at least one CXCR2 agonist, and (iii) the at least one CXCR4 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted stem cells; and (iv) treating a disease requiring stem cell transplantation in the subject.

In some embodiments, the combination of two or more mobilization agents selected from the group consisting of the at least one heparan sulfate inhibitor, the at least one CXCR2 agonist, and the at least one CXCR4 antagonist are selected from the group consisting of small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments, the at least one heparan sulfate inhibitor is selected from the group consisting of heparin sulfate or an analog or derivative thereof and protamine sulfate or an analog or derivative thereof, the at least one CXCR2 agonist is selected from the group consisting of Gro-beta or an analog or derivative thereof and Gro-betaΔ4 or an analog or derivative thereof, and the at least one CXCR4 antagonist is selected from the group consisting of Plerixafor or an analog or derivative thereof and Mozobil® or an analog or derivative thereof. In some embodiments, the kit further comprises one or more medical devices for transplanting the combination of two or more mobilization agents selected from the group consisting of the at least one heparan sulfate inhibitor, the at least one CXCR2 agonist, and the at least one CXCR4 antagonist into the subject.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A (top) shows the schema of the experimental design that produced the results shown in FIGS. 1B, 1C, and 1D. FIG. 1B shows hematopoietic progenitors measured by colony forming capacity are significantly increased in the blood. FIGS. 1C and 1D show that immunotypically defined progenitors (FIG. 1C, middle) and stem cells (FIG. 1D, right) are significantly decreased in the bone marrow after 6 months after deletion of EXT1. These results represent three independent experiments with 6-10 animals per experimental group. * $p<0.05$; ** $p<0.01$.

FIG. 2A shows a schema of the experimental design that produced the results shown in FIGS. 2B and 2C. FIGS. 2B and 1C show that VCAM-1 induced mobilization depends on Ext1/heparan sulfate proteoglycans as shown by colony forming unit assays (FIG. 2B, lower left panel) and competitive repopulation assays (FIG. 2C, lower right panel). These results represent two independent experiments with 5 animals per experimental group  $p<0.05$; * $p<0.01$; ns=non-significant.

FIG. 3A (top) shows the schema of the experimental design that produced the results shown in FIGS. 3B and 3C. FIG. 3B shows that heparin significantly enhances G-CSF induced mobilization as measured by serial competitive transplant (lower left panel). FIG. 3C shows that the enhanced mobilization achieved by the combination of G-CSF and heparin depends on intact, endogenous HSPGs (lower right panel). These results represent three independent experiments with 6-10 animals per experimental group. * $p<0.05$;  $p<0.01$; * $p<0.001$.

FIG. 5A is a schematic overview depicting the experimental design. FIG. 5B-5J relates to data collected 24 weeks after pIpC induction. FIGS. 5B and 5C are bar graphs illustrating the results of bone marrow analysis showing contribution to committed myeloid progenitors (common myeloid progenitor (CMP), granulocyte-monocyte progenitor (GMP), and megakaryocyte-erythrocyte progenitors (MEP)) and committed lymphoid progenitors (CLP) (FIG. 1B), and to KLS CD48−CD150+ HSCs (FIG. 5C). FIG. 5D is a bar graph illustrating apoptosis in the bone marrow KLS CD48−CD150+ cell population. FIG. 5E is a bar graph showing the results of a cell cycle analysis of bone marrow KLS CD48-CD150+HSCs, depicting the percentage of cells in the G0, G1 and S-G2-M phases of the cell cycle. FIG. 5F is a bar graph showing peripheral white blood cell (WBC) count. FIG. 5G is a bar graph showing the peripheral blood analysis depicting the number of circulating progenitor cells measured by colony forming unit assay (CFU) in methylcellulose in chimeric mice. FIGS. 5H-K are bar graphs showing the results of spleen analysis depicting total weight (mg) (FIG. 5H), contribution to KLS 48−CD150+ HSCs (FIG. 5I), contribution to CMP, GMP and MEP cells (FIG. 5J), and relative PB reconstitution, 16 weeks post transplantation, of recipient C57BL/6J (CD45.2) mice transfused with spleen cells from control or mutant chimeric mice (CD45.1) competed with equal numbers of WT CD45.2 spleen cells (FIG. 5K). FIG. 5L shows representative three-dimensional microCT images of femoral cortical bone (top panels) and cancellous bone (lower panels) of control (n=8) and mutant (n=4-5) mice. Data representative of at least 3 independent experiments, n=5-8 mice per genotype per experiment. Data are represented as mean±SEM. * $p<0.05$; ** $p<0.01$.

FIGS. 6A-6C depict the evaluation of Ext1 deletion in BM Mx1+ mesenchymal cells. FIG. 6A is a schematic illustration depicting how control and mutant mice were bred into a ROSA26-loxP-stop-loxP-EYFP (Rosa-YFP) strain to facilitate prospective isolation of CD45−Ter119−Mx1+ cells. FIG. 6B shows a western blot of Ext1 in ex vivo expanded BM CD45−Ter119−Mx1+(YFP+) cells from control and mutant mice (n=3 per genotype), Gapdh is shown as loading control. FIG. 6C is a bar graph showing the quantification performed by measuring the optical density of the Ext1 band relative to that of Gapdh. FIGS. 6D-F are bar graphs depicting the quantification of HS levels in ex vivo expanded (FIG. 6D), and freshly isolated (FIG. 6E) BM CD45−Ter119−Mx1+BM cells from control and mutant mice. FIG. 6F is a bar graph depicting bone marrow analysis showing contribution to CD45−Ter119−Mx1+CD105+CD140+Sca1+ mesenchymal stem cells in control and mutant mice. FIGS. 6G-6K illustrate the analysis of peripheral blood hematopoietic parameters of chimeric Ext1 control and mutant mice before pIpC induction 6 to 8 weeks after transplantation showing frequency of the donor cell population (CD45.1) (FIG. 6G), white blood cell (WBC) count (FIG. 6H), red blood cell (RBC) count (FIG. 6I), platelet (PLT) count (FIG. 6J) and contribution to B cells (B220), myeloid cells (Mac1 and Gr1) and T cells (CD3) (FIG. 6K). FIGS. 6L-6S depict the analysis of chimeric Ext1 control and mutant mice 24 weeks after pIpC induction. FIG. 6L is a bar graph showing total body weight (TBW) (g). FIGS. 6M and 6N are bar graphs illustrating bone marrow analysis showing total BM cellularity (FIG. 6M) and contribution to B cells (B220), myeloid cells (Mac1 and Gr1) and T cells (CD3) (FIG. 6N) in recipient mice. FIGS. 6O-6Q are bar graphs depicting peripheral blood analysis showing contribution to B cells (B220), myeloid cells (Mac1 and Gr1) and T cells (CD3) (FIG. 6O), Platelet counts (PLT) (FIG. 6P) and Red blood cell counts (RBC) (FIG. 6Q) in recipient mice. FIGS. 6R and 6S are graphs depicting spleen-resident KLS CD48−CD150+HSCs analysis showing cell cycle analysis (FIG. 6R); cells in G0, G1 and S-G2-M phases of the cell cycle are shown and apoptosis (FIG. 6S) in control and mutant chimeric mice. FIG. 6T is a bar graph depicting PB reconstitution, 16 weeks post transplantation, of recipient C57BL/6J (CD45.2) mice transfused with spleen cells from control or mutant chimeric mice (CD45.1) competed with equal numbers of WT CD45.2 spleen cells showing contribution to B cells (B220), myeloid cells (Mac1 and Gr1) and T cells (CD3). FIG. 6U is a bar graph showing the distribution of CD62Low circulating neutrophils in chimeric control and mutant mice 24 weeks after pIpC induction. FIG. 6V Is a bar graph showing Cxcl12 protein levels in the BM of control and mutant chimeric mice 24 weeks after pIpC induction. FIG. 6W shows representative hematoxylin and eosin staining of femurs from chimeric Ext1 control and mutant mice 24 weeks after pIpC induction. Magnification: upper panels 4×, lower panels 40×. Data representative of at least 2 independent experiments, n=5-8 mice per genotype per experiment unless otherwise stated. Data are represented as mean±SD or median±IQR (interquartile range). ns: nonsignificant; * p<0.05; ** p<0.01.

FIGS. 7A and 7B depict the relative positioning of HSCs in the BM cavity. FIG. 7A shows control and mutant mice were bred into a strain expressing GFP under the Col2.3 promoter labeling osteoblastic cells. FIG. 7B shows the distances of LKS CD48−CD150+HSCs 24 hours after transplantation, from Col2.3GFP cells (left panels) and endosteal surface (right panels) in μm. FIGS. 7C and 7D depict expression of niche-related molecules in Mx1+ cells. FIG. 7C shows Real-Time PCR results for Vcam1, Cxcl12, Angpt1 and Scf1. FIG. 7D is a representative histogram of Vcam1 protein levels in BM CD45−Ter119−Mx1+ cells from control and mutant mice. FIGS. 7E, 7F and 7G depict the functional evaluation of Vcam1 in Mx-1+ cells. FIG. 7E is a schematic overview of the experimental design. FIG. 7F shows the number of circulating progenitors measured by CFU-C assay in peripheral blood of control and mutant mice injected with G-CSF and Vcam1 neutralizing antibody. FIG. 7G shows total peripheral blood reconstitution, 16 weeks post transplantation, in recipient mice transfused with 150 μL of peripheral blood from control or mutant mice mobilized with G-CSF and Vcam1 neutralizing antibody or isotype control. CD45.1 BM cells were transplanted for radioprotection in equal numbers in control and mutant mice. Data representative of at least 2 independent experiments, n=5-8 mice per genotype per experiment. In mobilization experiments, PB was collected from at least 5 mice per experimental group. Data are represented as mean±SD. ns: non-significant; * p<0.05;  p<0.01; * p<0.001.

FIG. 8A shows representative pictures of the bone marrow cavity of control and mutant mice injected with equal numbers of DID-labeled HSCs (red); blue, second-harmonic generation signal (bone); green, Col2.3GFP (osteoblasts). Scale bars, 100 μm. FIG. 8B shows Cxcl12 protein level quantification in CD45−Ter119−Mx1+ mesenchymal cells from control and mutant Ext1 mice. FIG. 8C shows Vcam1 protein level quantification in CD45−Ter119−Mx1+ mesenchymal cells from control and mutant Ext1 mice. FIG. 8D shows the quantification of peripheral blood circulating progenitor cells measured by colony forming unit assay (CFU) from Ext1 control or mutant mice receiving Vcam1 neutralizing antibody or isotype control. Data representative of at least 2 independent experiments, n=5-8 mice per genotype per experiment unless otherwise stated. Data are represented as mean±SD. ns: non-significant; * p<0.05; ** p<0.01.

FIG. 9A is a schematic overview of the experimental design. FIG. 9B is a graph showing peripheral WBC counts in C57BL6/J (CD45.2) mice receiving G-CSF or G-CSF plus heparin. FIG. 9C shows total donor (CD45.2) reconstitution of G-CSF or G-CSF plus heparin mobilized PB from C57BL/6J (CD45.2) transplanted into lethally irradiated CD45.1 congenic recipients. CD45.1 BM cells were transplanted for radioprotection in equal numbers in both groups. The break in the X-axis represents serial BM transplantation into lethally irradiated recipients. FIGS. 9D-9F illustrate clustering of genes differentially expressed in FACS sorted HSPCs (Lin−, cKit+, Sca1+) from PB upon GCSF (n=1) or G-CSF plus heparin (n=2) induced mobilization showing changes in cell adhesion genes (FIG. 9D), cell proliferation genes (FIG. 9E) and growth regulation genes (FIG. 9F). Blue and yellow represent higher and lower expression respectively. FIGS. 9G-9H show non-competitive transplantation of G-CSF or G-CSF plus heparin mobilized PB into lethally irradiate recipients showing neutrophil (FIG. 9G) and platelet recovery FIG. 9H). FIG. 9I shows total donor (CD45.2) reconstitution of G-CSF or G-CSF plus heparin mobilized PB from Ext1 mutant mice transplanted into lethally irradiated CD45.1 congenic recipients. CD45.1 BM cells were transplanted for radioprotection in equal numbers in both groups, FIG. 9J shows the relative PB reconstitution, 16 weeks post transplantation, of recipient CD45.1 mice transfused with PB from C57BL/6J mice (CD45.2) receiving G-CSF and heparin or G-SCF and hirudin. Recipient mice were lethally irradiated and received CD45.1 cells for radioprotection. FIGS. 9K-9L depict the relative PB reconstitution, 16 weeks post transplantation, of recipient mice transfused with G-CSF mobilized PB from non-diabetic and diabetic control and mutant mice (4 groups in total) (FIG. 9K) or G-CSF plus heparin mobilized PB from non-diabetic and diabetic C57BL/6J mice (FIG. 9L). For the transplants lethally irradiated CD45.1 animals were used as recipients. CD45.1 BM was used in equal numbers for radioprotection. FIG. 9M shows that Vcam1 inhibition abrogates heparin-induced mobilization. Peripheral blood circulating progenitor cells measured by colony forming unit assay (CFU) of animals receiving vehicle, AMD3100 or Vcam1 neutralizing antibody alone or in combination with heparin, Data representative of at least 2 independent experiments, n=5-8 mice per genotype per experiment. In mobilization experiments, PB was collected from at least 5 mice per experimental group. Data are represented as mean±SD or median±IQR (interquartile range). ns: non-significant; * $p<0.05$;  $p<0.01$; * $p<0.001$.

FIG. 10A shows peripheral WBC counts in C57BL/6J mice receiving vehicle (PBS) or heparin. FIG. 10B shows peripheral blood circulating progenitor cells measured by colony forming unit assay (CFU) in C57BL/6J mice receiving vehicle (PBS) or heparin. FIG. 10C is a representative image of a CFU assay showing PB circulating progenitor cell colonies from C57BL/6J mice receiving vehicle, AMD3100 or Vcam1 neutralizing antibody alone or in combination with heparin. FIG. 10D shows Vcam1 protein level quantification in CD45−Ter119−Mx1+ mesenchymal cells from C57BL/6J mice receiving vehicle (PBS) or heparin. FIG. 10E shows the relative PB reconstitution, 16 weeks post transplantation, of recipient CD45.1 mice transfused with PB from Ext1 control or mutant mice (CD45.2) receiving G-CSF alone or in combination with AMD3100. Recipient mice were lethally irradiated and received CD45.1 cells for radioprotection.

FIG. 11A is a graph showing total PB reconstitution of non-conditioned control mice infused with $10^6$ and $8\times10^6$ CD45.1 congenic BM cells and mutant recipient mice infused with $10^6$, $4\times10^6$ and $8\times10^6$ CD45.1 congenic BM cells. FIG. 11B is a bar graph showing PB analysis 16 weeks after non-conditioned transplantation of $8\times10^6$ CD45.1 congenic BM cells into EXT-1 mutant recipient mice showing the contribution to B cells (B220), myeloid cells (Mac1 and Gr1) and T cells (CD3). FIG. 11C is a schematic illustration of a proposed model for the functional role of EXT-1/HSPG expressed in the niche. n=5 mice per genotype. Data are represented as mean±SEM. * $p<0.05$; ** $p<0.01$.

DETAILED DESCRIPTION OF THE INVENTION

Figures 1A, 1B, 1C, 1D:
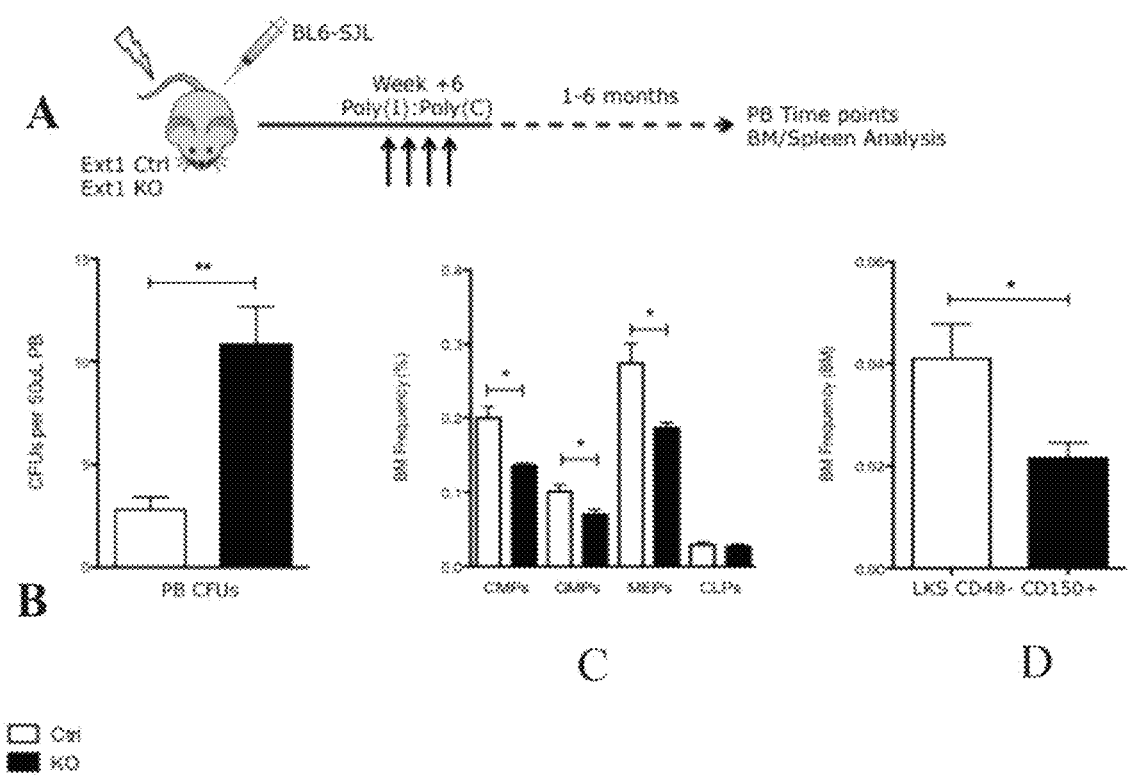
FIGS. 1A, 1B, 1C, and 1D illustrate that heparan sulfate proteoglycans are essential for HSPC retention in the bone marrow and deletion of the glycosyltransferase gene, EXT1, results in gradual changes in HSPC localization.

The disclosure relates to mobilization of stem cells and/or progenitor cells (e.g., hematopoietic stem cells and/or progenitor cells) for use in connection with stem cell transplantations. Briefly, the stem cell transplantation process may include any or all of injection of mobilization agents into a subject (e.g., a donor), mobilization of the subject's stem cells into the subject's blood from the bone marrow space, collection of the mobilized stem cells from the blood (e.g., via apheresis), preparation of the collected stem cells for storage (e.g., in an infusion bag), cryopreservation of the collected and stored mobilized stem cells, conditioning a subject for engraftment of stored mobilized stem cells to be transplanted, transplantation of the stem cells into the conditioned subject, and engraftment and recovery as evidenced by increasing absolute neutrophil and platelet counts in the subject. (See Haematopoietic Stem Cell Mobilization and Apheresis: A Practical Guide for Nurses and Other Allied Health Care Professionals, European Group for Blood and Marrow Transplantation-Nurses Group, the contents of which are incorporated herein by reference).

The disclosure contemplates the use of methods, compositions, agents, and kits in connection with any of the procedures involved in stem cell transplantation, for example, methods of mobilizing stem cells, methods of harvesting mobilized stem cells for transplantation, methods of preserving harvested mobilized stem cells for subsequent transplantation, methods of conditioning a subject for enhanced engraftment of transplanted stem cells, methods of treating a disease requiring stem cell transplantation, methods of selecting a subject for stem cell mobilization, and compositions, agents, and kits for use in the methods.

Mobilizing HSPCs

Certain aspects of the present invention relate to methods of mobilizing hematopoietic stem cells and/or progenitor cells. As used herein, "mobilizing" and "mobilizing hematopoietic stem cells and/or progenitor cells" are used interchangeably to refer to the act of inducing the migration of hematopoietic stem sells and/or progenitor cells from a first location (e.g., stem cell niche, e.g., bone marrow) into a second location (e.g., tissue (e.g., peripheral blood) or organ (e.g., spleen). The work described herein demonstrates that heparin sulfate proteoglycans (HSPGs) are involved in maintaining hematopoietic stem cell and/or progenitor cell retention in the bone marrow stem cell niche. In particular, the present inventors have surprisingly and unexpectedly demonstrated that deletion of Exostosin-1 (GeneID: 2131, EXT-1, also known as EXT, LGS, TTV, LGCR, and TRPS2), a glycosyltransferase gene essential for the production of heparan sulfate, caused hematopoietic stem cells and/or progenitor cells to egress from the bone marrow. Surprisingly, and unexpectedly, the present inventors have further demonstrated that inhibition (e.g., pharmacological) of heparan sulfate (e.g., endogenous) enhances hematopoietic stem cell and/or progenitor cell mobilization even in situations in which mobilization resistance would otherwise result in poor mobilization.

Certain aspects disclosed herein rely on the remarkable work described herein demonstrating that a combination of at least one CXCR2 agonist and at least one CXCR4 antagonist is significantly more effective at mobilizing hematopoietic stem cells and/or progenitor cells as compared to mobilization of hematopoietic stem cells and/or progenitor cells using G-CSF alone, or in combination with Plerixafor. Accordingly, in some aspects the disclosure provides methods and compositions relating to mobilizing hematopoietic stem cells and/or progenitor cells using at least one CXCR2 agonist (e.g., Gro-beta) and at least one CXCR4 antagonist (e.g., Plerixafor).

Certain aspects disclosed herein rely on the remarkable work described herein demonstrating that a combination of G-CSF and at least one heparan sulfate inhibitor is significantly more effective at mobilizing hematopoietic stem cells and/or progenitor cells as compared to mobilization of hematopoietic stem cells and/or progenitor cells using G-CSF alone. Accordingly, in some aspects the disclosure provides methods and compositions relating to mobilizing hematopoietic stem cells and/or progenitor cells using a combination of G-CSF and at least one heparan sulfate inhibitor (e.g., heparin sulfate).

Certain aspects disclosed herein rely on the remarkable work described herein demonstrating that a combination of at least one CXCR4 antagonist and at least one heparan sulfate inhibitor is significantly more effective at mobilizing hematopoietic stem cells and/or progenitor cells as compared to mobilization of hematopoietic stem cells and/or progenitor cells using Plerixafor alone. Accordingly, in some aspects the disclosure provides methods and compositions relating to mobilizing hematopoietic stem cells and/or progenitor cells using a combination of at least one heparan sulfate inhibitor (e.g., heparin sulfate) and at least one CXCR4 antagonist (e.g., Plerixafor).

Accordingly, the present invention provides various methods of mobilizing hematopoietic stem cells and/or progenitor cells in a subject.

In an aspect, a method of mobilizing hematopoietic stem cells and/or progenitor cells in a subject comprises administering to a subject an effective amount of an agent that inhibits the level or activity of exostosin 1 (EXT-1) in the subject, thereby mobilizing hematopoietic stem cells and/or progenitor cells in the subject. In an aspect, a method of mobilizing hematopoietic stem cells and/or progenitor cells in a subject comprises administering to a subject an effective amount of an agent that inhibits the level or activity of heparan sulfate proteoglycans, thereby mobilizing hematopoietic stem cells and/or progenitor cells in the subject.

Certain aspects of the methods of mobilizing hematopoietic stem cells and/or progenitor cells in a subject generally involve employing combinations of two or more of at least one CXCR2 agonist, at least one CXCR4 antagonist, at least one heparan sulfate inhibitor, and G-CSF.

An exemplary method of mobilizing hematopoietic stem cells and/or progenitor cells in a subject comprises administering to a subject a combination of any two or more mobilization agents selected from the group consisting of at least one CXCR2 agonist, at least one CXCR4 antagonist, at least one heparan sulfate inhibitor, and G-CSF in amounts sufficient to mobilize hematopoietic stem cells and/or progenitor cells into peripheral blood.

Another exemplary method of mobilizing hematopoietic stem cells and/or progenitor cells in a subject comprises administering to a subject at least one CXCR2 agonist and at least one CXCR4 antagonist in amounts effective to mobilize hematopoietic stem cells and/or progenitor cells into the subject's peripheral blood.

Still another exemplary method of mobilizing hematopoietic stem cells and/or progenitor cells in a subject comprises administering to a subject at least one heparan sulfate inhibitor in combination with either G-CSF or at least one CXCR4 antagonist in amounts effective to mobilize hematopoietic stem cells and/or progenitor cells into the subject's peripheral blood.

Yet still another exemplary method of mobilizing hematopoietic stem cells and/or progenitor cells in a subject comprises administering to a subject at least one heparan sulfate inhibitor in combination with at least one CXCR4 antagonist in amounts effective to mobilize hematopoietic stem cells and/or progenitor cells into the subject's peripheral blood.

A further exemplary method of mobilizing hematopoietic stem cells and/or progenitor cells in a subject comprises administering to a subject at least one heparan sulfate inhibitor in combination with at least one CXCR2 agonist in amounts effective to mobilize hematopoietic stem cells and/or progenitor cells into the subject's peripheral blood.

Still a further exemplary method of mobilizing hematopoietic stem cells and/or progenitor cells in a subject comprises administering to a subject at least one heparan sulfate inhibitor in combination with at least one CXCR2 agonist in amounts effective to mobilize hematopoietic stem cells and/or progenitor cells into the subject's peripheral blood.

Still a further exemplary method of mobilizing hematopoietic stem cells and/or progenitor cells in a subject comprises administering to a subject a combination of at least one heparan sulfate inhibitor, at least one CXCR4 antagonist, and at least one CXCR2 agonist in amounts effective to mobilize hematopoietic stem cells and/or progenitor cells into the subject's peripheral blood.

Still another exemplary method of mobilizing hematopoietic stem cells and/or progenitor cells in a subject comprises administering to a subject a combination of at least one heparan sulfate inhibitor, at least one CXCR4 antagonist, at least one CXCR2 agonist, and G-CSF in amounts effective to mobilize hematopoietic stem cells and/or progenitor cells into the subject's peripheral blood.

Certain aspects of the invention relate to enhancing hematopoietic stem cell and/or progenitor cell mobilization in individuals exhibiting stem cell and/or progenitor cell mobilopathy. Surprisingly, and unexpectedly, the work described herein demonstrates that the agents described herein are effective at overcoming diabetes-induced mobilopathy. Accordingly, without wishing to be bound by theory, it is believed that the agents described herein can be used to enhance hematopoietic stem cell and/or progenitor cell mobilization in individuals who exhibit hematopoietic stem cell and/or progenitor cell mobilopathy. As will be appreciated by those skilled in the art enhanced mobilization of hematopoietic stem cells and/or progenitor cells in individuals who exhibit hematopoietic stem cell and/or progenitor cell mobilopathy has a variety of useful applications, for example to mobilize cells in the subject for subsequent harvest and transplantation, or to condition the subject for subsequent engraftment, or a combination thereof, amongst others.

In an aspect, the invention provides a method of enhancing hematopoietic stem cell and/or progenitor cell mobilization in a subject who exhibits hematopoietic stem cell and/or progenitor cell mobilopathy, the method comprising administering to the subject an effective amount of an agent that inhibits the level or activity of EXT-1, thereby enhancing hematopoietic stem cell and/or progenitor cell mobilization in the subject. In an aspect, the invention provides a method of enhancing hematopoietic stem cell and/or progenitor cell mobilization in a subject who exhibits diabetes-induced hematopoietic stem cell and/or progenitor cell mobilopathy, the method comprising administering to the subject an effective amount of an agent that inhibits the level or activity of EXT-1, thereby enhancing hematopoietic stem cells and/or progenitor cell mobilization in the subject.

In an aspect, the invention provides a method of enhancing hematopoietic stem cell and/or progenitor cell mobilization in a subject who exhibits hematopoietic stem cell and/or progenitor cell mobilopathy, the method comprising administering to the subject an effective amount of an agent that inhibits the level or activity of heparan sulfate proteoglycans, thereby enhancing hematopoietic stem cell and/or progenitor cell mobilization in the subject. In an aspect, the invention provides a method of enhancing hematopoietic stem cell and/or progenitor cell mobilization in a subject who exhibits diabetes-induced hematopoietic stem cell and/or progenitor cell mobilopathy, the method comprising administering to the subject an effective amount of an agent that inhibits the level or activity of heparan sulfate proteoglycans, thereby enhancing hematopoietic stem cells and/or progenitor cell mobilization in the subject.

In some embodiments, the method of enhancing hematopoietic stem cell and/or progenitor cell mobilization in a subject who exhibits hematopoietic stem cell and/or progenitor cell mobilopathy comprises selecting a subject who exhibits hematopoietic stem cell and/or progenitor cell mobilopathy. Selecting a subject who exhibits hematopoietic stem cell and/or progenitor cell mobilopathy can be performed according to any technique available to the skilled artisan. For example, the subject can be selected for exhibiting poor mobilization to a conventional mobilization agent (e.g., G-CSF). In some embodiments, the subject is a subject suffering from a disease, condition, or disorder which is reported to induce mobilopathy, such as diabetes. Other suitable techniques for selecting subjects exhibiting mobilopathy are apparent to the skilled artisan.

As used herein, "hematopoietic stem cells" refers to stem cells that can differentiate into the hematopoietic lineage and give rise to all blood cell types such as white blood cells and red blood cells, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). "Stem cells" are defined by their ability to form multiple cell types (multipotency) and their ability to self-renew. Hematopoietic stem cells can be identified, for example by cell surface markers such as CD34−, CD133+, CD48−, CD150+, CD244−, cKit+, Sca1+, and lack of lineage markers (negative for B220, CD3, CD4, CD8, Mac1, Gr1, and Ter119, among others). Methods of identifying and analyzing hematopoietic stem cells has been reviewed by Challen et al. (see e.g., "Mouse Hematopoietic Stem Cell Identification and Analysis," *Cytometry A*. 2009; 75(1):14-24, incorporated herein by reference in its entirety). The methods described herein contemplate any stem cell which would be useful for transplantation, including, but not limited to, peripheral blood stem cells, bone marrow stem cells, umbilical cord stem cells, genetically modified stem cells, etc.).

As used herein, the term "hematopoietic progenitor cells" encompasses pluripotent cells which are committed to the hematopoietic cell lineage, generally do not self-renew, and are capable of differentiating into several cell types of the hematopoietic system, such as granulocytes, monocytes, erythrocytes, megakaryocytes, B-cells and T-cells, including, but not limited to, short term hematopoietic stem cells (ST-HSCs), multi-potent progenitor cells (MPPs), common myeloid progenitor cells (CMPs), granulocyte-monocyte progenitor cells (GMPs), megakaryocyte-erythrocyte progenitor cells (MEPs), and committed lymphoid progenitor cells (CLPs). The presence of hematopoietic progenitor cells can be determined functionally as colony forming unit cells (CFU-Cs) in complete methylcellulose assays, or phenotypically through the detection of cell surface markers (e.g., CD45−, CD34+, Ter119−, CD16/32, CD127, cKit, Sca1) using assays known to those of skill in the art.

Generally, the methods of mobilizing hematopoietic stem cells and/or progenitors cells are capable of mobilizing any hematopoietic stem cells and/or progenitor cells in which heparan sulfate proteoglycans are responsible for maintaining adhesion of the hematopoietic stem cells and/or progenitor cells in their cell niche. In some embodiments, the mobilized hematopoietic stem cells comprise KLS-CD150+ CD48− cells. In some embodiments, the mobilized hematopoietic stem cells comprise CD34−CD133+ cells. In some embodiments, the mobilized hematopoietic stem cells and/or progenitor cells comprise common myeloid progenitor cells. In some embodiments, the mobilized hematopoietic stem cells and/or progenitor cells comprise granulocyte/monocyte progenitor cells. In some embodiments, the mobilized hematopoietic stem cells and/or progenitor cells comprise megakaryocyte/erythroid progenitor cells. In some embodiments, the mobilized hematopoietic stem cells and/or progenitor cells comprise committed lymphoid progenitor cells. In some embodiments, the mobilized hematopoietic stem cells and/or progenitor cells comprise a combination of common myeloid progenitor cells, granulocyte/monocyte progenitor cells, megakaryocyte/erythroid progenitor cells. In some embodiments, the hematopoietic progenitor cells comprise CD150−CD48−CD244+ cells. In some embodiments, the hematopoietic progenitor cells comprise CD150−CD48+ CD244+ cells. In some embodiments, the hematopoietic progenitor cells comprise Lin−SCA-1⁻c-Kit+CD34+CD16/ 32$^{mid}$ cells. In some embodiments, the hematopoietic progenitor cells comprise lin−SCA-1-c-kit+CD34−CD16/32$^{low}$ cells.

The present invention contemplates mobilizing hematopoietic stem cells and/or progenitor cells for any purpose which would be desirable to the skilled artisan. Those skilled in the art will appreciate that mobilization of hematopoietic stem cells and/or progenitor cells provides a more accessible source of hematopoietic stem cells and/or progenitor cells that can be harvested (e.g., via apheresis) for transplantation, for example by increasing the number of hematopoietic stem cells and/or progenitor cells in the peripheral blood. In some embodiments, the methods comprise harvesting the stem cells and/or progenitor cells mobilized in the subject. In some embodiments, the methods comprise transplanting the harvested stem cells and/or progenitor cells into a subject in need of such transplantation. In some embodiments, the hematopoietic stem cells and/or progenitor cells mobilized in a subject are harvested for autologous transplantation into the subject. In some embodiments, the hematopoietic stem cells and/or progenitor cells mobilized in the subject are harvested for allogeneic transplantation into a recipient subject.

In some embodiments, the methods described herein are useful for mobilizing hematopoietic stem cells and/or progenitor cells in response to poor mobilization utilizing a conventional hematopoietic stem cell and/or progenitor cell mobilization regimen (e.g., G-CSF).

In some embodiments, the methods described herein comprise administering to the subject a cytokine selected from the group consisting of recombinant granulocyte colony-stimulating factor (G-CSF), granulocyte-macrophage colony-stimulating factor (GM-CSF), interleukin-3 (IL-3), and glycosylated or pegylated forms thereof. In some embodiments, the methods described herein comprise administering to the subject a combination of G-CSF or a glycosylated or pegylated form thereof and heparin.

In some embodiments, the hematopoietic stem cells and/ or progenitor cells are mobilized in a subject to condition the subject for engraftment of transplanted hematopoietic stem cells and/or progenitors cells, for example by decreasing the number of hematopoietic stem cells and/or progenitor cells in a stem niche (e.g., bone marrow) into which the transplanted cells can engraft.

Aspects of the inventive methods disclosed herein (e.g., methods of mobilizing hematopoietic stem cells and/or progenitor cells) involve harvesting the mobilized stem cells (e.g., $CD34^+$ and/or $CD133^+$ peripheral blood stem cells). Accordingly, in some aspects, the disclosure provides methods of harvesting peripheral blood stem cells for transplantation in a subject in need of such cells. An exemplary method of harvesting peripheral blood stem cells for transplantation in a subject in need of such cells comprises: (a) administering to a peripheral blood stem cell donor a combination of two or more mobilization agents selected from the group consisting of at least one CXCR2 agonist, at least one CXCR4 antagonist, and at least one heparan sulfate inhibitor in amounts effective to mobilize circulating peripheral blood stem cells in the donor; and (b) harvesting the mobilized circulating peripheral blood stem cells from the donor for transplantation in a subject.

In some embodiments, a method of harvesting peripheral blood stem cells for transplantation in a subject in need of such cells comprises: (a) administering to a peripheral blood stem cell donor a combination of two or more mobilization agents selected from the group consisting of at least one CXCR2 agonist, at least one CXCR4 antagonist, at least one heparan sulfate inhibitor, and G-CSF in amounts effective to mobilize circulating peripheral blood stem cells in the donor; and (b) harvesting the mobilized circulating peripheral blood stem cells from the donor for transplantation in a subject.

In some embodiments, a method of harvesting peripheral blood stem cells for transplantation in a subject in need of such cells comprises: (a) administering to a peripheral blood stem cell donor a combination of two or more mobilization agents selected from the group consisting of at least one CXCR2 agonist, at least one CXCR4 antagonist, at least one heparan sulfate inhibitor, and G-CSF in amounts effective to mobilize circulating peripheral blood stem cells in the donor; and (b) harvesting the mobilized circulating peripheral blood stem cells from the donor for transplantation in a subject.

In some embodiments, a method of harvesting peripheral blood stem cells for transplantation in a subject in need of such cells comprises: (a) administering to a peripheral blood stem cell donor a combination of three or more mobilization agents selected from the group consisting of at least one CXCR2 agonist, at least one CXCR4 antagonist, at least one heparan sulfate inhibitor, and G-CSF in amounts effective to mobilize circulating peripheral blood stem cells in the donor; and (b) harvesting the mobilized circulating peripheral blood stem cells from the donor for transplantation in a subject.

Another exemplary method of harvesting peripheral blood stem cells for transplantation in a subject in need of such cells comprises: (a) administering to a peripheral blood stem cell donor at least one CXCR2 agonist and at least one CXCR4 antagonist in amounts effective to mobilize circulating peripheral blood stem cells in the donor; and (b) harvesting the mobilized circulating peripheral blood stem cells from the donor for transplantation in a subject.

Still another exemplary method of harvesting peripheral blood stem cells for transplantation in a subject in need of such cells comprises: (a) administering to a peripheral blood stem cell donor at least one heparan sulfate inhibitor and at least one CXCR4 antagonist in amounts effective to mobilize circulating peripheral blood stem cells in the donor; and (b) harvesting the mobilized circulating peripheral blood stem cells from the donor for transplantation in a subject.

Yet another exemplary method of harvesting peripheral blood stem cells for transplantation in a subject in need of such cells comprises: (a) administering to a peripheral blood stem cell donor at least one heparan sulfate inhibitor and at least one CXCR2 agonist in amounts effective to mobilize circulating peripheral blood stem cells in the donor; and (b) harvesting the mobilized circulating peripheral blood stem cells from the donor for transplantation in a subject.

Still yet another exemplary method of harvesting peripheral blood stem cells for transplantation in a subject in need of such cells comprises: (a) administering to a peripheral blood stem cell donor at least one heparan sulfate inhibitor and G-CSF in amounts effective to mobilize circulating peripheral blood stem cells in the donor; and (b) harvesting the mobilized circulating peripheral blood stem cells from the donor for transplantation in a subject.

It should be appreciated that the descriptions above with respect to harvesting, conditioning, and transplanting are equally applicable to the harvesting method aspects described here.

The disclosure contemplates the use of any suitable method of harvesting and/or collecting mobilized stem cells. In some embodiments harvesting the mobilized hematopoietic stem cells and/or progenitor cells comprises apheresis. The work described herein demonstrates that the combination of at least one CXCR2 agonist (e.g., Gro-beta or Gro-betaΔ4) and at least one CXCR4 antagonist (e.g., Plerixafor or Mozobil®) rapidly and efficiently mobilize stem cells, and exhibit increased efficiencies compared to G-CSF and Plerixafor (alone or in combination). As a result, in some embodiments the methods described herein allow for the apheresis procedure to be performed on the same day that the at least one CXCR2 agonist and the at least one CXCR4 antagonist are administered to the subject. In some embodiments the methods described herein allow for the apheresis procedure to be performed on the same day that the at least one heparan sulfate inhibitor and G-CSF are administered to the subject. In some embodiments the methods described herein allow for the apheresis procedure to be performed on the same day that the at least one heparan sulfate inhibitor are administered to the subject. In other words, harvesting mobilized stem cells from a subject (e.g., a donor) via apheresis can be perform on the same day that the mobilization agents are administered to the subject during a single visit to a healthcare facility.

In some instances, the apheresis procedure can begin in as little as 15 minutes after administration of the at least one CXCR2 agonist and the at least one CXCR4 antagonist. In some embodiments, the apheresis procedure can begin in as little as 20 minutes, 22 minutes, 25 minutes, 30 minutes, 35 minutes, 40 minutes, 47 minutes, 52 minutes, 58 minutes, or an hour after administration of the at least one CXCR2 agonist and the at least one CXCR4 antagonist.

In some instances, the apheresis procedure can begin in as little as 15 minutes after administration of the at least one heparan sulfate antagonist and the at least one CXCR4 antagonist. In some embodiments, the apheresis procedure can begin in as little as 20 minutes, 22 minutes, 25 minutes, 30 minutes, 35 minutes, 40 minutes, 47 minutes, 52 minutes, 58 minutes, or an hour after administration of the at least one heparan sulfate inhibitor and the at least one CXCR4 antagonist.

In some instances, the apheresis procedure can begin in as little as 15 minutes after administration of the at least one heparan sulfate antagonist and the at least one CXCR2 agonist. In some embodiments, the apheresis procedure can begin in as little as 20 minutes, 22 minutes, 25 minutes, 30 minutes, 35 minutes, 40 minutes, 47 minutes, 52 minutes, 58 minutes, or an hour after administration of the at least one heparan sulfate inhibitor and the at least one CXCR2 agonist.

In some instances, the apheresis procedure can begin in as little as 15 minutes after administration of the at least one heparan sulfate antagonist and G-CSF. In some embodiments, the apheresis procedure can begin in as little as 20 minutes, 22 minutes, 25 minutes, 30 minutes, 35 minutes, 40 minutes, 47 minutes, 52 minutes, 58 minutes, or an hour after administration of the at least one heparan sulfate inhibitor and G-CSF.

In some embodiments, administration of the at least one CXCR2 agonist and the at least one CXCR4 antagonist mobilizes an amount of circulating peripheral blood stem cells in the subject to harvest a cell dose of between about $1 \times 10^6$/kg body weight and $10 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight. In some embodiments, administration of the at least one CXCR2 agonist and the at least one CXCR4 antagonist mobilizes an amount of circulating peripheral blood stem cells in the subject to harvest a cell dose of between about $2 \times 10^6$/kg body weight and $8 \times 10^6$/kg body weight in a single apheresis session. In some embodiments, a single session of apheresis collects enough CD34+ peripheral blood stem cells for a cell dose of between about $2 \times 10^6$/kg and $8 \times 10^6$/kg of the recipient's body weight. In some embodiments, administration of the at least one CXCR2 agonist and the at least one CXCR4 antagonist mobilizes an amount of circulating peripheral blood stem cells in the subject to harvest a cell dose of between about $3 \times 10^6$/kg body weight and $6 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight.

In some embodiments, administration of the at least one heparan sulfate inhibitor and the at least one CXCR4 antagonist mobilizes an amount of circulating peripheral blood stem cells in the subject to harvest a cell dose of between about $1 \times 10^6$/kg body weight and $10 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight. In some embodiments, administration of the at least one heparan sulfate inhibitor and the at least one CXCR4 antagonist mobilizes an amount of circulating peripheral blood stem cells in the subject to harvest a cell dose of between about $2 \times 10^6$/kg body weight and $8 \times 10^6$/kg body weight in a single apheresis session. In some embodiments, a single session of apheresis collects enough CD34+ peripheral blood stem cells for a cell dose of between about $2 \times 10^6$/kg body weight and $8 \times 10^6$/kg body weight of the recipient's body weight. In some embodiments, administration of the at least one heparan sulfate inhibitor and the at least one CXCR4 antagonist mobilizes an amount of circulating peripheral blood stem cells in the subject to harvest a cell dose of between about $3 \times 10^6$/kg body weight and $6 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight.

In some embodiments, administration of the at least one heparan sulfate inhibitor and the at least one CXCR2 agonist mobilizes an amount of circulating peripheral blood stem cells in the subject to harvest a cell dose of between about $1 \times 10^6$/kg body weight and $10 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight. In some embodiments, administration of the at least one heparan sulfate inhibitor and the at least one CXCR2 agonist mobilizes an amount of circulating peripheral blood stem cells in the subject to harvest a cell dose of between about $2 \times 10^6$/kg body weight and $8 \times 10^6$/kg body weight in a single apheresis session. In some embodiments, a single session of apheresis collects enough CD34+ peripheral blood stem cells for a cell dose of between about $2 \times 10^6$/kg and $8 \times 10^6$/kg of the recipient's body weight. In some embodiments, administration of the at least one heparan sulfate inhibitor and the at least one CXCR2 agonist mobilizes an amount of circulating peripheral blood stem cells in the subject to harvest a cell dose of between about $3 \times 10^6$/kg body weight and $6 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight.

In some embodiments, administration of the at least one heparan sulfate inhibitor and G-CSF mobilizes an amount of circulating peripheral blood stem cells in the subject to harvest a cell dose of between about $1 \times 10^6$/kg body weight and $10 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight. In some embodiments, administration of the at least one heparan sulfate inhibitor and G-CSF mobilizes an amount of circulating peripheral blood stem cells in the subject to harvest a cell dose of between about $2 \times 10^6$/kg body weight and $8 \times 10^6$/kg body weight in a single apheresis session. In some embodiments, a single session of apheresis collects enough CD34+ peripheral blood stem cells for a cell dose of between about $2 \times 10^6$/kg and $8 \times 10^6$/kg of the recipient's body weight. In some embodiments, administration of the at least one heparan sulfate inhibitor and G-CSF mobilizes an amount of circulating peripheral blood stem cells in the subject to harvest a cell dose of between about $3 \times 10^6$/kg body weight and $6 \times 10^6$/kg body weight in a single apheresis session. In some embodiments, a single session of apheresis collects enough CD34+ peripheral blood stem cells for a cell dose of between about $1 \times 10^6$/kg and $10 \times 10^6$/kg of the recipient's body weight.

Conditioning for Engraftment

Certain aspects of the present invention relate to methods of conditioning a subject for engraftment of transplanted hematopoietic stem cells and/or progenitor cells (e.g., peripheral blood stem cells, bone marrow stem cells, umbilical cord stem cells, gene-modified stem cells, etc.).

Generally, the methods of conditioning a subject for engraftment of transplanted stem cells utilize one or more stem cell mobilization agent described herein. In some embodiments, the disclosure relates to methods of conditioning a subject for engraftment of transplanted peripheral blood stem cells utilizing the hematopoietic stem cell mobilization agents described herein. In some embodiments, the disclosure relates to methods of conditioning a subject for engraftment of transplanted bone marrow stem cells utilizing the hematopoietic stem cell mobilization agents described herein. In some embodiments, the disclosure relates to methods of conditioning a subject for engraftment of transplanted umbilical cord stem cells utilizing the hematopoietic stem cell mobilization agents described herein. In some embodiments, the disclosure relates to methods of conditioning a subject for engraftment of transplanted genetically modified stem utilizing the hematopoietic stem cell mobilization agents described herein. In some embodiments, the disclosure relates to methods of conditioning a subject for engraftment of a transplanted stem cell population comprising a mixture of stem cells selected from the group consisting of peripheral blood stem cells, bone marrow stem cells, peripheral blood stem cells, and genetically-modified stem cells, utilizing the hematopoietic stem cell mobilization agents described herein.

In some aspects, the disclosure provides methods of conditioning a subject for engraftment of transplanted stem cells comprises administering to a subject a stem cell and/or progenitor cell mobilization agent selected from the group consisting of at least one heparan sulfate inhibitor, at least one CXCR2 agonist, and at least one CXCR4 antagonist in an amount effective to deplete cells (e.g., stem cells and/or progenitor cells) from the subject's stem cell niche for subsequent engraftment in the subject's stem cell niche of transplanted stem cells, thereby conditioning the subject for engraftment of transplanted stem cells.

In one aspect, a method of conditioning a subject for engraftment of transplanted stem cells comprises administering to a subject at least one CXCR2 agonist in an amount effective to deplete stem cells and/or progenitor from the subject's stem cell niche for subsequent engraftment in the subject's stem cell niche of transplanted stem cells, thereby conditioning the subject for engraftment of transplanted stem cells.

In another aspect, a method of conditioning a subject for engraftment of transplanted stem cells comprises administering to a subject at least one CXCR4 antagonist in an amount effective to deplete stem cells and/or progenitor cells from the subject's stem cell niche for subsequent engraftment in the subject's stem cell niche of transplanted stem cells, thereby conditioning the subject for engraftment of transplanted stem cells.

In an aspect, a method of conditioning a subject for engraftment of transplanted stem cells comprises administering to a subject at least one heparan sulfate inhibitor in an amount effective to deplete stem cells and/or progenitor cells from the subject's stem cell niche for subsequent engraftment in the subject's stem cell niche of transplanted stem cells, thereby conditioning the subject for engraftment of transplanted stem cells.

In yet another aspect, a method of conditioning a subject for engraftment of transplanted stem cells, comprising administering to a subject Gro-beta or an analog or derivative thereof, in an amount effective to deplete stem cells from the subject's stem cell niche for subsequent engraftment in the subject's stem cell niche of transplanted stem cells, thereby conditioning the subject for engraftment of transplanted stem cells.

In still another aspect, a method of conditioning a subject for engraftment of transplanted stem cells comprises administering to a subject Gro-betaΔ4 or an analog or derivative thereof, in an amount effective to deplete stem cells from the subject's stem cell niche for subsequent engraftment in the subject's stem cell niche of transplanted stem cells, thereby conditioning the subject for engraftment of transplanted stem cells.

In yet still another aspect, the disclosure provides a method of conditioning a subject for engraftment of transplanted stem cells, comprising administering to a subject Plerixafor or an analog or derivative thereof, in an amount effective to deplete stem cells from the subject's stem cell niche for subsequent engraftment in the subject's stem cell niche of transplanted stem cells, thereby conditioning the subject for engraftment of transplanted stem cells.

In other aspects, a method of conditioning a subject for engraftment of transplanted stem cells comprises administering to a Subject Mozobil® or an analog or derivative thereof, in an amount effective to deplete stem cells from the subject's stem cell niche for subsequent engraftment in the subject's stem cell niche of transplanted stem cells, thereby conditioning the subject for engraftment of transplanted peripheral blood stem cells.

In certain aspects, a method of conditioning a subject for engraftment of transplanted stem cells comprises administering to a subject at least one CXCR2 agonist and at least one CXCR4 antagonist in amounts effective to deplete stem cells from the subject's stem cell niche for subsequent engraftment in the subject's stem cell niche of transplanted stem cells, thereby conditioning the subject for engraftment of transplanted stem cells.

In certain aspects, a method of conditioning a subject for engraftment of transplanted stem cells comprises administering to a subject at least one heparan sulfate inhibitor and at least one CXCR4 antagonist in amounts effective to deplete stem cells from the subject's stem cell niche for subsequent engraftment in the subject's stem cell niche of transplanted stem cells, thereby conditioning the subject for engraftment of transplanted stem cells.

In certain aspects, a method of conditioning a subject for engraftment of transplanted stem cells comprises administering to a subject at least one heparan sulfate inhibitor and at least one CXCR2 agonist in amounts effective to deplete stem cells from the subject's stem cell niche for subsequent engraftment in the subject's stem cell niche of transplanted stem cells, thereby conditioning the subject for engraftment of transplanted stem cells.

In certain aspects, a method of conditioning a subject for engraftment of transplanted stem cells comprises administering to a subject at least one heparan sulfate inhibitor and G-CSF in amounts effective to deplete stem cells from the subject's stem cell niche for subsequent engraftment in the subject's stem cell niche of transplanted stem cells, thereby conditioning the subject for engraftment of transplanted stem cells.

In certain aspects, a method of conditioning a subject for engraftment of transplanted stem cells comprises administering to a subject a combination of two or more stem cell mobilization agents selected from the group consisting of at least one heparan sulfate inhibitor, at least one CXCR4 antagonist, at least one CXCR2 agonist, and G-CSF in amounts effective to deplete stem cells from the subject's stem cell niche for subsequent engraftment in the subject's stem cell niche of transplanted stem cells, thereby conditioning the subject for engraftment of transplanted stem cells.

In some embodiments, the depleted stem cells and/or progenitor cells comprise hematopoietic stem cells and/or progenitor cells. In some embodiments, the stem cell niche comprises bone marrow. In some embodiments, the transplanted stem cells comprise peripheral blood stem cells. In some embodiments, the transplanted stem cells comprise harvested mobilized peripheral blood stem cells (e.g., CD34$^+$ and/or CD133$^+$). In some embodiments, the transplanted stem cells comprise peripheral blood stem cells and/or progenitor cells. In some embodiments, the transplanted stem cells comprise harvested mobilized peripheral blood stem cells and/or progenitor cells (e.g., CD34$^+$ and/or CD133$^+$). In some embodiments, the transplanted stem cells comprise umbilical cord stem cells and/or progenitor cells. In some embodiments, the transplanted stem cells comprise bone marrow stem cells and/or progenitor cells. In some embodiments, the transplanted stem cells comprise genetically-modified stem cells and/or progenitor cells.

Aspects of the methods disclosed herein (e.g., methods of mobilizing hematopoietic stem cells and/or progenitor cells) include conditioning a subject in need of a peripheral blood stem cell transplantation for engraftment of transplanted peripheral blood stem cells. As used herein "engrafting" and "engraftment" of a stem cell, including an expanded hematopoietic stem cell, means placing the stem cell into an animal, e.g., by injection, wherein the stem cell persists in vivo. This can be readily measured by the ability of the hematopoietic stem cell, for example, to contribute to the ongoing blood cell formation. As used herein "conditioning a subject for engraftment", "vacating the stem cell niche", and creating a "niche vacancy" are used interchangeably to refer to the process of depleting the amount of cells (e.g., hematopoietic stem cells and/or progenitor cells) in a subject's stem cell niche (e.g., bone marrow) for subsequent engraftment in the stem cell niche of healthy transplanted stem cells (e.g., peripheral blood stem cells, bone marrow stem cells, umbilical cord stem cells, genetically modified stem cells, minimally manipulated stem cells, etc.). A "niche vacating agent" refers to an agent that creates a "niche vacancy." It should be appreciated that in contexts in which a mobilization agent described herein (e.g., a hematopoietic stem cell and/or progenitor cell mobilization agent) is used to condition a subject for subsequent engraftment of transplanted stem cells the mobilization agent is also referred to as a niche vacating agent. The disclosure contemplates that the agents described herein (e.g., mobilization and/or niche vacating agents can be used to decrease the amounts of hematopoietic stem cells, CMPs, GMPs, MEPs, and/or CLPs from a stem cell niche (e.g., bone marrow). The disclosure contemplates any conditioning method which would be appropriate in the course of a particular subject's treatment, as well as any stem cell source which would be a desirable source for transplantation.

In some embodiments, conditioning the subject comprises administering to the subject a combination of at least two niche vacating agents selected from the group consisting of at least one CXCR2 agonist, at least one CXCR4 antagonist, at least one heparan sulfate inhibitor in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject a combination of at least two niche vacating agents selected from the group consisting of at least one CXCR2 agonist, at least one CXCR4 antagonist, at least one heparan sulfate inhibitor, and G-CSF in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject at least one CXCR2 agonist and at least one CXCR4 antagonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject at least one heparan sulfate inhibitor and at least one CXCR4 antagonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject at least one heparan sulfate inhibitor and at least one CXCR2 agonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject at least one heparan sulfate inhibitor and G-CSF in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject a composition comprising at least one CXCR2 agonist and at least one CXCR4 antagonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject a composition comprising at least one heparan sulfate inhibitor and at least one CXCR4 antagonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject a composition comprising at least one heparan sulfate inhibitor and at least one CXCR2 agonist in amounts effective to deplete stem cells and/or progenitor cells in the conditioned subject's stem cell niche for subsequent engraftment in the conditioned subject's stem cell niche of transplanted stem cells.

In some embodiments, conditioning the subject comprises administering to the subject a composition comprising at least one heparan sulfate inhibitor and G-CSF in amounts effective to deplete stem cells and/or progenitor cells in the conditioned subject's stem cell niche for subsequent engraftment in the conditioned subject's stem cell niche of transplanted stem cells.

In some embodiments, the depleted stem cells and/or progenitor cells comprise hematopoietic stem cells. In some embodiments, the stem cell niche comprises bone marrow.

In some embodiments, conditioning the subject comprises administering to the subject chemotherapy or radiation therapy to kill any remaining cancerous cells in the subject's bone marrow niche and make room for healthy peripheral blood stem cells to be transplanted and engrafted into the subject's bone marrow niche. Such conditioning is referred to herein as "toxic conditioning" because of the toxic systemic effects caused by the chemotherapy or radiotherapy, which some patients, particularly those undergoing treatments for non-malignant hematological diseases are unable or unwilling to tolerate.

Conventional methods of conditioning a patient for engraftment typically involve total body irradiation and high dose chemotherapy, which are toxic and undesirable for patients who do not suffer from a malignancy requiring irradiation or high dose chemotherapy as part of the treatment plan (e.g., HIV and other immunodeficiencies).

In contrast to the toxic conditioning typically performed by administering to a subject G-CSF in combination with chemotherapy or radiotherapy, the methods described herein employing at least one CXCR2 agonist and at least one CXCR4 antagonist as mobilization agents are capable of conditioning a subject for engraftment without chemotherapy or radiotherapy and therefore permit non-toxic conditioning. In some embodiments, the methods described herein employ at least one heparan sulfate inhibitor and at least one CXCR4 antagonist as mobilization agents that are capable of conditioning a subject for engraftment without chemotherapy or radiotherapy, thereby permitting non-toxic conditioning. In some embodiments, the methods described herein employ at least one heparan sulfate inhibitor and at least one CXCR2 agonist as mobilization agents that are capable of conditioning a subject for engraftment without chemotherapy or radiotherapy, thereby permitting non-toxic conditioning.

In contrast to conventional cytotoxic methods of conditioning, the present invention provides non-cytotoxic methods of conditioning. In particular, the present inventors have surprisingly and unexpectedly demonstrated that hematopoietic stem cells and/or progenitor cells engrafted EXT-1 deficient animals in vivo in the absence of cytotoxic conditioning. Without wishing to be bound by theory, it is believed that inhibition of heparan sulfate proteoglyans in a subject, for example via EXT-1 inhibition or VCAM-1 inhibition, provides an effective alternative non-cytotoxic method for conditioning the subject for engraftment of hematopoietic stem cells and/or progenitor cells.

In an aspect, a method of conditioning a subject for engraftment of transplanted hematopoietic stem cells and/or progenitor cells in the absence of cytotoxic conditioning comprises administering to a subject an amount of an agent that inhibits the level or activity of effective to mobilize hematopoietic stem cells and/or progenitor cells in the subject, thereby conditioning the subject for engraftment of transplanted hematopoietic stem cells and/or progenitor cells in the absence of cytotoxic conditioning. In an aspect, a method of conditioning a subject for engraftment of transplanted hematopoietic stem cells and/or progenitor cells in the absence of cytotoxic conditioning comprises administering to a subject an amount of an agent that inhibits the level or activity of heparan sulfate proteoglycans effective to mobilize hematopoietic stem cells and/or progenitor cells in the subject, thereby conditioning the subject for engraftment of transplanted peripheral blood stem cells and/or progenitor cells in the absence of cytotoxic conditioning.

In some embodiments, the subject is conditioned for engraftment of transplanted hematopoietic stem cells and/or progenitor cells in the absence of cytotoxic conditioning. In some embodiments, the subject is conditioned for engraftment without chemotherapy. In some embodiments, the subject is conditioned for engraftment without radiation. In some embodiments, the subject is conditioned for engraftment without attenuating stromal cells. In some embodiments, the subject is conditioned for engraftment without administering G-CSF to the subject.

It should be appreciated that any of the conditioning methods described herein can also include transplanting stem cells (e.g., peripheral blood stem cells, e.g., CD34$^+$ peripheral blood stem cells or CD133$^+$ peripheral blood stem cells, bone marrow stem cells, umbilical cord stem cells, genetically modified stem cells) into the subject for engraftment of the transplanted cells.

Transplanting Mobilized HSPCs

Aspects of the invention (e.g., methods of mobilizing stem cells and/or progenitor cells) involve transplanting stem cells into a subject in need of such transplantation. The methods disclosed herein contemplate transplanting any kind of stem cell into a subject in need of such transplantation (e.g., peripheral blood stem cells, bone marrow stem cells, umbilical cord stem cells, genetically modified stem cells, etc.).

In some embodiments, the methods disclosed herein (e.g., methods of mobilizing hematopoietic stem cells) include transplanting the harvested peripheral blood stem cells into a subject in need of such transplantation.

Methods of Treatment

Certain aspects of the present invention relate to methods of treating diseases requiring transplantation of hematopoietic stem cells and/or progenitor cells. Hematopoietic stem cell and/or progenitor cell (HPSC) transplantation remains the gold standard curative therapy for a number of hematological disorders. Successful HPSC Transplantation, however, depends on the ability to mobilize sufficient HSPCs into circulation for their harvest and transplantation into patients, and the efficient evacuation of bone marrow niches for subsequent engraftment of the transplanted HPSCs to occur. Conventional methods of inducing mobilization and evacuating bone marrow niches for subsequent engraftment, however, suffer from several shortcomings. For example, current mobilization methods, such as G-CSF induction, are subject to mobilization resistance, which may compromise lifesaving therapy for some individuals. Similarly, current methods of conditioning a patient for engraftment typically involve total body irradiation and high dose chemotherapy, which are toxic and undesirable for patients who do not suffer from a malignancy requiring irradiation or high dose chemotherapy as part of the treatment plan (e.g., HIV and other immunodeficiencies). Accordingly, the methods described herein enhance the safety and efficacy of HPSC transplantation, for example by providing strong hematopoietic stem cell and/or progenitor cell mobilization even in situations in which mobilization resistance would otherwise result in poor mobilization (e.g., mobilopathy), and by providing a non-cytotoxic conditioning method that conditions a subject for enhanced engraftment of hematopoietic stem cells and/or progenitor cells in the absence of cytotoxic conditioning.

In an aspect, a method of treating a disease requiring transplantation of hematopoietic stem cells and/or progenitor cells in a subject in need of such treatment comprises: (a) administering to a subject an amount of an agent that inhibits the level or activity of effective to mobilize hematopoietic stem cells and/or progenitor cells in the subject, thereby conditioning the subject for engraftment of transplanted hematopoietic stem cells and/or progenitor cells in the absence of cytotoxic conditioning; and (b) transplanting hematopoietic stem cells and/or progenitor cells into the subject, wherein the transplanted hematopoietic stem cells engraft in the subject's bone marrow, thereby treating a disease requiring transplantation of hematopoietic stem cells and/or progenitor cells in the subject. In an aspect, a method of treating a disease requiring transplantation of hematopoietic stem cells and/or progenitor cells in a subject in need of such treatment, the method comprises: (a) administering to a subject an amount of an agent that inhibits the level or activity of heparan sulfate proteoglycans effective to mobilize hematopoietic stem cells and/or progenitor cells in the subject, thereby conditioning the subject for engraftment of transplanted hematopoietic stem cells and/or progenitor cells in the absence of cytotoxic conditioning; and (b) transplanting hematopoietic stem cells and/or progenitor cells into the subject, wherein the transplanted hematopoietic stem cells engraft in the subject's bone marrow, thereby treating a disease requiring transplantation of hematopoietic stem cells and/or progenitor cells in the subject.

An exemplary method of treating a disease requiring stem cell and/or progenitor cell transplantation in a subject in need of such treatment comprises: (a) administering to a stem cell and/or progenitor cell donor a combination of two or more stem cell and/or progenitor cell mobilization agents selected from the group consisting of at least one heparan sulfate inhibitor, at least one CXCR2 agonist and at least one CXCR4 antagonist in amounts effective to mobilize circulating stem cells and/or progenitor cells in the donor; and (b) transplanting the mobilized circulating stem cells and/or progenitor from the donor into a subject in need of a stem cell transplantation.

In some embodiments, a method of treating a disease requiring stem cell transplantation in a subject in need of such treatment comprises: (a) administering to a stem cell donor at least one CXCR2 agonist and at least one CXCR4 antagonist in amounts effective to mobilize circulating stem cells in the donor; and (b) transplanting the mobilized circulating stem cells from the donor into a subject in need of a stem cell transplantation.

In some embodiments, a method of treating a disease requiring stem cell transplantation in a subject in need of such treatment comprises: (a) administering to a stem cell donor at least one heparan sulfate inhibitor and at least one CXCR4 antagonist in amounts effective to mobilize circulating stem cells in the donor; and (b) transplanting the mobilized circulating stem cells from the donor into a subject in need of a stem cell transplantation.

In some embodiments, a method of treating a disease requiring stem cell transplantation in a subject in need of such treatment comprises: (a) administering to a stem cell donor at least one heparan sulfate inhibitor and at least one CXCR2 agonist in amounts effective to mobilize circulating stem cells in the donor; and (b) transplanting the mobilized circulating stein cells from the donor into a subject in need of a stem cell transplantation.

In some embodiments, a method of treating a disease requiring stem cell transplantation in a subject in need of such treatment comprises: (a) administering to a stein cell donor at least one heparan sulfate inhibitor and G-CSF in amounts effective to mobilize circulating stem cells in the donor; and (b) transplanting the mobilized circulating stem cells from the donor into a subject in need of a stem cell transplantation.

Another exemplary method of treating a disease requiring peripheral blood stem cell and/or progenitor cell transplantation in a subject in need of such treatment comprises: (a) administering to a peripheral blood stein cell and/or progenitor cell donor a combination of two or more stein cell and/or progenitor cell mobilization agents selected from the group consisting of at least one CXCR2 agonist and at least one CXCR4 antagonist in amounts effective to mobilize circulating peripheral blood stem cells in the donor; and (b) transplanting the mobilized circulating peripheral blood stem cells and/or progenitor cells from the donor into a subject in need of a peripheral blood stem cell and/or progenitor cell transplantation.

It is to be understood that the descriptions above with respect to harvesting, conditioning, and transplanting are equally applicable to the treatment method aspects described here.

In some embodiments, a method of treating a disease requiring stem cell transplantation includes administering to the subject a therapeutically effective amount of a conventional treatment for the hematological malignancy.

In some embodiments, a method of treating a disease requiring stem cell transplantation includes administering to the subject a therapeutically effective amount of a conventional treatment for the non-malignant disease.

In some embodiments, a method of treating a disease requiring peripheral blood stem cell transplantation includes administering to the subject a therapeutically effective amount of a conventional treatment for the hematological malignancy.

In some embodiments, a method of treating a disease requiring peripheral blood stem cell transplantation includes administering to the subject a therapeutically effective amount of a conventional treatment for the non-malignant disease.

In some embodiments, a method of treating a disease requiring peripheral blood stem cell transplantation includes administering to the subject a therapeutically effective amount of a conventional treatment for cardiac repair or a cardiac myopathy. Examples indications in which mobilized $CD34^+$ and/or $CD133^+$ cells can be used for cardiac repair include, but are not limited to, treating angina (e.g., refractory angina), improving cardiac function in myocardial ischemia (e.g., chronic myocardial ischemia), to name only a few.

As used herein, "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of, for example, a condition, disease, or disorder described herein, or delaying or slowing onset of a condition, disease, or disorder described herein, and an increased lifespan as compared to that expected in the absence of treatment.

It should be appreciated that in contrast to conventional methods which typically require separate administrations of a mobilization agent (e.g., G-CSF) and a cytotoxic conditioning method (e.g., chemotherapy or radiation), certain embodiments of the methods, compositions, and agents described herein allow for the dual mobilization of hematopoietic stem cell and/or progenitor cells and non-cytotoxic conditioning for subsequent engraftment of hematopoietic stem cell and/or progenitor cells via administration of a single agent. For example, when an agent described herein is administered to a subject for an autologous hematopoietic stem cell and/or progenitor cell transplantation; the agent effectively mobilizes hematopoietic stem cells and/or progenitor cells while conditioning the subject for engraftment of those cells once they are harvested (e.g., via apheresis).

As used herein, the term "administering," refers to the placement of an agent described herein (e.g., an agent that inhibits the level or activity of EXT-1 or an agent that inhibits the level or activity of heparan sulfate), for example formulated into a pharmaceutically acceptable composition according to techniques well known to the skilled artisan, into a subject by a method or route which results in delivery to a site of action. The agent that inhibits the level or activity of EXT-1, agent that inhibits the level or activity of heparan sulfate proteoglycans, or pharmaceutical composition comprising such agents can be administered by any appropriate route which results in an effective treatment in the subject.

The present invention contemplates treating any disease, disorder, condition, or complication associated with a disease, disorder, or condition, in which transplantation of hematopoietic stem cells and/or progenitor cells is desirable. In some embodiments, the disclosure provides methods of treating diseases requiring peripheral blood stem cell transplantation in a subject in need of such treatment. Examples of such diseases include hematological malignancies and non-malignant hematological diseases, for example.

In some embodiments, the disease is a hematological malignancy. Exemplary hematological malignancies which can be treated with the methods described herein include, but are not limited to, acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia. In some embodiments, the disease is a non-malignant disorder. Exemplary non-malignant diseases which can be treated with the methods described herein include, but are not limited to, myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome. The disclosure also contemplates the use of cells mobilized in accordance with the methods described herein for cardiac repair. For example, certain mobilized $CD34^+$ and/or $CD133^+$ cells may contribute to neovascularization and promote angiogenesis and reperfusion of ischemic tissue of damaged cardiac tissue. Methods of identifying subjects in need of such treatments are described herein. Other suitable methods of identifying such subjects are apparent to the skilled artisan.

Subjects

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, of a hematological malignancy. In addition, the methods described herein can be used to treat domesticated animals and/or pets. A subject can be male or female.

A subject can be one who has been previously diagnosed with or identified as suffering from or having a condition, disease, or disorder described herein in need of treatment (e.g., of a hematological malignancy or non-malignant disease described herein) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition, A "subject in need" of treatment for a particular condition can be a subject having that condition, diagnosed as having that condition, or at increased risk of developing that condition relative to a given reference population.

In some embodiments, the methods described herein comprise selecting a subject diagnosed with, suspected of having, or at risk of developing a hematological malignancy, for example a hematological malignancy described herein.

In some embodiments, the methods described herein comprise selecting a subject diagnosed with, suspected of having, or at risk of developing a non-malignant disease, for example a non-malignant disease described herein.

In some embodiments, the methods described herein comprise selecting a subject diagnosed with, suspected of having, or at risk of developing diabetes.

In some embodiments, the methods described herein comprise selecting a subject who exhibits poor mobilization in response to a mobilization regimen. For example, a subject who is administered a first mobilization regimen can be selected for administration of an agent described herein to enhance mobilization of hematopoietic stem cells and/or progenitor cells in the subject. The present invention contemplates enhancing mobilization in a subject who exhibits poor mobilization in response to any mobilization agent or regimen. In some embodiments, the subject exhibits poor mobilization in response to granulocyte colony-stimulating factor (G-CSF). In some embodiments, the subject exhibits stem cell and/or progenitor cell mobilopathy.

In some embodiments, the methods described herein further comprise selecting a subject for exhibiting poor mobilization in response to previous administration of a hematopoietic stem cell mobilizing agent. The work described herein demonstrates that administration of at least one CXCR2 agonist in combination with at least one CXCR4 antagonist is significantly more effective than administration of G-CSF alone, Plerixafor alone, or a combination of G-CSF and Plerixafor. Accordingly, in some embodiments, the methods described herein further comprise selecting a subject for exhibiting poor mobilization in response to administration of G-CSF alone. The work described herein further demonstrates that administration of at least one heparan sulfate inhibitor in combination with at least one CXCR4 antagonist is significantly more effective than administration of Plerixafor alone, and that administration of at least one heparan sulfate inhibitor in combination with G-CSF is significantly more effective than administration of G-CSF alone. Accordingly, in some embodiments, the methods described herein further comprise selecting a subject for exhibiting poor mobilization in response to administration of G-CSF alone. In some embodiments, the subject is selected for exhibiting poor mobilization in response to administration of Plerixafor alone. In some embodiments, the subject is selected for exhibiting poor mobilization in response to administration of a combination of G-CSF and Plerixafor.

In such embodiments, a subject may be selected for remobilization using at least one CXCR2 agonist and at least one CXCR4 antagonist according to the teachings described herein. In an exemplary embodiment, a method of selecting a subject who would benefit from hematopoietic stem cell remobilization using at least one CXCR2 agonist and at least one CXCR4 antagonist comprises identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using at least one CXCR2 agonist and at least one CXCR4 antagonist.

In such embodiments, a subject may be selected for remobilization using at least one heparan sulfate inhibitor and at least one CXCR4 antagonist according to the teachings described herein. In an exemplary embodiment, a method of selecting a subject who would benefit from hematopoietic stem cell remobilization using at least one heparan sulfate inhibitor and at least one CXCR4 antagonist comprises identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using at least one heparan sulfate inhibitor and at least one CXCR4 antagonist.

In such embodiments, a subject may be selected for remobilization using at least one heparan sulfate inhibitor and at least one CXCR2 agonist according to the teachings described herein. In an exemplary embodiment, a method of selecting a subject who would benefit from hematopoietic stem cell remobilization using at least one heparan sulfate inhibitor and at least one CXCR2 agonist comprises identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using at least one heparan sulfate inhibitor and at least one CXCR2 agonist.

In such embodiments, a subject may be selected for remobilization using at least one heparan sulfate inhibitor and G-CSF according to the teachings described herein. In an exemplary embodiment, a method of selecting a subject who would benefit from hematopoietic stem cell remobilization using at least one heparan sulfate inhibitor and G-CSF comprises identifying a subject who exhibits poor mobilization in response to administration of a mobilization agent or regimen selected from the group consisting of G-CSF and Plerixafor, wherein a subject who exhibits poor mobilization in response to administration of a mobilization agent or regimen selected from the group consisting of G-CSF and Plerixafor is a subject who would benefit from hematopoietic stem cell remobilization using at least one heparan sulfate inhibitor and G-CSF.

In some embodiments, the subject is a patient presenting with a hematological malignancy. Exemplary hematological malignancies include, but are not limited to, acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

In some embodiments, the methods described herein further comprise selecting a subject diagnosed with a hematological malignancy. A subject suffering from a disorder associated with a hematological malignancy can be selected based on the symptoms presented. For example a subject suffering from hematological malignancy may show symptoms of fatigue, malaise, breathlessness, weakness, excessive or easy bruising, bleeding gums or frequent nose bleeds, recurrent infections or fever, night sweats, weight loss, anorexia, swollen lymph nodes, lumps or abdominal distension due to enlarged abdominal organs, abdominal pain, bone pain, back pain, confusion, delirium, headaches, visual disturbances, fluid retention, decreased urination.

In some embodiments, the methods described herein further comprise selecting a subject at risk of developing a hematological malignancy. A subject at risk of developing a hematological malignancy can be selected based on a family history (e.g., a study of patients diagnosed with lymphoma during 1998-2001 indicated that there was an increased risk of non-Hodgkin's lymphoma for individuals having a positive family-history of any hematologic malignancy, and particularly of any lymphoma; see Mensah et al. Non-Hodgkin's lymphoma and family history of hematological malignancy. Am J Epidemiol. 2007 165(2):126-33) or based on the symptoms presented.

In some embodiments, the methods described herein further comprise selecting a subject suspected of having a hematological malignancy. A subject suspected of having a hematological malignancy can be selected based on family history, diagnostic testing (e.g., for a translocation associated with leukemia or lymphoma) or based on the symptoms presented or a combination thereof.

In some embodiments, the subject is a patient presenting with a non-malignant hematological disease. Exemplary non-malignant hematological diseases include, but are not limited to, myelofibrosis, myelodysplastic syndrome, amyloidosis, severe aplastic anemia, paroxysmal nocturnal hemoglobinuria, immune cytopenias, systemic sclerosis, rheumatoid arthritis, multiple sclerosis, systemic lupus erythematosus, Crohn's disease, chronic inflammatory demyelinating polyradiculoneuropathy, human immunodeficiency virus (HIV), Fanconi anemia, sickle cell disease, beta thalassemia major, Hurler's syndrome (MPS-IH), adrenoleukodystrophy, metachromatic leukodystrophy, familial erythrophagocytic lymphohistiocytosis and other histiocytic disorders, severe combined immunodeficiency (SCID), and Wiskott-Aldrich syndrome.

In some embodiments, the methods described herein further comprise selecting a subject diagnosed with a non-malignant hematological disease. A subject suffering from a disorder associated with a non-malignant hematological disease can be selected based on the symptoms presented. For example a subject suffering from sickle cell disease (e.g., sickle cell anemia) may show symptoms of periodic episodes of pain, swollen hands and feet, frequent infections, and delayed growth.

In some embodiments, the methods described herein further comprise selecting a subject at risk of developing a non-malignant hematological disease. A subject at risk of developing a non-malignant hematological disease can be selected based on family history (e.g., a child with a parent having the sickle trait may be at risk of developing or having sickle cell disease), origin (e.g., descendants from Africa, India and the Mediterranean may be at higher risk for developing sickle cell disease) a diagnostic test (e.g., a point mutation or mutations in the beta-globin gene can be used to screen for sickle cell diseases and/or thalassemia) or based on the symptoms presented.

In some embodiments, the methods described herein further comprise selecting a subject suspected of having a non-malignant hematological disease. A subject suspected of having a non-malignant hematological disease can be selected based on family history, diagnostic testing, or based on the symptoms presented or a combination thereof.

In some embodiments, the methods described herein further comprise selecting a subject in need of cardiac repair. A subject in need of cardiac repair can be selected based on history of damaged cardiac tissue, for example due to acute ischemic injury and/or a chronic cardiomyopathy.

Compositions

The disclosure contemplates compositions comprising the agents (e.g., hematopoietic stem cell and/or progenitor cell mobilization agents) described herein. In some aspects, the disclosure provides a composition comprising a least one CXCR2 agonist. In some aspects, the disclosure provides a composition comprising at least one CXCR4 antagonist. In some aspects, the disclosure provides a composition comprising at least one heparan sulfate inhibitor.

In some aspects, the disclosure provides a composition comprising at least one CXCR2 agonist and at least one CXCR4 antagonist. The compositions comprising the at least one CXCR2 agonist and the at least one CXCR4 antagonist can be used for any application involving hematopoietic stem cell mobilization and transplantation. In some embodiments, the composition is useful for mobilizing hematopoietic stem cells into peripheral blood. In some embodiments, the composition is useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of one or more of G-CSF alone, and Plerixafor. In some embodiments, the composition is useful for conditioning a subject for engraftment of transplanted peripheral blood stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, the disclosure provides a composition comprising at least one heparan sulfate inhibitor and at least one CXCR4 antagonist. The compositions comprising the at least one heparan sulfate inhibitor and the at least one CXCR4 antagonist can be used for any application involving hematopoietic stem cell mobilization and transplantation. In some embodiments, the composition is useful for mobilizing hematopoietic stem cells into peripheral blood. In some embodiments, the composition is Useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of G-CSF alone, or Plerixafor alone or in combination with G-CSF. In some embodiments, the composition is useful for conditioning a subject for engraftment of transplanted stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, the disclosure provides a composition comprising at least one heparan sulfate inhibitor and at least one CXCR2 agonist. The compositions comprising the at least one heparan sulfate inhibitor and the at least one CXCR2 agonist can be used for any application involving hematopoietic stem cell mobilization and transplantation. In some embodiments, the composition is useful for mobilizing hematopoietic stem cells into peripheral blood. In some embodiments, the composition is useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of G-CSF alone, or Plerixafor alone or in combination with G-CSF. In some embodiments, the composition is useful for conditioning a subject for engraftment of transplanted stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, the disclosure provides a composition comprising at least one heparan sulfate inhibitor and G-CSF. The compositions comprising the at least one heparan sulfate inhibitor and G-CSF can be used for any application involving hematopoietic stem cell mobilization and transplantation. In some embodiments, the composition is useful for mobilizing hematopoietic stem cells into peripheral blood. In some embodiments, the composition is useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of G-CSF alone, or Plerixafor alone or in combination with G-CSF. In some embodiments, the composition is useful for conditioning a subject for engraftment of transplanted stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, the disclosure provides a composition comprising at least one heparan sulfate inhibitor, at least one CXCR2 agonist, and at least one CXCR4 antagonist. The compositions comprising the at least one heparan sulfate inhibitor; at least one CXCR2 agonist, and at least one CXCR4 antagonist can be used for any application involving hematopoietic stem cell mobilization and transplantation. In some embodiments, the composition is useful for mobilizing hematopoietic stem cells into peripheral blood. In some embodiments, the composition is useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of G-CSF alone, or Plerixafor alone or in combination with G-CSF. In some embodiments, the composition is useful for conditioning a subject for engraftment of transplanted stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, the disclosure provides a composition comprising at least one heparan sulfate inhibitor, at least one CXCR2 agonist, at least one CXCR4 antagonist, and G-CSF. The compositions comprising the at least one heparan sulfate inhibitor, at least one CXCR2 agonist, at least one CXCR4 antagonist, and G-CSF can be used for any application involving hematopoietic stem cell mobilization and transplantation. In some embodiments, the composition is useful for mobilizing hematopoietic stem cells into peripheral blood. In some embodiments, the composition is useful for remobilizing hematopoietic stem cells in subjects who respond poorly to, or fail to mobilize in response to, other mobilization treatments. In some embodiments, the composition is useful for remobilizing hematopoietic stem cells in subjects who exhibit poor mobilization in response to administration of G-CSF alone, or Plerixafor alone or in combination with G-CSF. In some embodiments, the composition is useful for conditioning a subject for engraftment of transplanted stem cells. In some embodiments, the composition is useful for rapid mobilization of stem cells from the stem cell niche into peripheral blood. In some embodiments, the composition mobilizes stem cells from the stem cell niche into peripheral blood in as little as 15 minutes. In some embodiments, the composition is useful for rapid mobilization of hematopoietic stem cells from the bone marrow niche into peripheral blood. In some embodiments, the composition mobilizes hematopoietic stem cells from the bone marrow niche into peripheral blood in as little as 15 minutes.

In some aspects, a composition comprises at least one agent that inhibits the level or activity of EXT1 and at least one niche vacating agent described herein. In some aspects, a composition comprises at least one agent that inhibits the level or activity of heparan sulfate proteoglycans (e.g., a heparan sulfate inhibitor) and at least one niche vacating agent described herein. In some aspects, a composition comprises at least one agent that inhibits the level or activity of EXT1 and at least one agent that inhibits the level or activity of heparan sulfate proteoglycans. In some aspects, a composition comprises at least one agent that inhibits the level or activity of EXT1 and a cytokine described herein. In some embodiments, a composition comprises at least one agent that inhibits the level or activity of heparan sulfate proteoglycans and a cytokine described herein. In some embodiments, a composition comprises at least one agent that inhibits the level or activity of EXT1 and at least one of a CXCR2 agonist, a CXCR4 antagonist, and G-CSF. In some embodiments, a composition comprises at least one agent that inhibits the level or activity of EXT1 and at least two of a CXCR2 agonist, a CXCR4 antagonist, and G-CSF. In some embodiments, a composition comprises at least one agent that inhibits the level or activity of EXT1, a CXCR2 agonist, a CXCR4 antagonist, and G-CSF.

Identification Methods

The disclosure contemplates various methods of identifying stem cell mobilizing agents (e.g., hematopoietic stem cell mobilizing agents) and conditioning agents.

In some aspects, a method of identifying a hematopoietic stem cell mobilizing agent comprises: (a) providing a CXCR2 protein or functional fragment thereof; (b) providing a test agent; and (c) assaying the ability of the test agent to agonize the CXCR2 protein or functional fragment thereof, wherein a test agent that agonizes the CXCR2 protein or functional fragment thereof is a candidate hematopoietic stem cell mobilizing agent.

In some aspects, a method of identifying a hematopoietic stem cell mobilizing agent comprises: (a) providing a CXCR4 protein or functional fragment thereof; (b) providing a CXCR4 binding partner; (c) providing a test agent; and (d) assaying the ability of the test agent to inhibit binding of the CXCR4 binding partner to the CXCR4 protein or functional fragment thereof, wherein a test agent that inhibits binding of the CXCR4 binding partner to the CXCR4 protein or functional fragment thereof is a candidate hematopoietic stem cell mobilizing agent.

In some aspects, a method of identifying a hematopoietic stem cell mobilizing agent comprises: (a) providing a heparan sulfate proteoglycan; (b) heparan sulfate proteoglycan binding partner; (c) providing a test agent; (c) and assaying the ability of the test agent to inhibit binding of heparan sulfate proteoglycan to the heparan sulfate proteoglycan binding partner, wherein a test agent that inhibits binding of heparan sulfate proteoglycan to the heparan sulfate proteoglycan binding partner is a candidate hematopoietic stem cell mobilizing agent.

In some aspects, a method of identifying a hematopoietic stem cell mobilizing agent comprises: (a) providing a test agent; and (b) assessing the ability of the test agent to emulate the hematopoietic stem cell mobilizing effect of at least one CXCR2 agonist and at least one CXCR4 antagonist.

In some aspects, a method of identifying a hematopoietic stem cell mobilizing agent comprises: (a) providing a test agent; and (b) assessing the ability of the test agent to emulate the hematopoietic stem cell mobilizing effect of at least one heparan sulfate antagonist and at least one CXCR4 antagonist.

In some aspects, a method of identifying a hematopoietic stem cell mobilizing agent comprises: (a) providing a test agent; and (b) assessing the ability of the test agent to emulate the hematopoietic stem cell mobilizing effect of at least one heparan sulfate antagonist and at least one CXCR2 agonist.

In some aspects, a method of identifying a hematopoietic stem cell mobilizing agent comprises: (a) providing a test agent; and (b) assessing the ability of the test agent to emulate the hematopoietic stem cell mobilizing effect of at least one heparan sulfate antagonist and G-CSF.

Candidate hematopoietic stem cell mobilizing agents identified in accordance with the methods described herein can be further assessed for their ability to condition subjects for enhanced engraftment of transplanted mobilized stem cells.

Kits

An agent described herein can be provided in a kit. The kit includes (a) the agent, e.g., a composition that includes the agent, and (b) informational material. The informational material can be descriptive, instructional, marketing or other material that relates to the methods described herein and/or the use of the agent for the methods described herein. For example, the informational material describes methods for administering the agent to a subject for mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In one embodiment, the informational material can include instructions to administer the agent in a suitable manner, e.g., in a suitable dose, dosage form, or mode of administration (e.g., a dose, dosage form, or mode of administration described herein). In another embodiment, the informational material can include instructions for selecting a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the modulator and/or its use in the methods described herein. Of course, the informational material can also be provided in any combination of formats.

In addition to the agent or the composition of the kit can include other ingredients, such as a solvent or buffer, a stabilizer or a preservative, and/or a second agent for treating a condition or disorder described herein, e.g. a disease requiring transplantation of mobilized peripheral blood stem cells. Alternatively, the other ingredients can be included in the kit, but in different compositions or containers than the agent. In such embodiments, the kit can include instructions for admixing the agent and the other ingredients, or for using the modulator together with the other ingredients.

The agent can be provided in any form, e.g., liquid, dried or lyophilized form. It is preferred that the agent be substantially pure and/or sterile. When the agent is provided in a liquid solution, the liquid solution preferably is an aqueous solution, with a sterile aqueous solution being preferred. When the agent is provided as a dried form, reconstitution generally is by the addition of a suitable solvent. The solvent, e.g., sterile water or buffer, can optionally be provided in the kit.

The kit can include one or more containers for the composition containing the agent. In some embodiments, the kit contains separate containers, dividers or compartments for the agent (e.g., in a composition) and informational material. For example, the agent (e.g., in a composition) can be contained in a bottle, vial, or syringe, and the informational material can be contained in a plastic sleeve or packet. In other embodiments, the separate elements of the kit are contained within a single, undivided container. For example, the agent (e.g., in a composition) is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agent (e.g., in a composition). For example, the kit includes a plurality of syringes, ampules, foil packets, or blister packs, each containing a single unit dose of the agent. The containers of the kits can be air tight and/or waterproof.

The agent (e.g., in a composition) can be administered to a subject, e.g., an adult subject, e.g., a subject suffering from a disease requiring transplantation of mobilized peripheral blood stem cells (e.g., a hematological malignancy). The method can include evaluating a subject, e.g., to obtain a complete blood count, and thereby identifying a subject as having a hematological malignancy. Methods of obtaining a complete blood count are known to the skilled artisan.

In some aspects, a kit comprises; (a) a combination of two or more stem cell mobilization agents selected from the group consisting of (i) at least one heparan sulfate inhibitor, (ii) at least one CXCR2 agonist, and (iii) at least one CXCR4 antagonist; and (c) instructions for the administrating the combination of the two or more stem mobilization agents selected from (i), (ii) and (iii) to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one CXCR2 agonist; (b) at least one CXCR4 antagonist; and (c) instructions for the administrating the at least one CXCR2 agonist and the at least one CXCR4 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one heparan sulfate inhibitor; (b) at least one CXCR4 antagonist; and (c) instructions for the administrating the at least one heparan sulfate inhibitor and the at least one CXCR4 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one heparan sulfate inhibitor; (b) at least one CXCR2 antagonist; and (c) instructions for the administrating the at least one heparan sulfate inhibitor and the at least one CXCR2 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one heparan sulfate inhibitor; (b) G-CSF; and (c) instructions for the administrating the at least one heparan sulfate inhibitor and the G-CSF to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one agent that inhibits the level or activity of EXT1; (b) at least one CXCR4 antagonist; and (c) instructions for the administrating the at least one heparan sulfate inhibitor and the at least one CXCR4 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

In some aspects, a kit comprises: (a) at least one agent that inhibits the level or activity of EXT1; (b) at least one CXCR2 antagonist; and (c) instructions for the administrating the at least one heparan sulfate inhibitor and the at least one CXCR2 antagonist to a subject for one or more of (i) mobilizing hematopoietic stem cells in the subject; (ii) remobilizing hematopoietic stem cells in a subject who exhibited poor mobilization in response to administration of G-CSF alone, Plerixafor, or a combination of G-CSF and Plerixafor; (iii) conditioning a subject for engraftment of transplanted peripheral blood stem cells; and (iv) treating a disease requiring peripheral blood stem cell transplantation in the subject.

Agents

The present invention contemplates the use of various agents in connection with the methods and compositions described herein. In particular, the work described herein demonstrates that agents that inhibit the level or activity of heparan sulfate proteoglycans, for example by inhibiting the level or activity of EXT-1, can be used in methods and compositions for mobilizing hematopoietic stem cells and/or progenitor cells, and are particularly effective at mobilizing hematopoietic stem cells and/or progenitor cells in situations where mobilization resistance would otherwise result in poor mobilization, as well as in non-cytotoxic methods of conditioning a subject for engraftment without requiring cytotoxic conditioning. As will be appreciated by those skilled in the art, the foregoing agents can be used in various methods of treatment of diseases which require transplantation of hematopoietic stem cells and/or progenitor cells.

The methods and compositions described herein contemplate administering "effective amounts" of an agent described herein. As used herein, "an amount effective to," "effective amount", or "therapeutically effective amount" are used interchangeably to mean an amount of the agent which is effective to mobilize hematopoietic stem cells and/or progenitor cells to egress from a cell niche of the subject, for example from the subject's bone marrow into the subject's peripheral blood. Determination of an effective amount is well within the capability of those skilled in the art. Generally, an effective amount can vary with the subject's history, age, condition, sex, as well as the severity and type of the medical condition in the subject, and administration of other agents that inhibit pathological processes in the hematological malignancy or non-malignant disorder.

In some contexts, administration of an agent described herein decreases an amount of hematopoietic stem cells and/or progenitor cells in a cell niche of the subject (e.g., bone marrow). As used herein, the terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In an embodiment, the decrease includes a 100% decrease (e.g. absent level as compared to a reference sample), or any decrease between 10-100% as compared to a reference level. In some embodiments, administration of an agent that inhibits the level or activity of EXT-1 decreases an amount of hematopoietic stem cells and/or progenitor cells in the subject's bone marrow by at least about 5%, 10%, 20%, 30%, 40%, 50%, 60%, 70%, 80, 90%, or as much as 100% as compared to a reference level. In some embodiments, administration of the agent that inhibits the level or activity of heparan sulfate proteoglycans decreases an amount of hematopoietic stem cells and/or progenitor cells in the subject's bone marrow by at least about 5%, 10%, 20%, 30%, 40%, 50%, 60%, 70%, 80, 90%, or as much as 100% as compared to a reference level.

In some contexts, administration of an agent described herein increases an amount of hematopoietic stem cells and/or progenitor cells in the subject's peripheral blood. The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In some embodiments, administration of an agent that inhibits the level or activity of EXT-1 increases an amount of hematopoietic stem cells and/or progenitor cells in the subject's peripheral blood by at least about 5%, 10%, 20%, 30%, 40%, 50%, 60%, 70%, 80, 90%, or as much as 100% as compared to a reference level. In some embodiments, administration of an agent that inhibits the level or activity of EXT-1 increases an amount of hematopoietic stem cells and/or progenitor cells in the subject's peripheral blood by at least about 1.1-fold, 1.2-fold, 1.3-fold, 1.4-fold, 1.5-fold, 2-fold, 3-fold, 4-fold, 5-fold, or at least about a 10-fold or greater as compared to a reference level. In some embodiments, administration of the agent that inhibits the level or activity of heparan sulfate proteoglycans increases an amount of hematopoietic stem cells and/or progenitor cells in the subject's peripheral blood by at least about 5%, 10%, 20%, 30%, 40%, 50%, 60%, 70%, 80, 90%, or as much as 100% as compared to a reference level. In some embodiments, administration of the agent that inhibits the level or activity of heparan sulfate proteoglycans increases an amount of hematopoietic stem cells and/or progenitor cells in the subject's peripheral blood by at least about 1.1-fold, 1.2-fold, 1.3-fold, 1.4-fold, 1.5-fold, 2-fold, 3-fold, 4-fold, 5-fold, or at least about a 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The present invention contemplates inhibiting the level or activity of any heparan sulfate proteoglycan which is involved in retention of hematopoietic stem cells and/or progenitor cells in a cell niche (e.g., bone marrow stem cell niche). In some embodiments, the agent inhibits the level or activity of heparan sulfate proteoglycans expressed in mesenchymal cells. In some embodiments, the agent inhibits the level or activity of heparan sulfate proteoglycans expressed in bone marrow mesenchymal cells. In some embodiments, the agent inhibits the level or activity of heparan sulfate proteoglycans expressed in Mx1+ skeletal stem cells and/or progenitor cells.

The present invention also contemplates inhibiting the level or activity of heparan sulfate proteoglycans in any way that interferes with retention of hematopoietic stem cells and/or progenitor cells in a cell niche (e.g., bone marrow). It is to be understood that the agent that inhibits the level or activity of heparan sulfate proteoglycans can also be referred to as a heparan sulfate inhibitor. As used herein, "heparan sulfate inhibitor" refers to any agent that is capable of competing with the level and/or activity of endogenous heparan sulfate, for example heparan sulfate proteoglycan interaction with VCAM-1 in retaining stem and/or progenitor cells in bone marrow.

In some embodiments, the heparan sulfate inhibitor comprises an agent that decreases the level or activity of EXT-1. Exemplary agents that decrease the level or activity of EXT-1 include, but are not limited to shRNA, miRNA, siRNA, microRNA, small molecules, antisense oligonucleotides, and anti-EXT-1 antibodies. shRNAs directed against EXT-1 are described by Reijmers et al. (Blood. 2010; 115(3):601-604). Anti-EXT-1 antibodies are commercially available (e.g., from Abcam).

Exemplary small molecule inhibitors of heparan sulfate are described by Garud et al. (J Biol Chem. 2008; 283(43): 28881-28887). In some embodiments, the heparan sulfate inhibitor comprises a glycosyltransferase inhibitor. In some embodiments, the heparan sulfate inhibitor is a competitive inhibitor of endogenous heparan sulfate. Examples of such inhibitors include heparin sulfate, protamine sulfate, Surfen, and analogs or derivatives thereof. Examples of molecules exhibiting similarity to heparin include, but are not limited to heparin tetrasaccharide, pentosan polysulfate, phosphomannopentanose sulfate, and selectively chemically O-desulphated heparin. Heparin derivatives which can be used as the at least one heparan sulfate inhibitor are described in U.S. Pat. No. 4,816,446, incorporated by reference herein. Polysulfated heparines which can be used at the at least one heparan sulfate inhibitor are described in European Patent No. EP0322659A1, incorporated by reference herein.

In some embodiments, the at least one heparan sulfate inhibitor is an agent that decreases the level or activity of VCAM-1. Exemplary agents that decrease the level or activity of VCAM-1 include, but are not limited to, shRNA, miRNA, siRNA, microRNA, small molecules, antisense oligonucleotides, and anti-VCAM-1 antibodies. In some embodiments, an agent that decreases the level or activity of VCAM-1 is Symbiopolyol. In some embodiments, an agent that decreases the level or activity of VCAM-1 is a proteasome inhibitor. In some embodiments, an agent that decreases the level or activity of VCAM-1 is probucol, as well as succinic acid esters of probucol as described in European Patent No. EP146639, incorporated herein by reference in its entirety. In some embodiments, an agent that decreases the level or activity of VCAM-1 is nitric oxide. Exemplary small molecule inhibitors of VCAM-1 include thioketals and thioethers described in PCT International Application Publication No. WO/2001/070757A2, the contents of which are incorporated herein by reference. Additional compounds and methods for the inhibition of expression of VCAM-1 are described in U.S. Pat. No. 6,147,250, the contents of which are incorporated by reference herein. Further compounds and methods of inhibiting VCAM-1 expression can be found in U.S. Pat. Nos. 6,828,447, 6,548, 699, 6,617,352, 6,660,914, and 7,189,870. Exemplary antisense oligos directed against human VCAM-1 RNA can be found in U.S. Pat. No. 5,596,090, incorporated herein by reference in its entirety.

The disclosure contemplates the use of at least one heparan sulfate inhibitor, at least one CXCR2 agonist and at least one CXCR4 antagonist, alone, or in combination, as stem cell and/or progenitor cell mobilization agents in the methods, compositions, and kits described herein. The disclosure contemplates the use of any agent that is capable of inhibiting heparan sulfate, agonizing CXCR2 or antagonizing CXCR4 and mobilizing stem cells. Exemplary types of agents that can be used as the at least one heparan sulfate inhibitor, the at least one CXCR2 agonist and the at least one CXCR4 antagonist in the methods, compositions, and kits described herein include small organic or inorganic molecules; saccharines; oligosaccharides; polysaccharides; a biological macromolecule selected from the group consisting of peptides, proteins, peptide analogs and derivatives; peptidomimetics; nucleic acids selected from the group consisting of siRNAs, shRNAs, antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments, the at least one CXCR2 agonist is the chemokine Gro-beta or an analog or derivative thereof, An exemplary form of Gro-beta is the human Gro-beta polypeptide (GenBank Accession: AAP13104). An exemplary Gro-beta analog or derivative is the desamino Gro-beta protein (also known as MIP-2alpha), which comprises the amino acid sequence of mature gro-S protein truncated at its N terminus between amino acid positions 2 and 8, as described in PCT International Application Publication WO/1994/029341, incorporated herein by reference in its entirety. Another Gro-beta analog or derivative is the dimeric modified Gro-beta protein described in U.S. Pat. No. 6,413,510, incorporated herein by reference in its entirety. Still another exemplary Gro-beta analog or derivative is SB-251353, a Gro-beta analog involved in directing movement of stem cells and other leukocytes, as described by Bensinger et al. (Bone Marrow Transplantation (2009), 43, 181-195, incorporated by reference herein).

In some embodiments, the at least one CXCR2 agonist is Gro-betaΔ4 or an analog or derivative thereof. In some embodiments, the at least one CXCR2 agonist is selected from the group consisting of Gro-beta or an analog or derivative thereof and Gro-betaΔ4 or an analog or derivative thereof.

In some embodiments, the at least one CXCR4 antagonist is Plerixafor or an analog or derivative thereof. In some embodiments, the at least one CXCR4 antagonist is Mozobil® or an analog or derivative thereof. In some embodiments, the at least one CXCR4 antagonist is selected from the group consisting of Plerixafor or an analog or derivative thereof and Mozobil® or an analog or derivative thereof. Exemplary analogs of Plerixafor include, but are not limited to, AMD11070, AMD3465, KRH-3955, T-140, and 4F-benzyol-TN14003, as described by De Clercq, E. (Pharmacol Ther. 2010 128(3):509-18, incorporated by reference herein in its entirety).

In some embodiments, the at least one CXCR2 agonist is Gro-beta or an analog or derivative thereof and the at least one CXCR4 antagonist is Plerixafor or an analog or derivative thereof.

In some embodiments, the at least one CXCR2 agonist is Gro-beta or an analog or derivative thereof and the at least one CXCR4 antagonist is Mozobil® or an analog or derivative thereof.

In some embodiments, the at least one CXCR2 agonist is selected from the group consisting of Gro-beta or an analog or derivative thereof and Gro-betaΔ4 or an analog or derivative thereof and the at least one CXCR4 antagonist is selected from the group consisting of Plerixafor or an analog or derivative thereof and Mozobil® or an analog or derivative thereof.

Any suitable route of administration can be employed to administer an agent described herein to a subject. For a comprehensive review on drug delivery strategies, see Ho et al., Curr. Opin. Mol. Ther. (1999), 1:336-3443; Groothuis et al., J. Neuro Virol. (1997), 3:387-400; and Jan, Drug Delivery Systems: Technologies and Commercial Opportunities, Decision Resources, 1998, content of all which is incorporate herein by reference.

The agents can be formulated in pharmaceutically acceptable compositions which comprise a therapeutically-effective amount of the agent, formulated together with one or more pharmaceutically acceptable carriers (additives) and/or diluents.

The formulations can conveniently be presented in unit dosage form and may be prepared by any of the methods well known in the art of pharmacy. Techniques, excipients and formulations generally are found in, e.g., Remington's Pharmaceutical Sciences, Mack Publishing Co., Easton, Pa. 1985, 17th edition, Nema et al., PDA J. Pharm. Sci. Tech. 1997 51: 166-171.

The agents described herein can be administered to a subject in combination with other pharmaceutically active agents. Exemplary pharmaceutically active agents include, but are not limited to, those found in *Harrison's Principles of Internal Medicine,* 13$^{th}$ Edition, Eds. T. R. Harrison et al. McGraw-Hill N.Y., NY; Physician's Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference. In some embodiments, the pharmaceutically active agent is a conventional treatment for a hematological malignancy. In some embodiments, the pharmaceutically active agent is a conventional treatment for a non-malignant disease. The skilled artisan will be able to select the appropriate conventional pharmaceutically active agent for treating any particular hematological malignancy or non-malignant disease using the references mentioned above based on their expertise, knowledge and experience.

In some embodiments, the pharmaceutically active agent is a hematopoietic stem cell mobilization agent. In some embodiments, the hematopoietic stem cell mobilization agent is a cytokine. Exemplary cytokines for use in connection with the agents described herein (e.g., heparan sulfate inhibitor) include, but are not limited to granulocyte colony-stimulating factor (G-CSF), granulocyte-macrophage colony-stimulating factor (GM-CSF), interleukin-3 (IL-3), and glycosylated or pegylated forms thereof.

In some embodiments, the hematopoietic stem cell mobilization agent is a chemotherapeutic agent (e.g., CY, Paclitaxel, Etoposide). In some embodiments, the hematopoietic stem cell mobilization agent is EPO. In some embodiments, the hematopoietic stem cell mobilization agent is stem cell factor. In some embodiments, the hematopoietic stem cell mobilization agent is TPO. In some embodiments, the hematopoietic stem cell mobilization agent is parathyroid hormone.

In some embodiments, the pharmaceutically active agent is a chemotherapeutic agent. Exemplary chemotherapeutic agents include, but are not limited to, vinblastine, doxorubicin, bleomycin, methotrexate, 5-fluorouracil, 6-thioguanine, cytarabine, cyclophosphamide and cisplatinum. Other suitable chemotherapeutic agents are apparent to the skilled artisan.

Some Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described herein. The term "comprises" means "includes." The abbreviation, "e.g." is derived from the Latin exempli gratia, and is used herein to indicate a non-limiting example. Thus, the abbreviation "e.g." is synonymous with the term "for example."

EXAMPLES

Example 1

Reducing the Toxicity of Conditioning to Lower the Barrier for Achieving a HSC Transplant Therapy for HIV/AIDS Hematopoietic stem cell (HSC) transplantation is the one known basis for apparent cure of HIV. The 'Berlin patient' in whom an allogeneic CCR5−/− hematopoietic graft after intensive chemotherapy provided a durable state of undetectable HIV, provides strong rationale for a stem cell based approach.[1] Recently, two additional patients treated with allogeneic transplantation were reported to have undectable HIV viral load at 8 and 17 months post-transplant. (Abstract THAA0101 XIX International AIDS Conference, Washington, D.C.; Jul. 22-27, 2012) In addition, genetically modified USC to enhance HIV resistance have been tested in clinical trials.[2] (and unreported Systemix sponsored multi-center trial, DTS as investigator) Multiple efforts to leverage emerging gene modification strategies such as TALENs and zinc-finger nucleases are focused on creating HIV resistant autologous HSC that provide greater opportunities for stem cell transplantation as a means of creating a HIV resistant immune system capable of targeting HIV reservoirs.[3] These approaches, if successful, could provide a means of durably controlling or eradicating HIV without life-long anti-retroviral therapy. Such a result would have enormous obvious benefit, but achieving that outcome requires considerable developments in transplantation to reduce the toxicity, complexity and cost.

Conditioning prior to transplant is typically achieved by administration of high doses of chemotherapy and/or in combination with radiation in order to deplete hematopoietic cells within the recipient marrow. These traditional methods of conditioning often preclude the use of HSC transplants in patients who do not have a life-threatening malignancy, significantly reducing the number of patients who could benefit from an HSC transplant. The development of non-myeloablative reduced conditioning regimens would greatly extend curative HSC transplantation to a broader spectrum of diseases, most notably HIV. Previous attempts to achieve HSC engraftment using non-myeloablative conditioning have demonstrated that selective targeting and elimination of HSCs without apparent systemic toxicity allows for almost complete replacement of the immune system. However, these approaches were either using a mouse specific antibody reagent[4] or were combined with low doses of irradiation.5 The use of AMD3100, a CXCR4 antagonist capable of causing HSC egress from the bone marrow, or repeated infusion of stem cells with no conditioning have achieved modest levels of chimerism, yet have not extended to clinical practice in part because of poor levels of engraftment[6]. Other strategies are needed. Given the success of transplant to date, the progress being made in gene modification technology and the daunting challenges of lifelong anti-retroviral chemotherapy, reducing the barrier to stem cell therapy for HIV/AIDS seems highly justifiable. The approach we discuss here can potentially result in more rapid movement of either gene modified autologous cells or allogeneic cells to more widespread clinical testing.

The issue of stem cell therapies for HIV is not new and indeed we and others conducted a series of pre-clinical and clinical studies in the past.[7-10] These were focused on whether HSC were infected with HIV (we found they were not;[7]) and whether retrovirally transduced cells bearing genetic constructs restricting HIV replication could be successfully transplanted into HIV infected individuals. In addition, we conducted a multi-center trial on the use of HSC transplantation in patients with AIDS-related lymphomas demonstrated that it could be accomplished and durably affect the underlying malignancy.[9] However, the toxicities would be prohibitive for a HIV infected individual without a malignancy. Finding novel means of accomplishing high efficiency engraftment of genetically modified or CCCR5−/− HSPC would innovate around a currently restricting barrier to the application of potentially curative approach.

The specific means by which we plan to accomplish the improvements in engraftment involve a number of novel discoveries and constructs taking advantage of a new discovery by the inventors of the role of the glycosyltransferase, EXT1, in HSPC retention in the bone marrow to test a novel, low cost, low toxicity means of vacating the bone marrow niche. These efforts to permit niche vacancy are all based on new agents or new biology and represent novel approaches that each has potential for clinical application. In particular, the efforts use many compounds which are already FDA approved for novel uses allowing for rapid translation of positive findings.

As a means to cross one critical barrier to the use of HSC transplant as a curative treatment modality for HIV/AIDS, toxicity conditioning, we continue to test reduced conditioning approaches to achieve HSC engraftment with minimal toxicity and damage to the HSC niche. Our methodology provides an opportunity for infused cells to successfully compete with endogenous stem cells to achieve engraftment. In particular, we will combine mechanistically distinct mobilization agents known to target different molecules implicated in HSC retention in the bone marrow that do not impair the niche, yet cause highly efficient mobilization.

This approach may then permit infused cells to compete with endogenous cells. We aim to provide a competitive advantage to infused cells without requiring the highly toxic, non-targeted conditioning regimens currently in practice. The work described herein establishes a proof-of-concept for novel conditioning strategies for HSC transplant recipients. Improved conditioning regimens will limit acute immune suppression and off-target tissue damage and potentially solve at least one of the issues limiting HSC transplantation for patients with non-malignant hematologic and immunologic disease, HIV/AIDS.

Example 2

Enhance Niche Vacancy without Niche Toxicity Through Manipulation of CXCR2 and CXCR4

Preclinical data suggests that CXCR2 agonists may be superior to current standard of care both in terms of the kinetics of action and the quality of cells that get mobilized. The goal of this project is to test existing GSK CXCR2 agonists, Gro-beta in combination with the CXCR4 inhibitor Mozobil®, and compare outcomes to current standard of care for mobilization, engraftment, and as non-toxic conditioning regimens. Animals will be treated with various combinations of G-CSF, Plerixafor (e.g., Mozobil®), Gro-beta or other mobilizing agents and tested for their ability to induce HSC mobilization. Cells mobilized will be analyzed for their in vitro & in vivo functional capacities and ability to enhance survival and hematopoietic recovery in irradiated mice. Cells will be characterized via functional assays, immunohistochemistry and transcriptomics to help define variations in mobilized stem cell populations.

The potential impact is identification of medicines that can increase significantly the number of patients eligible for HSC transplants, reduce the morbidity associated with G-CSF for both healthy and autologous donors, increase quality of life given anticipated reduction in donor time, and potentially enable increased use of HSC transplants as a life-saving medicine for patients with non-malignant diseases or those requiring gene therapy by reduced or non-toxic conditioning. This rapid mobilization strategy also has the potential for use in non-hematopoietic indications, as mobilized CD34+ cells are actively being explored in Phase III as a therapeutic for ischemic heart disease.

Hematopoietic stem cell (HSC) transplantation is currently the only curative treatment modality for a number of malignant hematologic diseases. Transplant related morbidity and mortality however remains high, and only a fraction of the patients that could benefit from an HSC transplant actually receive one. Reducing these inherent risks has the potential to greatly increase the numbers of patients transplanted each year.

Sources of HSC for transplantation include the bone marrow, umbilical cord blood, or mobilized peripheral blood. Under steady state conditions, HSC and HPC reside within the bone marrow niches, while the mature cells produced by these populations exit the marrow and enter the periphery. Based on observations that increased HPC were found in patients after chemotherapy, it became known that natural egress of HSC and HPC could be enhanced. The hematopoietic growth factor, granulocyte colony stimulating factor (G-CSF) is widely used clinically to mobilize HSC and HPC for transplantation. G-CSF-mobilized peripheral blood stem cells (PBSC) are associated with more rapid engraftment, shorter hospital stay ([1-4]), and in some circumstances, superior overall survival compared to bone marrow ([5]). Mobilized adult HSC and HPC are now widely used for autologous and allogeneic transplantation.

While successful, there remains significant medical need for improved Ham, mobilizers, as G-CSF regimens involve repeated subcutaneous injections that are often associated with morbidity from bone pain (an often severe and debilitating complication), nausea, headache, and fatigue ([6-9]). These can be lifestyle disruptive with a high percent of voluntary withdrawal in normal volunteers and is particularly distressing for patients who are enduring the rigors of cancer chemotherapy. In addition, in a small population of normal donors, G-CSF has also been associated with serious toxicity. Despite its success, poor mobilization in response to G-CSF occurs in 15% of normal, healthy donors. Patients who do not achieve sufficient numbers of CD34+ cells often require more than one apheresis procedure ([18-20]). Up to 60% of patients fail to mobilize an optimal CD34+ cell numbers for autologous transplantation requiring tandem cycles of high dose chemotherapy ([25-27]). This is a particular issue for patients with lymphoma and multiple myeloma ([28]) who often require extended aphereses ([29]) and comprise the largest group of transplant recipients. These issues provide the context in which alternative methods for mobilizing HSPC could have high impact.

The small molecule CXCR4 antagonist Plerixafor (AMD3100) has been shown to address the issue of poor mobilization with G-CSF alone ([32-35]) and is now approved by the FDA to be used in combination with G-CSF for mobilization of PBSC in patients with non-Hodgkin lymphoma or multiple myeloma who have failed GCSF. However a significant portion of patients still fail to mobilize sufficient numbers even after Plerixafor administration with approximately 33% of patients reporting diarrhea or injection site reaction. While Plerixafor plus G-CSF has clearly made an impact on the ability to mobilize HSCs in these patients, there remains considerable clinical opportunity for alternative agents. Agents that overcome the following issues would be particularly attractive: 1) the requirement for multiple daily injections of G-CSF, which leads to considerable bone pain and other undesired effects; 2) variable and suboptimal mobilization in subpopulations of patients and volunteers with currently existing mobilizing agents; 3) and the total number of aphereses procedures required and the inability to predict optimal mobilization times.

Testing the efficacy of mobilizing agents is facilitated by the clear endpoints for clinical efficacy. Clinical targets for adequate mobilization have been established. CD34+ cell doses of >3×106/kg are associated with reduced morbidity and mortality ([21]) among allogenic transplant recipients. Higher CD34+ cell doses up to 10×106/kg are reported to result in more rapid engraftment, less morbidity and better survival rates ([22]), particularly for patients with disease at high risk of relapse ([23, 24]). Therefore, parameters to measure success of mobilization regimens are in place. While the primary focus of this proposal is the development of pharmacologic alternatives to the existing therapies for hematopoietic stem cell harvest, there are additional opportunities for clinical impact that we propose exploring. Agents which mobilize endogenous stem cells from the niche can result in niche vacancies enabling transplanted cell engraftment. G-CSF is limited in this function because of its known adverse effects on the stem cell niche, but alternative approaches may not be similarly constrained. If this function can be optimized, the potential for 'conditioning' the recipient for stem cell engraftment without cytotoxic chemotherapy or radiation might be possible. Such an outcome is of increasing interest to the clinical community given the interest in treating non-malignant diseases such as sickle cell anemia, congenital immune deficiencies, storage defects and HIV. Defining whether new mobilizing agents can accomplish engraftment without cytotoxicity is an extension of the mobilization studies and of important potential impact.

Example 3

Enhance Niche Vacancy without Niche Toxicity Through Manipulation of CXCR2 and Recently Defined Heparan Sulfate Proteoglycan Interactions Between HSC and the Bone Marrow Niche Niche retention of HSPC is partially maintained by the interaction of SDF-1 with its cognate receptor CXCR4 on HSPC. Clinically, the CXCR4 antagonist AMD3100 is FDA approved for use in combination with G-CSF to enhance egress of HSPC from the bone marrow to the periphery for harvesting via apheresis and subsequent transplantation. While this combination clearly vacates the bone marrow niche, G-CSF causes significant attenuation of stromal niche cells.[18] This is of little consequence when the goal is simply stem cell harvesting, but it is problematic when considering vacating the niche to enable competing cells to engraft in the setting of low toxicity conditioning. This may be why G-CSF has been unsuccessful in this context; it reduces the supportive capacity of the niche for infused and endogenous cells. Therefore, strategies which cause HSPCs to vacate the niche while maintaining niche integrity are preferable for a reduced conditioning strategy. The work described herein contemplates using the combination of two such approaches to determine if adequate mobilization can occur to enable transplanted cell engraftment without disruption of the niche.

The CXCR2 agonist GRO-β is an agent capable of rapidly mobilizing HSPCs, and results in mobilization of long term repopulating HSCs with superior engraftment potential when compared with G-CSF.[19] This agent has a putative mechanism of action entirely different than G-CSF or AMD3100 in that it activates MMP-9. It does so acutely, mobilizing HSPC maximally by 15 minutes post infusion in mice. Unlike G-CSF, the mobilization is not associated with changes in marrow morphology by immunohistochemistry (data not shown). It is an excellent candidate to serve as a niche-vacating agent. We have also recently identified a novel involvement of heparan sulfate proteoglycans (HSPC) in HSC retention in the bone marrow that can be manipulated pharmacologically to induce stem cell mobilization of cells functionally distinctive from those mobilized by G-CSF. This process is one that involves the use of heparin and AMD3100 and achieves robust mobilization using approved agents that can quickly move to clinical trial.

Hypothesizing that extracellular matrix proteins serve as critical elements of the bone marrow niche it was demonstrated that osteopontin played such a role.[20, 21] Further, we tested whether HSPGs play a role since they are known to generate gradients of multiple other cytokines and morphogens in local tissues in development.[22, 23] To evaluate this, we examined the effects of conditional deletion of EXT1, the gene encoding a glycosyltransferase essential for the generation of heparan sulfate proteoglycans.[24] We did so by crossing conditional allele bearing mice with mice in which Cre recombinase is expressed under control of the Mx1 promoter. Mx1 is inducible by poly(I)/poly(C) in hematopoietic cells and, we recently showed, in osteolineage mesenchymal stem/progenitor cells.[25] To exclude a direct effect of EXT1 on hematopoietic cells, the studies below were conducted on animals which have been made chimeric by transplantation: their hematopoietic system is WT while the microenvironment is EXT1 fl/fl (KO) or +/+ (control).

Chimeric animals were evaluated for the effect of EXT1 deletion in the microenvironment on hematopoiesis by conditional activation of Cre followed by assessment of blood, bone marrow and spleen over 1-6 months (FIG. 1). The number of colony forming units (CFU) in the blood was significantly increased (p<0.01) (left panel) accompanied by a converse decrease in myeloid progenitors (middle panel) and HSC (right panel) in the bone marrow (p<0.05).

Figures 2A, 2B, 2C:
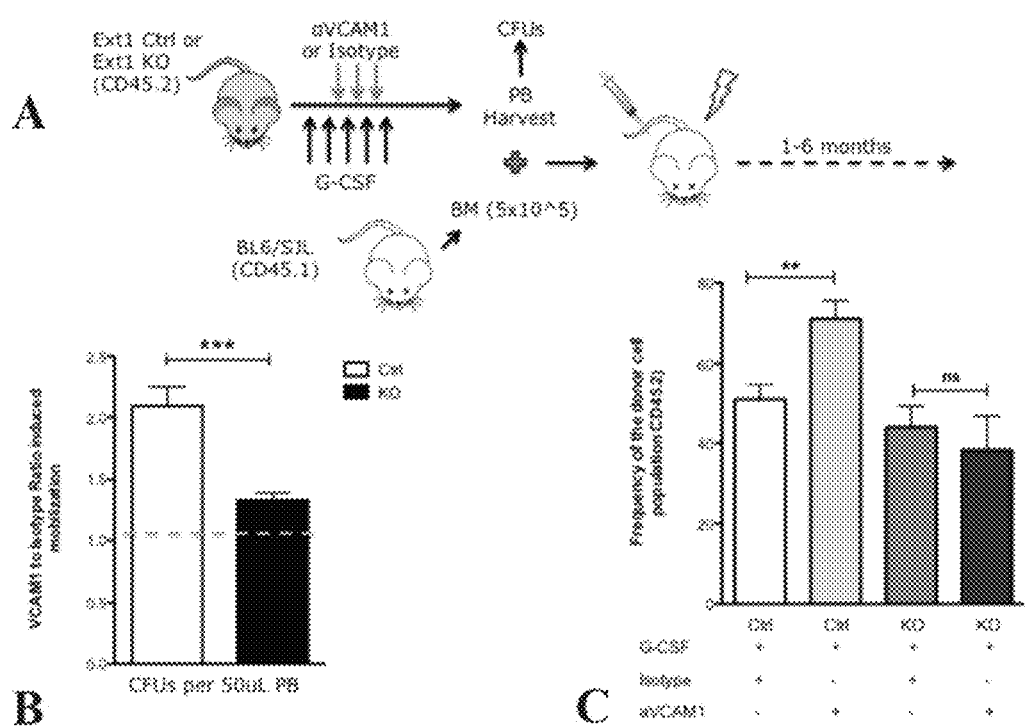
FIGS. 2A, 2B and 2C illustrate that heparan sulfate proteoglycans (HSPG) alter the activity of VCAM-1 on hematopoietic stem cell localization.

Examining the potential basis for this effect, we observed a decrease in VCAM-1 expression in the osteolineage cells of the bone marrow by IHC (data not shown) and tested the functional role of VCAM-1 by mobilization studies (FIG. 2). We used a VCAM-1 neutralizing antibody (or isotype control) in combination with G-CSF to mobilize cells (schematic representation, upper panel) and found that mobilization by G-CSF plus anti-VCAM-1 were additive (p<0.01) except in the setting of EXT1 deletion as measured by colony forming unit assays (p<0.001) and competitive transplantation assays (p<0.01). These data suggest not only that VCAM1 is one of the molecules participating in the alteration of HSPC retention in the marrow by EXT1 deletion but also support the distinctive mechanism of EXT1 deletion to G-CSF mobilization and the importance of EXT1-controlled HSPG in establishing VCAM-1 retention of stem cells in the bone marrow.

Figures 3A, 3B, 3C:
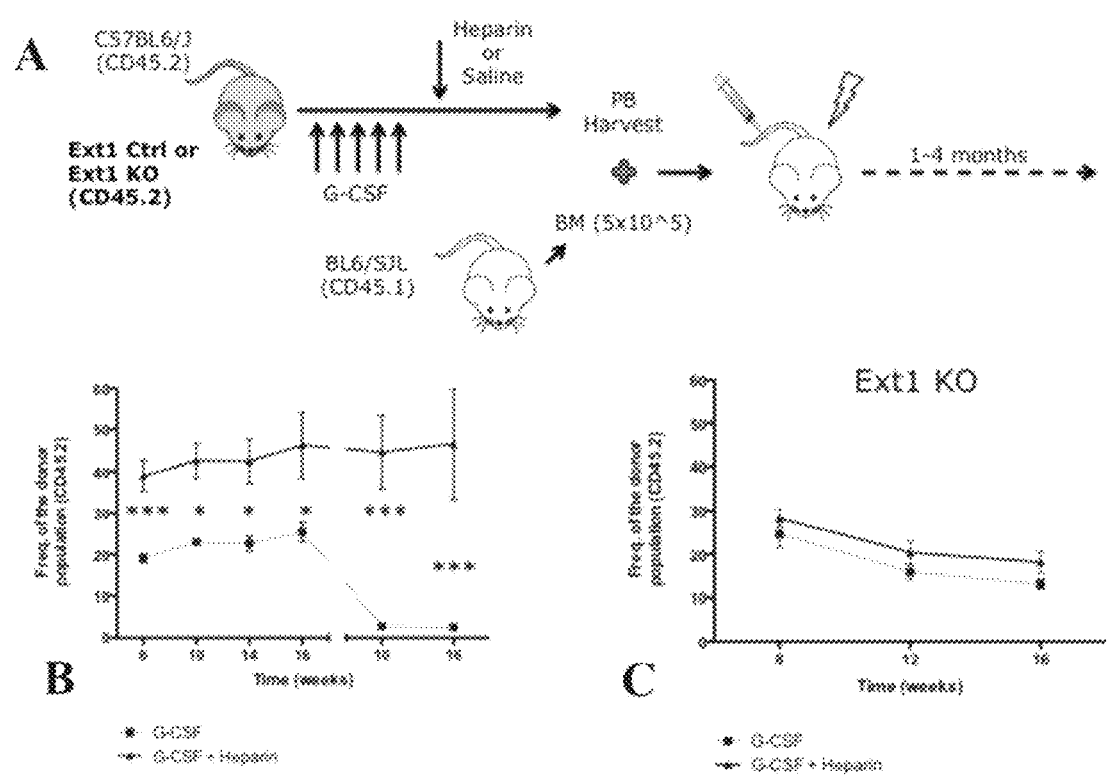
FIGS. 3A, 3B and 3C illustrate that heparin sulfate competes with endogenous HSPG and enables mobilization of functionally potent HSC.

Hypothesizing that endogenous HSPG could be competed with by known pharmacologic HSPG, we examined whether heparin sulfate could mimic the EXT1 deletion effect on stem cell localization. Initially, this was done using a single dose of heparin sulfate (100 U/mouse) after a standard G-CSF mobilization regimen, harvesting the peripheral blood and using it to reconstitute lethally irradiated congenic recipients (FIG. 3). The primary recipients were then harvested after 4 months and used to transplant secondary lethally irradiated recipients.

The results indicate that heparin sulfate does induce additive mobilization of stem cells (lower left panel). The cells appear to be distinctly more capable at providing secondary engraftment (post-interruption of line graphs, lower left panel) (p<0.001). These data suggest that the inexpensive, clinically available heparin sulfate is capable of mobilizing a functional distinct, perhaps functionally superior population of stem cells compared with G-CSF alone.

To test whether heparin sulfate was indeed functioning as a competitor with endogenous HSPG, we examined its ability to increase G-CSF mobilization in the EXT1 KO and observed loss of its effect (lower right panel). Therefore, heparin sulfate is inactive if endogenous proteoglycans are decreased; it depends on the presence of these molecules for its activity suggesting that it is indeed inhibiting HSPG, perhaps through binding to molecules such as VCAM-1 that are locally bound to endogenous HSPG.

Figure 4:
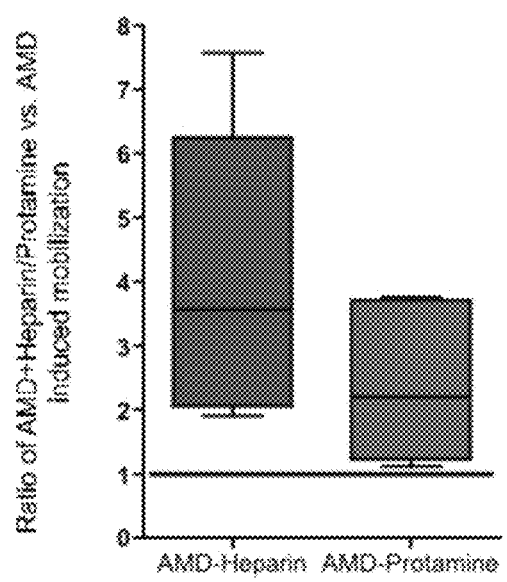
FIG. 4 illustrates markedly efficient stem cell mobilization by combining heparan sulfate inhibitors with AMD3100. Blood from animals treated with single dose AMD3100 alone (5 mg/kg) or AMD3100 plus heparin (100 U/mouse) or protamine sulfate (40 mg/kg) was used in transplantation of lethally irradiated congenic hosts and the relative frequency of engrafted donor cells is indicated. Line at 1=AMD3100 alone. Results are from 6-10 animals/group.

Since HSPG seemed to control the localization of stem cells with particularly potent secondary reconstituting ability and since HSPG inhibitors are readily available in the clinic, we tested whether this approach could be useful in the context where niche injury is to be avoided. We tested heparin sulfate or another clinically used HSPG antagonist, protamine sulfate, alone as stem cell mobilizers. Neither were sufficiently effective alone (data not shown). Therefore, we tested them with AMD3100 that can mobilize stem cells without the injury to endosteal cells associated with G-CSF. The data indicate that either agent provides enhance potency of mobilization compared with AMD3100 alone (indicate by line at 1 in FIG. 4) with AMD3100 plus heparin sulfate providing particular potency (2-6 fold enhancement) (p<0.05).

Given that GRO-β, HS inhibitors and AMD3100 are capable of rapidly mobilizing HSPC from the niche and target distinct molecular entities governing HSC localization, these agents can be used to maximally mobilize endogenous HSPC.

References from Examples 1-3

1. M. J. Kennedy et al., Cancer Res. 53, 5424 (1993).
2. I. G. McQuaker et al., J. Clin. Oncol. 15, 451 (1997).
3. J. Jansen et al., Bone Marrow Transplant. 23, 1251 (1999).
4. J. Nemunaitis et al., Bone Marrow Transplant. 15, 949 (1995).
5. Stem Cell Trialists' Group, J. Clin. Oncol. 23, 5074 (2005).
6. P. Anderlini et al., Bone Marrow Transplant. 27, 689 (2001).
7. P. Anderlini, D. Przepiorka, M. Korbling, R. Champlin, Bone Marrow Transplant. 21 Suppl 3, S35 (1998).
8. S. D. Rowley, G. Donaldson, K. Lilleby, W. I. Bensinger, F. R. Appelbaum, Blood 97, 2541 (2001).
9. C. Fortanier et al., Bone Marrow Transplant. 29, 145 (2002).
10. P. Anderlini et al., Transfusion 37, 507 (1997).
11. D. Lysak et al., Transfusion 51, 319 (2011).
12. M. M. Mueller et al., Vox Sang. 104, 46 (2013).
13. M. Cavo et al., J. Clin. Oncol. 25, 2434 (2007).
14. M. A. Gertz, Br. J. Haematol. 150, 647 (2010).
15. M. Attal et al., N Engl. J. Med. 349, 2495 (2003).
16. P. Stiff et al., Bone Marrow Transplant. 26, 471 (2000).
17. N. Schmitz et al., Blood 85, 1666 (1995).
18. H. E. Broxmeyer et al., J Exp. Med. 201, 1307 (2005).
19. J. F. DiPersio et al., J. Clin. Oncol. 27, 4767 (2009).
20. J. F. DiPersio et al., Blood 113, 5720 (2009).
21. L. M. Pelus, Curr Opin Hematol 15, 285 (2008).
22. S. M. Kymes et al., Am. Manag. Care 18, 33 (2012).
23. H. Bittencourt et al., Blood 99, 2726 (2002).
24. M. A. Pulsipher et al., Blood 114, 2606 (2009).
25. R. Nakamura et al., Biol. Blood Marrow Transplant, 14, 449 (2008),
26. J. P. Panse et al., Br. J. Haematol, 128, 659 (2005).

Example 4

Inhibiting Mesenchymal Cell Heparan Sulfate Production Improves Stem Cell Mobilization and Enables Engraftment without Cytotoxic Conditioning Introduction The glycosyltransferase gene, Ext1 is essential for heparan sulfate (HS) production and when inhibited in a population of mesenchymal cells (skeletal stem/progenitor cells) of adult mice results in marked changes in hematopoietic stem and progenitor cell (HSPC) localization. HSPC egressed from bone marrow to spleen after Ext1 deletion. This was associated with altered signaling in the mesenchymal cells and reduced Vcam1 production by them. Further, pharmacologic inhibition of HS mobilized qualitatively more potent and quantitatively more HSPC from the bone marrow than G-CSF alone including in a setting of G-CSF resistance. The reduced presence of endogenous HSPC following Ext1 deletion was associated with engraftment of transfused HSPC without any toxic conditioning of the host. Therefore inhibiting HS production may provide a means for avoiding the toxicities of radiation or chemotherapy in HSPC transplantation for non-malignant conditions.

Establishing patterns of cells in development is fundamental to the higher order of organization needed by multicellular organisms. Morphogen gradients play central roles in pattern establishment and subsequent tissue function (Akiyama et al., 2008; Vied et al., 2012) and are maintained through interactions with heparan sulfate proteoglycans (HSPGs) (Inatani et al., 2003). In the hematopoietic system, HSPGs interact with key hematopoietic cytokines in vitro, suggesting their potential role in bone marrow (BM) compartmentalization (Gordon et al., 1987; Roberts et al., 1988).

Our laboratory recently described a population of bone marrow (BM) skeletal stem/progenitors characterized by the interferon inducible expression of the Myxovirus resistance 1 (Mx1) gene (Park et al., 2012). These cells participate in bone homeostasis and partially overlap with the Nestin1+ mesenchymal population shown to be a component of the HSPC niche (Mendez-Ferrer et al., 2010). We hypothesized that cytokines and morphogens maintained by interaction with locally secreted matrix proteins are essential in maintaining the hematopoietic stem/progenitor cell (HSPC) niche. To test this, we conditionally deleted the Ext1 gene, a glycosyltransferase essential for the synthesis of heparan sulfate (HS) (Inatani et al., 2003; McCormick et al., 1998), in Mx1+ mesenchymal cells.

Our data demonstrate that Ext1/HSPG expressed in Mx1+ mesenchymal cells and their descendants control HSPC localization and retention in the BM, in part by modulating vascular cell adhesion molecule-1, Vcam1. Competitive pharmacologic inhibition of endogenous HS enhanced the mobilization efficacy of Granulocyte-Colony Stimulating Factor (G-CSF) including in the setting of mobilization resistance in a diabetes model. Further, the mobilized HSPCs had improved kinetics of reconstitution in primary and secondary transplants in irradiated hosts. Finally, engraftment of transplanted HSPCs occurred efficiently without cytotoxic conditioning shortly after mice were rendered Ext-1 deficient.

These findings demonstrate the critical role of HS in the bone marrow hematopoietic stem cell niche and suggest that targeting HS or the enzyme, Ext1, may provide novel methods for achieving outcomes in either mobilization or engraftment that are of importance for clinical transplantation.

Results

Heparan Sulfate Controls HSPC Localization

Figures 6A, 6B, 6C, 6D, 6E, 6F:
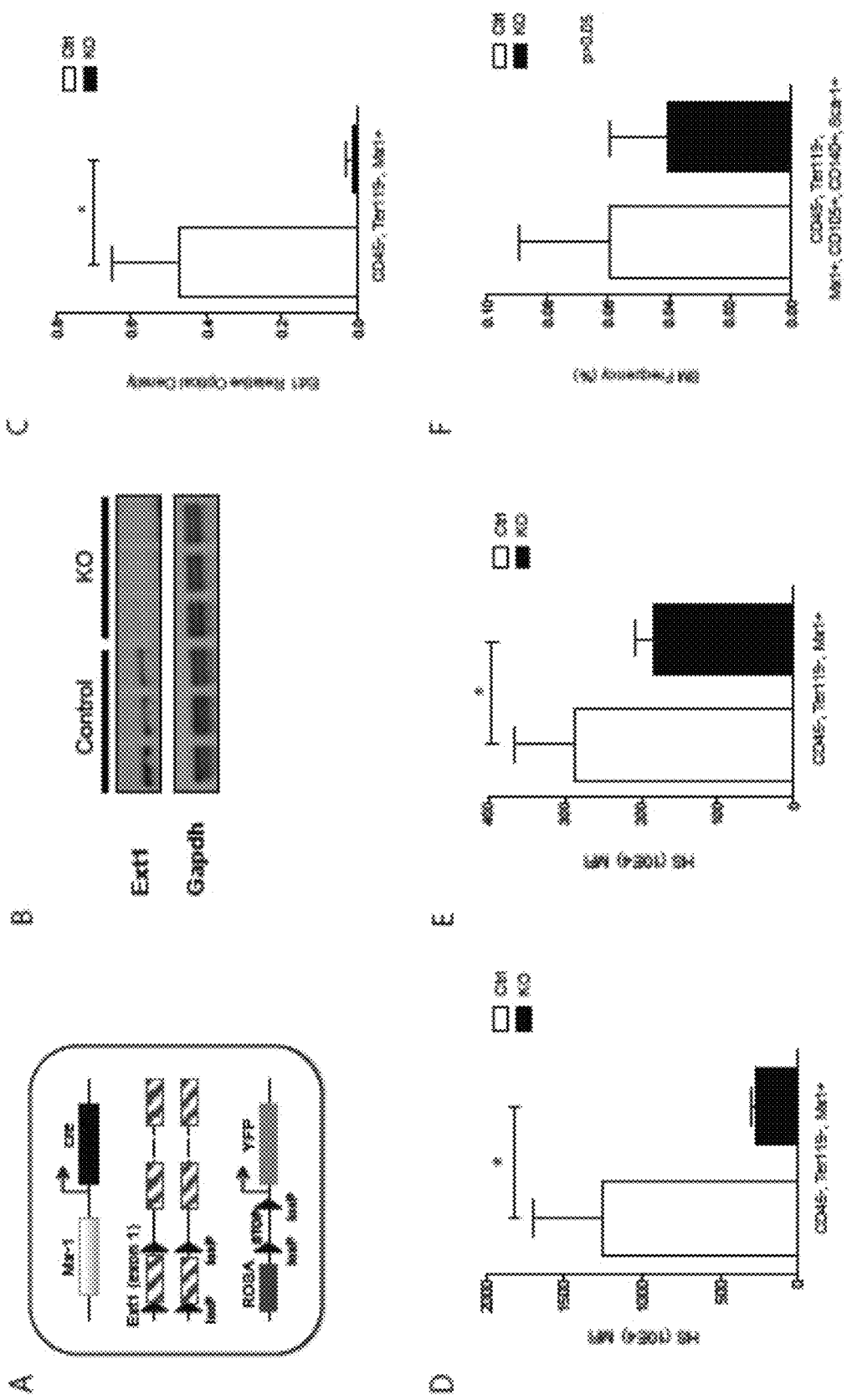
FIGS. 6A, 6B, 6C, 6D, 6E, 6F, 6G, 6H, 6I, 6J, 6K, 6L, 6M, 6N, 6O, 6P, 6Q, 6R, 6S, 6T, 6U, 6V and 6W demonstrate that heparan sulfate proteoglycans control hematopoietic stem/progenitor cell localization.

Mx1 is expressed in the hematopoietic system and in osteolineage mesenchymal cells following interferon induction by Poly(I):Poly(C) (pIpC) (Kuhn et al., 1995; Park et al., 2012). Biallelic deletion of foxed alleles by cre recombinase driven by the Mx1 promoter is highly efficient in the hematopoietic system (Gurumurthy et al., 2010) but less characterized in the mesenchymal compartment. To evaluate the efficiency of Ext1 deletion in the mesenchymal compartment upon pIpC administration, control and mutant Ext1 mice were crossed with the ROSA26-loxP-stop-loxP-EYFP (Rosa-YFP) reporter mice to generate Ext1flox/flox; Mx1cre+; Rosa-YFP+ (mutant-YFP) and Ext1+/+; Mx1cre+; Rosa-YFP+ (control-YET) animals (FIG. 6A). Mutant and control YFP+, CD45−, Ter119− skeletal progenitors were flow sorted twenty-one days after pIpC induction and efficient deletion of Ext1 was verified in ex vivo expanded cells by western blotting (FIGS. 6B and 6C).

Furthermore, significant abrogation of HS production upon Ext1 deletion was detected in ex vivo expanded as well as freshly isolated Mx1+ mesenchymal cells (FIGS. 6D and 6E). Importantly, deletion of Ext1 did not affect the abundance of immunophenotypically defined mesenchymal stem cells in the BM (FIG. 6F).

Figures 5A, 5B, 5C, 5D, 5E, 5F:
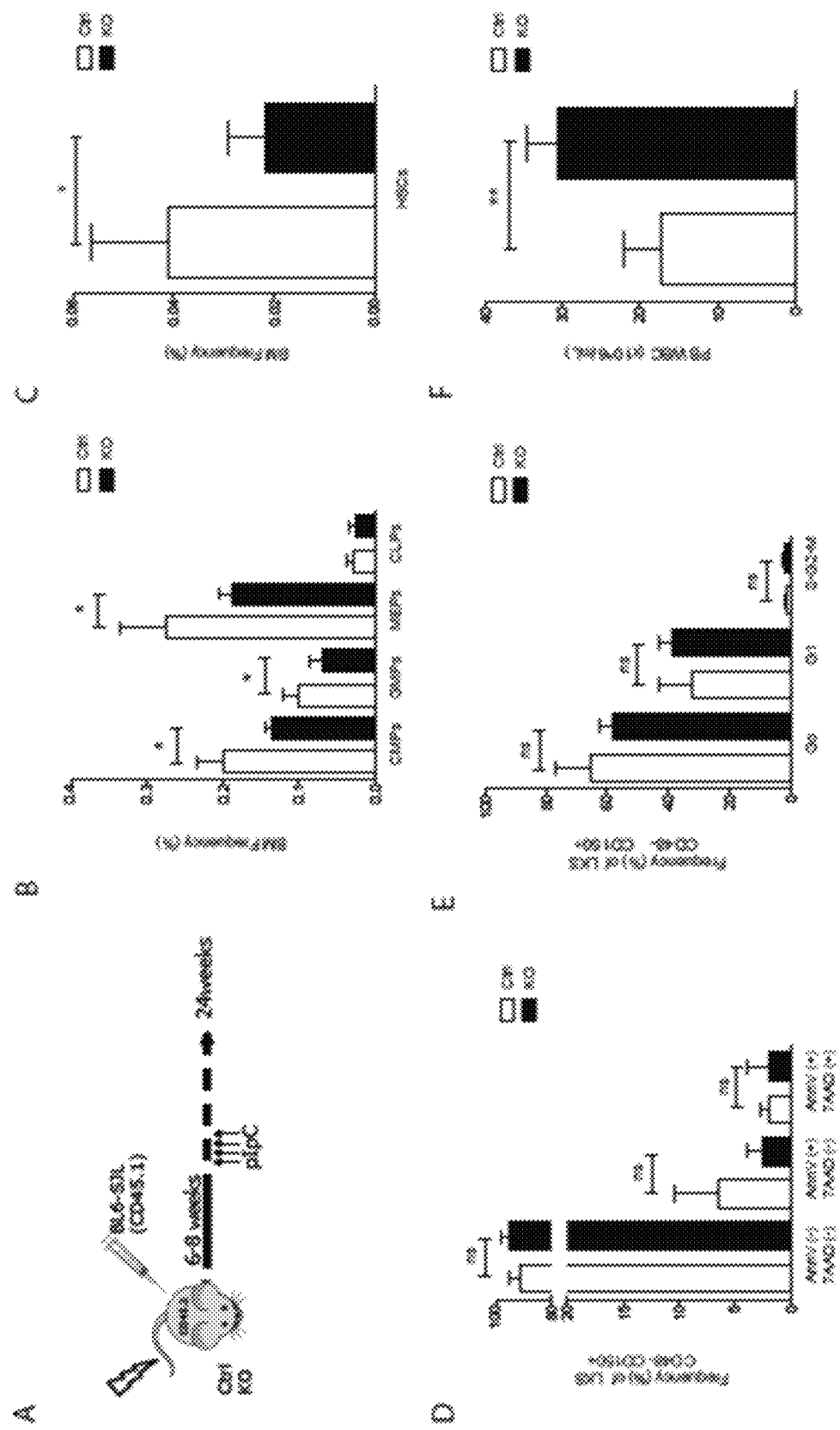
FIGS. 5A, 5B, 5C, 5D, 5E, 5F, 5G, 5H, 5I, 5J, 5K, and 5L demonstrate that heparan sulfate proteoglycans control HPSC localization.
Figures 6G, 6H, 6I, 6J, 6K, 6L:
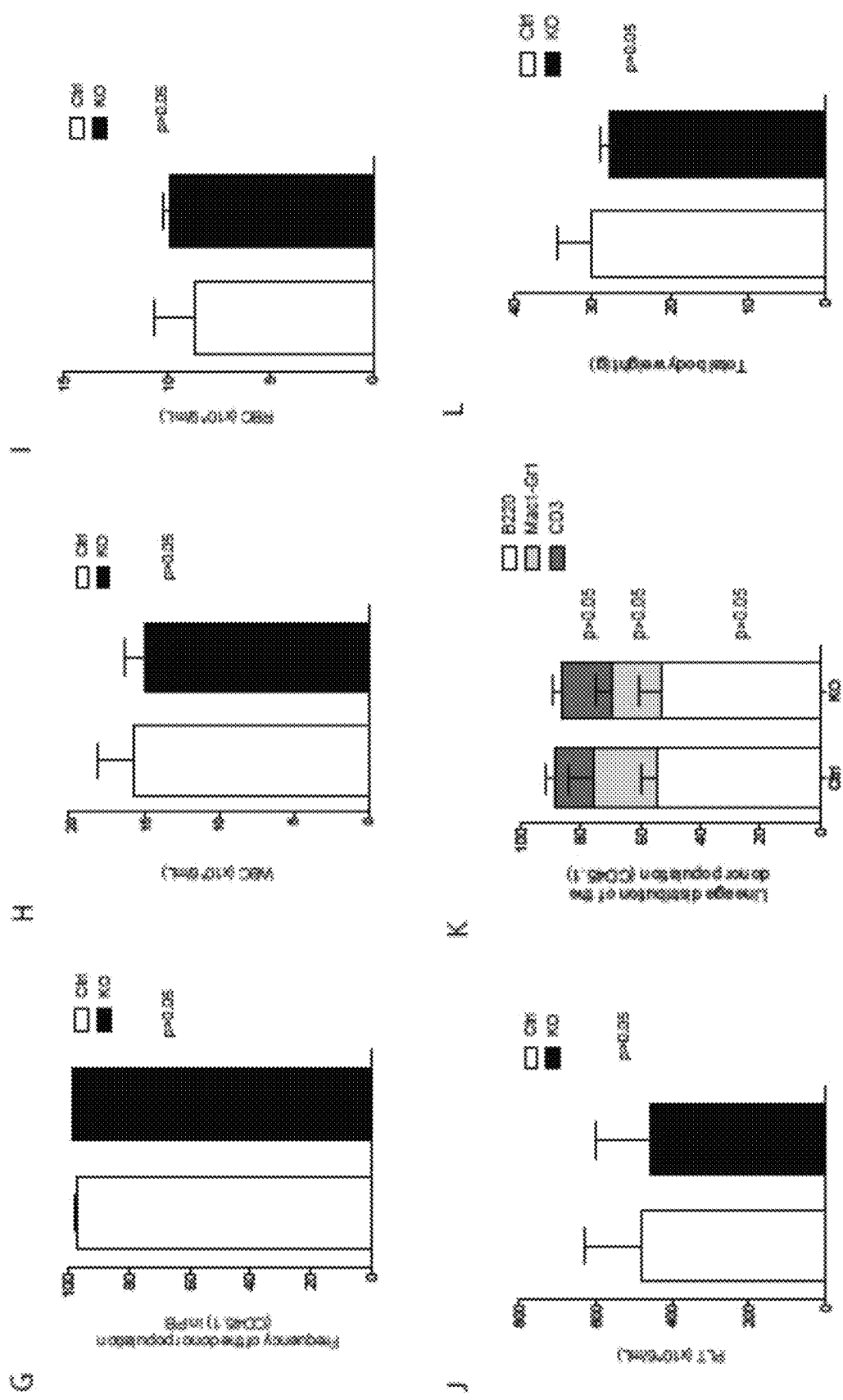
Figures 6M, 6N, 6O, 6P, 6Q, 6R:
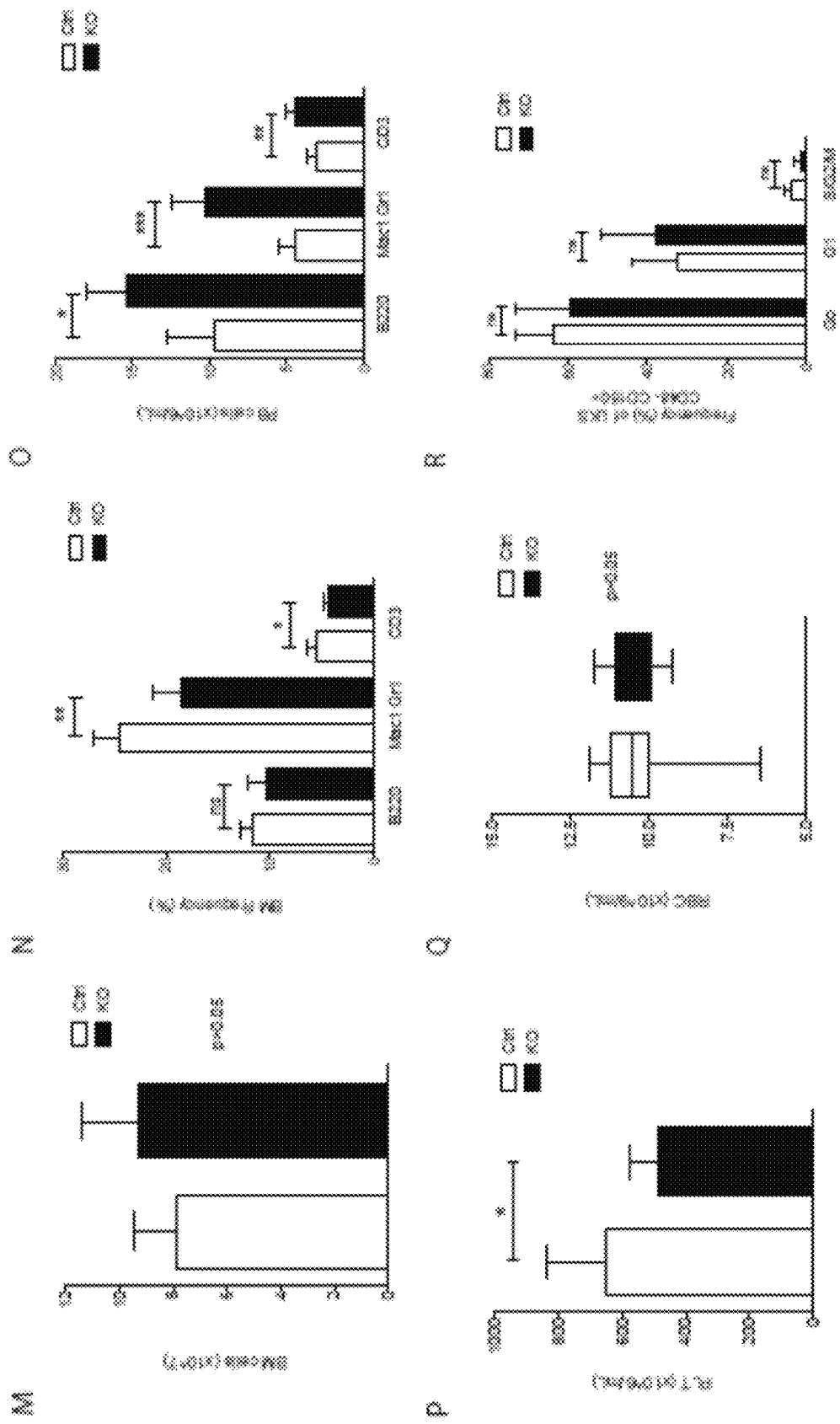

To restrict Ext1 deletion to Mx1+ skeletal progenitors, we transplanted total BM cells from CD45.1 expressing congenic animals (B6.SJL) into lethally irradiated mutant (Ext1flox/flox; Mx1cre+) or control (Ext1flox/flox; Mx1cre−) mice (both in C57BL/6J background) (FIG. 5A) to create control and mutant chimeras. Six to eight weeks after transplantation the hematopoietic system was fully replaced by CD45.1 cells (FIG. 6G) and chimeric animals displayed equivalent hematopoietic parameters such as white blood cell (WBC), red blood cells (RBCs), platelet counts and WBC lineage distribution in the peripheral blood (PB) (FIGS. 6H, 6I, 6J and 6K). Ext1 was then deleted in non-hematopoietic cells by pIpC induction and hematopoiesis was monitored for 24 weeks. At 24-weeks post-pIpC, both control and mutant chimeric mice displayed comparable total body weight (TBW) and BM cellularity (FIGS. 6L and 6M). Bone marrow immunophenotypic analysis revealed a significant decrease in the proportion of Mac1+ Gr1+ and CD3+ cells in mutant chimeras and a trend toward a decrease in the B220+ population (FIG. 6N). Similarly, we found a significant decrease in the proportion of mature myeloid progenitors (Common Myeloid Progenitors or CMPs, Megakaryocyte Erythroid Progenitors or MEPs and Granulocyte Macrophage Progenitors or GMPs) (FIG. 5B), a trend toward decreased Common Lymphoid Progenitors (CLPs) as well as a two-fold decrease in the proportion of LKS CD48−CD150+ Hematopoietic Stem Cells (HSCs) in the BM of mutant chimeric mice (FIG. 5C), These changes, however, could not be attributed to an increase in HSC death nor to a proliferation defect (FIGS. 5D and 5E). Given the lack of changes in apoptosis and cell cycle of HSCs in mutant chimeric mice, we assessed for mislocalization of HSPCs by examining the PB and spleen. During the 24-week time course, mutant chimeras developed a marked leukocytosis (FIG. 5F) (with a significant increase in the numbers of lymphoid and myeloid cells in PB (FIG. 6O)) and a moderate thrombocytopenia with normal red blood cell (RBC) counts (FIGS. 6P and 6Q). In addition, PB colony forming assays (CFU-C) displayed a significant increase in circulating progenitors in mutant chimeric mice (FIG. 5O).

Figures 5G, 5H, 5I, 5J, 5K, 5L:
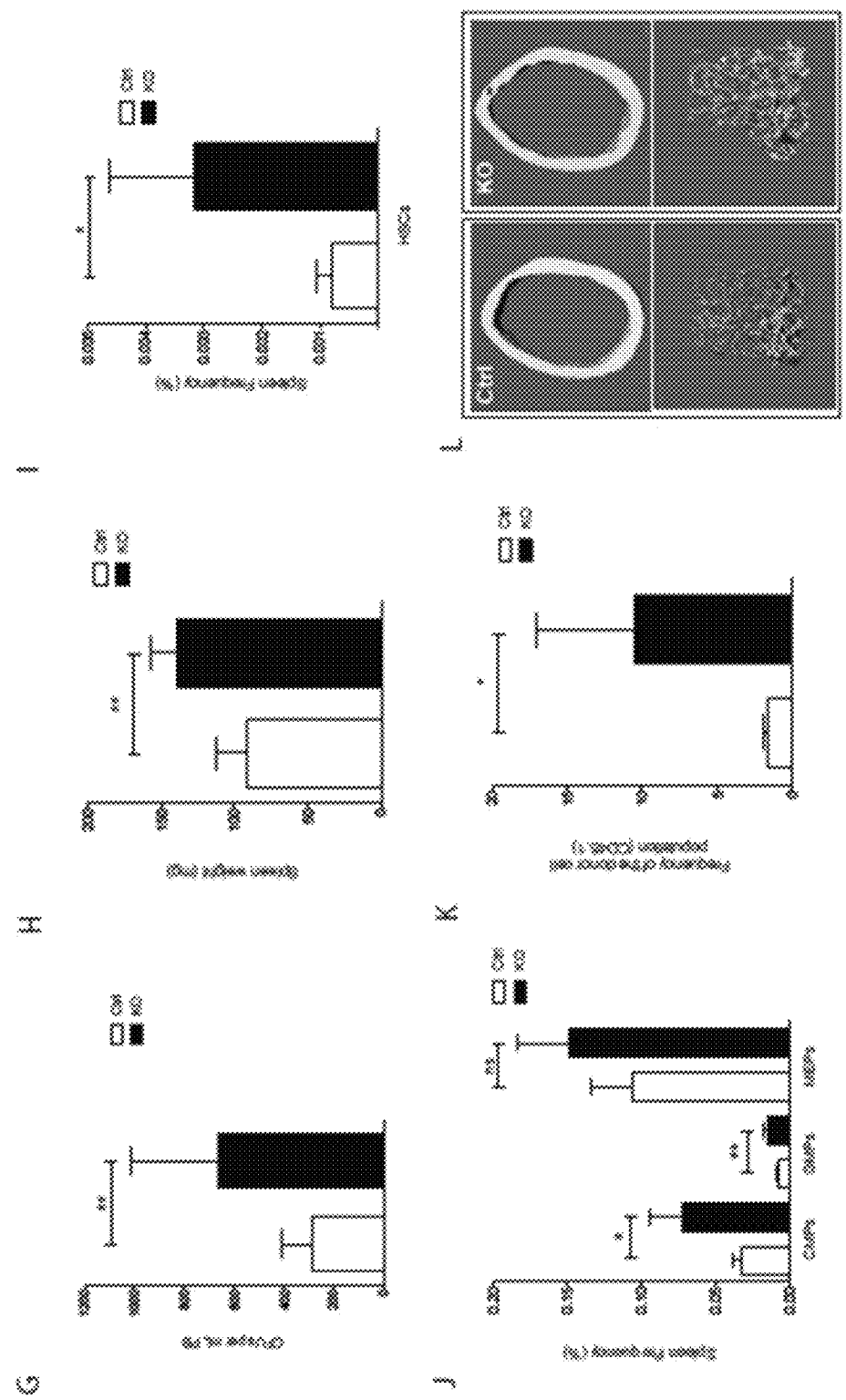
Figures 6S, 6T, 6U, 6V, 6W:
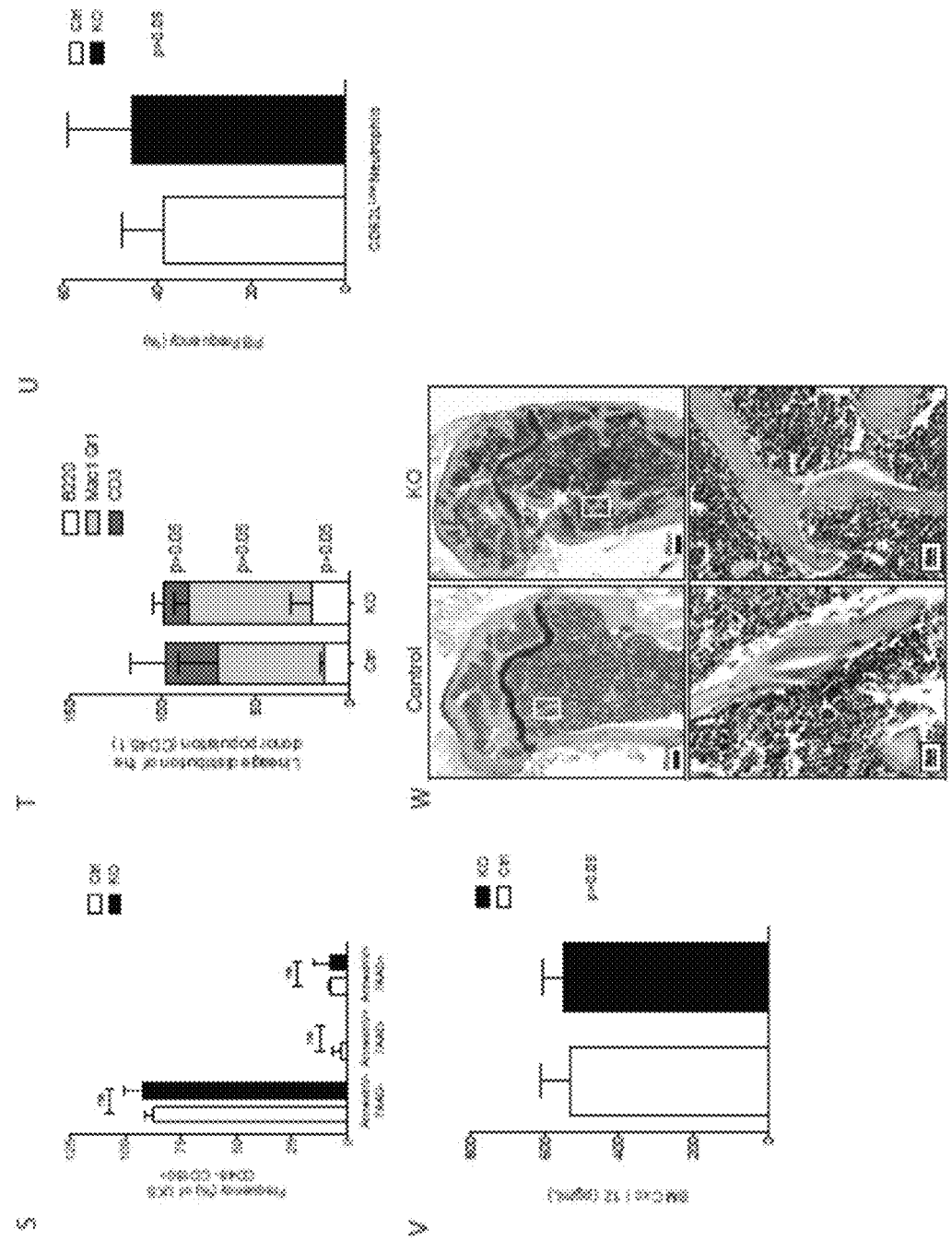

Mutant chimeras had significantly larger spleens at 24 weeks post pIpC injection (FIG. 5H). Immunophenotypic characterization of the spleen revealed a substantial increase in the proportion of HSCs (FIG. 5I), CMPs and GMPs but not MEPs in these mice (FIG. 5J). This accumulation of HSCs in the spleen cannot be attributed to an increase in their proliferation or a resistance to cell death (FIGS. 6R and 6S). Furthermore, competitive transplantation of spleen cells from mutant chimeric mice with equal numbers of spleen cells from C57BL/6J mice revealed a significant, long term, competitive advantage compared to spleen cells from control chimeras (FIG. 5K). Contribution to blood cell lineages by HSCs from control and mutant chimeras in this transplantation experiment was equivalent. (FIG. 6T).

Mislocalization of HSPCs has been associated with neutrophil turnover and neutrophil-induced BM microenvironment changes (Casanova-Acebes et al., 2013). Distribution of circulating "aged" neutrophils (FIG. 6U) and BM Cxcl12 levels (FIG. 6V) were equivalent in control and mutant chimeric Ext1 mice suggesting that the neutrophilia observed in our model does not account for the HSPC mislocalization. Given that osteolineage cells have been shown to impact hematopoiesis in a number of murine models (Mercier et al., 2012) we evaluated whether the observed HSPC mislocalization in Ext1 mutant mice was a consequence of impaired osteolineage cell function. Bone histomorphometric, micro CT and histologic analysis showed no significant differences, suggesting that Ext1 deletion in Mx1+ skeletal progenitors is not essential for skeletal homeostasis (FIG. 5L, FIG. 6W, Table 1, and Table 2). Taken together these results indicate that production of HS by a population of Mx1+ skeletal progenitors regulates HSPC retention in the BM cavity.

TABLE 1

Male EXT-1 control and mutant femur microCT analysis

| Parameters | EXT-1-loxP/loxP− (n = 8) | EXT-1-loxP/loxP− Mx1cre+ (n = 4-5) | p value |
|---|---|---|---|
| Cortical Bone | | | |
| Total cross-sectional volume (mm$^3$) | 1.02 ± 0.13 | 0.96 ± 0.07 | 0.371 |
| Cortical volume (mm$^3$) | 0.41 ± 0.08 | 0.37 ± 0.06 | 0.408 |
| Marrow volume (mm$^3$) | 0.62 ± 0.10 | 0.59 ± 0.04 | 0.617 |
| Cortical thickness (mm) | 0.16 ± 0.03 | 0.15 ± 0.02 | 0.347 |
| Cancellous Bone | | | |
| BV/TV (—) | 0.05 ± 0.04 | 0.04 ± 0.02 | 0.681 |
| Tb.Th (mm) | 0.040 ± 0.009 | 0.039 ± 0.008 | 0.829 |
| Tb.N (/mm) | 2.57 ± 0.44 | 2.81 ± 0.38 | 0.391 |
| Tb.Sp (mm) | 0.40 ± 0.07 | 0.36 ± 0.05 | 0.352 |
| Conn.D (/mm$^3$) | 61 ± 44 | 51 ± 20 | 0.674 |
| SMI (—) | 2.78 ± 0.65 | 3.08 ± 0.19 | 0.395 |

Abbreviations:
BV, bone volume;
TV, total volume;
Tb, trabecular;
Th, thickness;
n, number;
Sp, separation;
Conn.D, connectivity density;
SMI, structure model index.
Values are expressed as the mean ± SD.

TABLE 2

Male EXT-1 control and mutant proximal tibia histomorphometric analysis

| Parameters | EXT-1-loxP/loxP− Mx1cre− (n = 8) | EXT-1-loxP/loxP− Mx1cre+ (n = 5) | p value |
|---|---|---|---|
| BV/TV (%) | 2.62 ± 0.18 | 2.16 ± 1.23 | 0.673 |
| Tb.Th (μm) | 32.41 ± 15.24 | 23.58 ± 4.77 | 0.241 |
| Tb.N (/mm) | 0.71 ± 0.33 | 0.86 ± 0.47 | 0.508 |
| Tb.Sp (μm) | 1727 ± 1083 | 2334 ± 3062 | 0.612 |
| MS/BS (%) | 27.34 ± 11.66 | 28.47 ± 12.52 | 0.872 |
| MAR (μm/day) | 1.72 ± 0.33 | 1.33 ± 0.82 | 0.252 |
| BFR/BS (μm$^3$/μm$^2$/year) | 163 ± 62 | 164 ± 102 | 0.992 |
| BFR/BV (%/year) | 1059 ± 374 | 1278 ± 804 | 0.514 |
| BFR/TV (%/year) | 27 ± 19 | 35 ± 25 | 0.489 |
| Ob.S/BS (%) | 23.69 ± 15.79 | 17.38 ± 11.73 | 0.460 |
| N.Ob/T.Ar (/mm$^2$) | 28.08 ± 29.96 | 24.25 ± 14.16 | 0.796 |
| N.Ob/B.Pm (/mm) | 17.08 ± 9.76 | 12.00 ± 7.45 | 0.343 |
| OV/TV (%) | 0.126 ± 0.272 | 0.039 ± 0.031 | 0.500 |
| OS/BS (%) | 14.02 ± 16.47 | 7.85 ± 6.27 | 0.446 |

TABLE 2-continued

Male EXT-1 control and mutant proximal tibia histomorphometric analysis

| Parameters | EXT-1-loxP/loxP-<br>Mx1cre−<br>(n = 8) | EXT-1-loxP/loxP-<br>Mx1cre+<br>(n = 5) | p value |
|---|---|---|---|
| O.Th (μm) | 3.18 ± 1.04 | 2.05 ± 1.22 | 0.101 |
| Oc.S/BS (%) | 4.94 ± 2.77 | 3.35 ± 1.39 | 0.263 |
| N.Oc/T.Ar (/mm²) | 2.00 ± 0.98 | 2.43 ± 1.69 | 0.569 |
| N.Oc/B.Pm (/mm) | 1.56 ± 0.81 | 1.55 ± 0.74 | 0.987 |
| ES/BS (%) | 3.01 ± 1.49 | 2.46 ± 0.90 | 0.474 |

Abbreviations:
BV, bone volume;
TV, total volume;
Tb, trabecular;
Th, thickness;
n, number;
Sp, separation;
MS/BS: mineralized surface/bone surface;
MAR: mineral apposition rate;
BFR/BS: boneformation rate/bone surface;
BFR/BV: bone formation rate/bone volume;
BFR/TV: bone formationrate/total volume;
ObS/BS: osteoblast surface/bone surface;
N.Ob/T.Ar: number of osteoblast/totalarea;
N.Ob/B.Pm: number of osteoblast/bone perimeter;
OV/TV: osteoid surface/total volume;
OS/BS: osteoid surface/bone surface,
O.Th: osteoid thickness,
Oc.S/BS: osteoclast surface/bonesurface;
N.Oc/T.Ar: number of osteoclasts/total area;
N.Oc/B.Pm: number of osteoclasts/bone perimeter;
ES/BS: erosion surface/bone surface.
Values are expressed as the mean ± SD.

Heparan Sulfite Modulates Learn 1-Dependent HSPC Adhesion

Figures 7A, 7B, 7C, 7D, 7E:
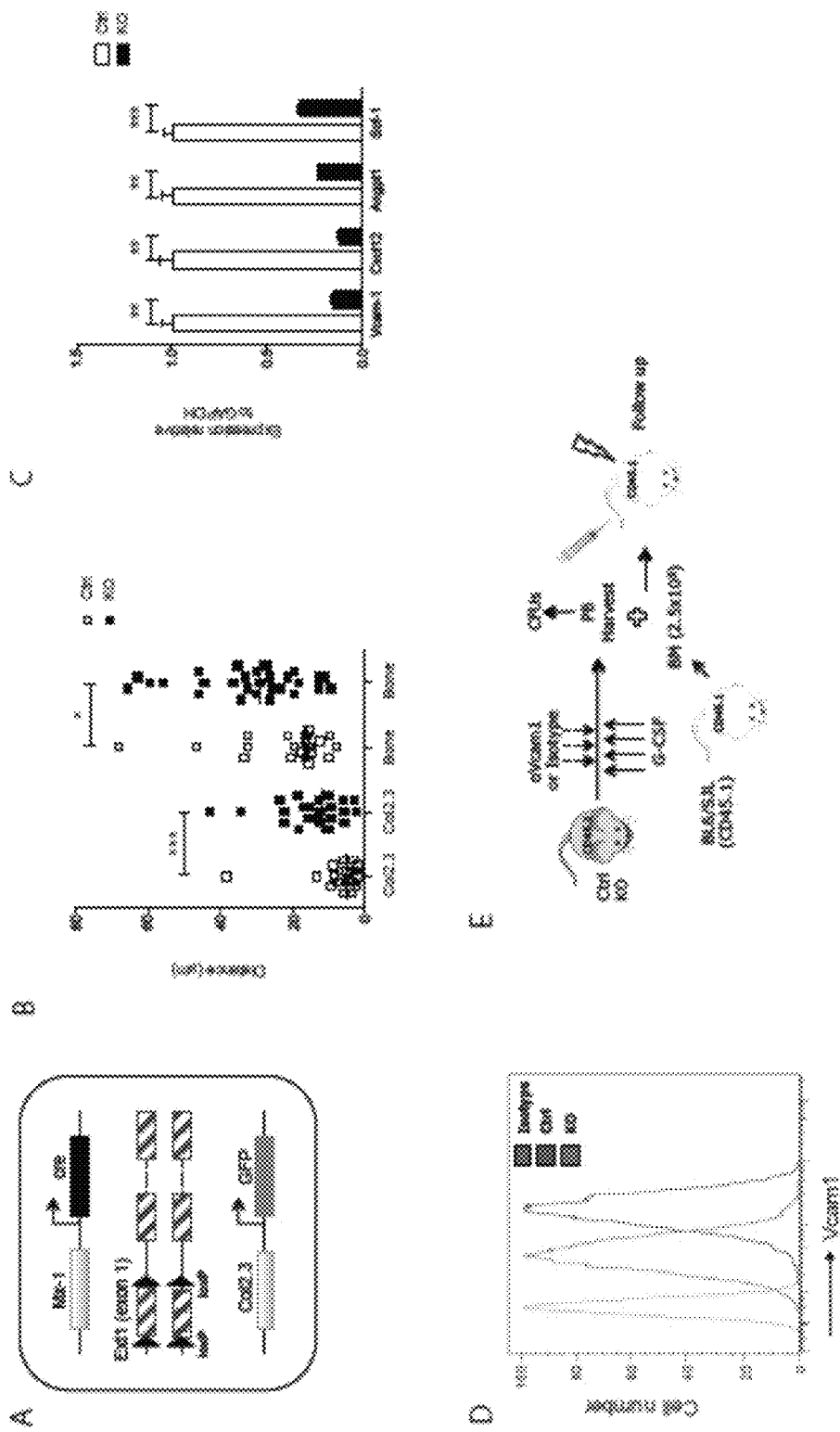
FIGS. 7A, 7B, 7C, 7D, 7E, 7F and 7G demonstrate that heparan sulfate modulates Vcam1-dependent HSPC adhesion.
Figure 8A:
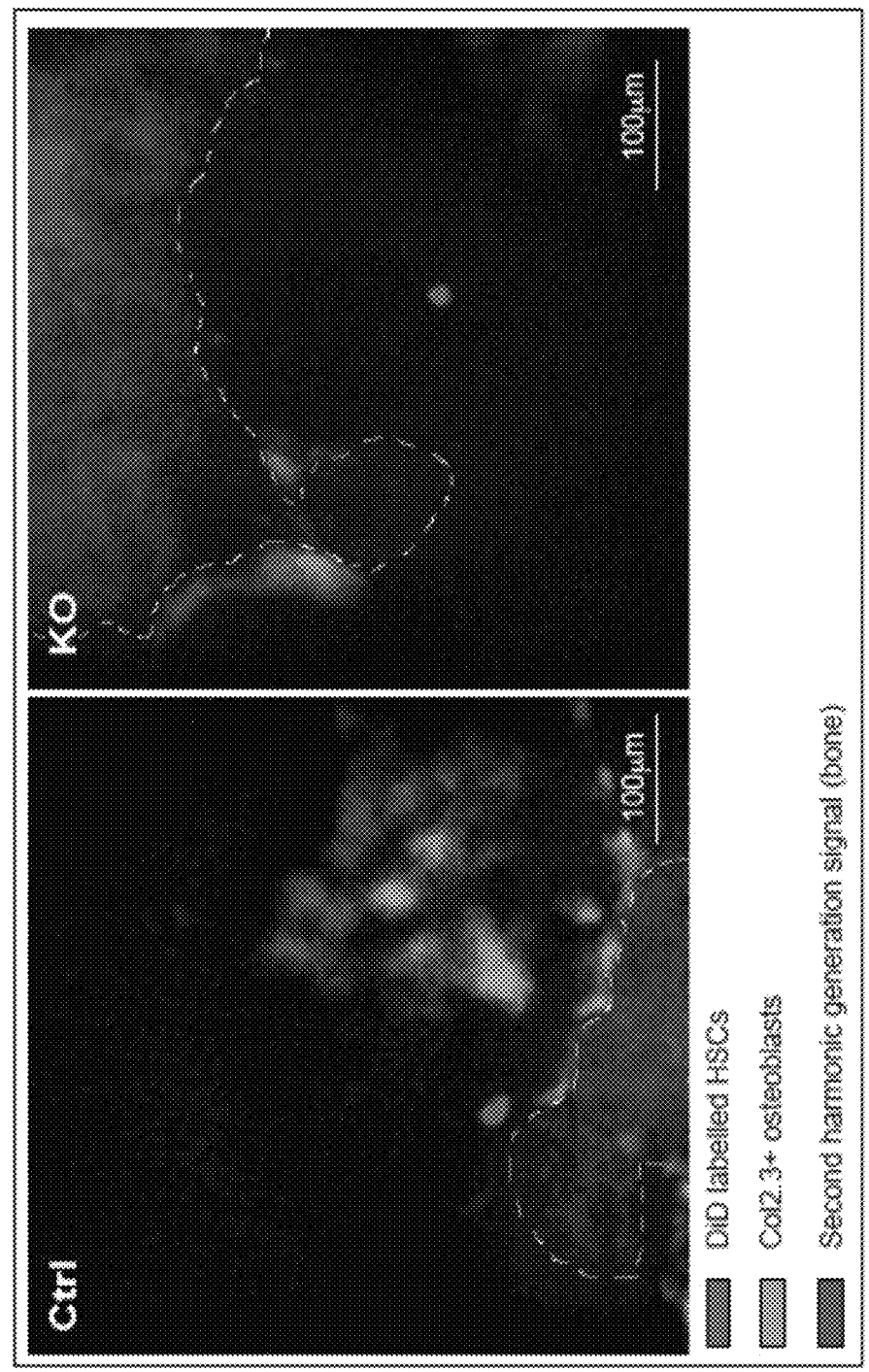
FIGS. 8A, 8B, 8C and 8D further demonstrate that heparan sulfate modulates Vcam1-dependent HSC adhesion.

Micro-anatomic positioning of HSPCs in the BM influences their heterotypic interactions altering activity and response to stimuli. We evaluated whether HSPC positioning in the BM was affected upon Ext1 deletion in Mx1+ skeletal progenitor cells. Control and mutant mice were bred into a reporter strain expressing GFP under the Col2.3 promoter (Col2.3-GFP), specifically labeling osteoblastic cells (FIG. 7A). Ext1 control and mutant Col2.3-GFP+ mice were lethally irradiated and transplanted with 104 WT LKS CD48−, CD150+ DiD (1,1'-dioctadecil-3,3,3'-tetramethylin-dodicarbocyanine perchlorate) labeled HSCs. Labeled HSCs were visualized in the calvarial BM 24 hours after injection by means of intra-vital high-resolution two-photon and confocal microscopy and their relative distance to osteoblastic cells (Col2.3-GFP+) and the endosteal surface was quantified. The anatomic positioning of DiD+ cells in the mutant animals was markedly changed with cells at a greater distance from GFP+ osteolineage cells (FIG. 7B and FIG. 8A). To investigate whether HS affected the regulation of molecules known to modulate HSPC localization, control and mutant YFP+ (FIG. 6A), CD45−, Ter119− skeletal progenitors were flow sorted twenty-one days after pIpC induction. Assessment of mRNA levels revealed that the expression of Cxcl12, Vcam1, Scf and angiopoietin-1 (Mercier et al., 2012), were significantly down regulated in mutant mice, consistent with the observed HSC localization further away from osteoblastic cells (FIG. 7C).

Figure 7F:
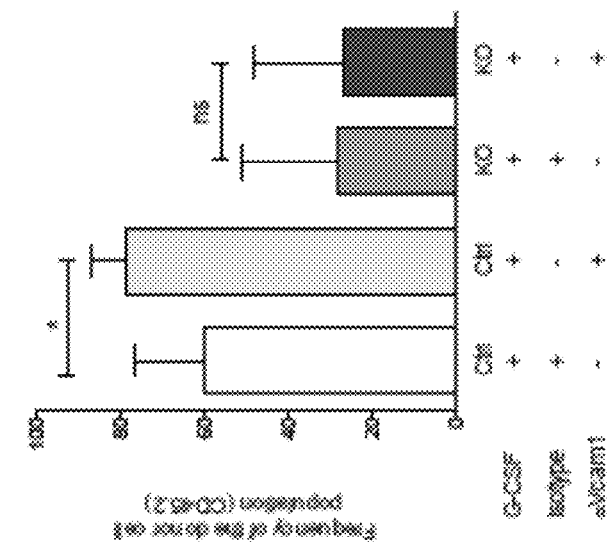
Figure 7G:
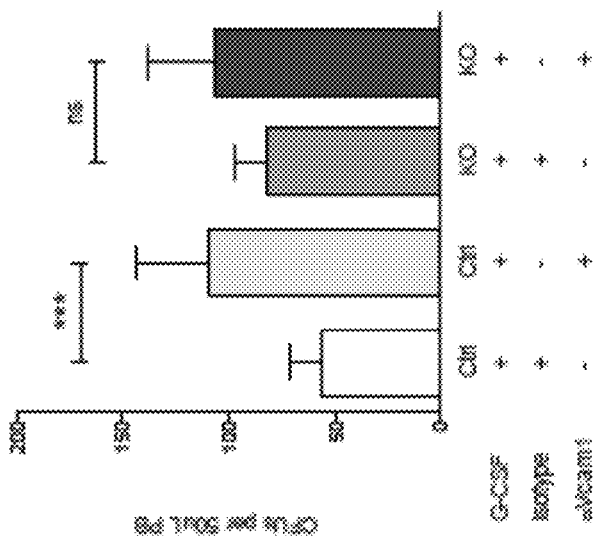
Figures 8B, 8C, 8D:
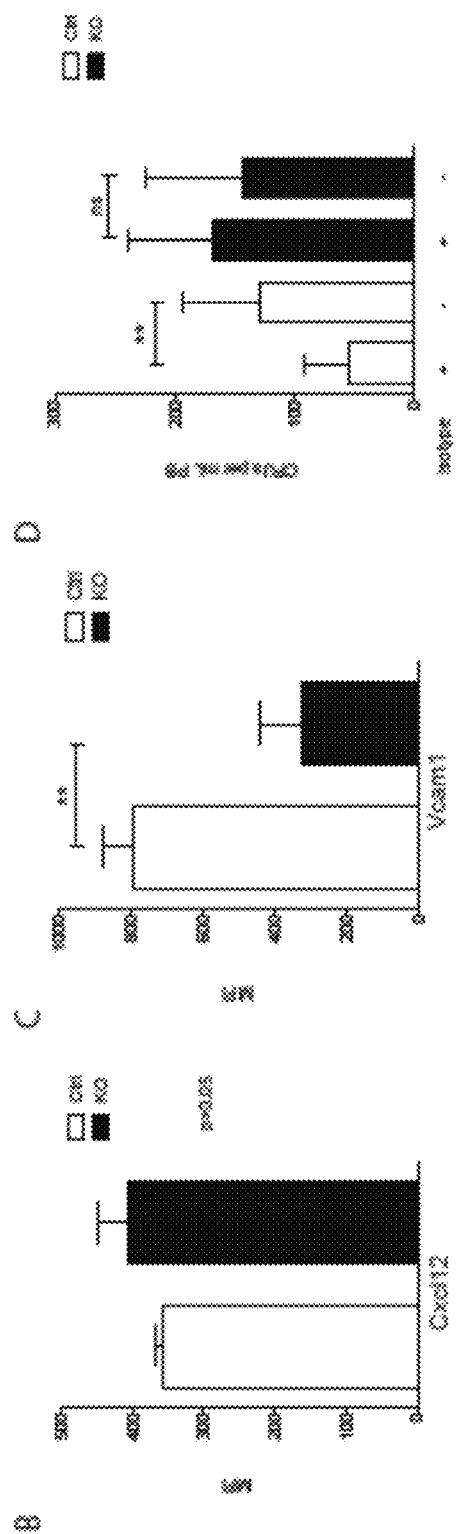

Conditional deletion of Cxcl12 and Scf in osteolineage cells does not impact HSPC biology (Ding and Morrison, 2013; Ding et al., 2012; Greenbaum et al., 2013) and angiopoietin1 controls HSC quiescence (Arai et al., 2004), a state that was not changed in HSCs upon Ext1 deletion, (FIG. 5E). In addition Cxcl12 levels in the BM as well as Cxcl12 protein produced by Mx1+ mesenchymal cells were comparable in control and mutant mice (FIG. 6V and FIG. 8B). Hence we then evaluated whether the HSPC defects observed upon Ext1 deletion in Mx1+ mesenchymal cells were the result of changes in Vcam1 expression. Vcam1 is the ligand for the alpha4-beta1 integrin, Vla4. The Vla4-Vcam1 axis plays a role in HSPC adhesion to their niches and pharmacological inhibition of this interaction results in HSPC mobilization (Craddock et al., 1997; Papayannopoulou et al., 1995). Vcam1 protein levels were significantly reduced in Mx1+ mesenchymal cells in mutant mice (FIG. 7D and FIG. 8C). To determine whether the observed reduction in Vcam1 expression functionally contributed to the mislocalization of HSPCs seen in Ext1-mutant chimeric mice we evaluated how the addition of a Vcam1 neutralizing antibody influenced G-CSF-induced HSPC mobilization in control and mutant animals (FIG. 7E). Mobilized PB from control animals receiving G-CSF together with Vcam1 neutralizing antibody displayed a significant increase in circulating CFU-Cs (FIG. 7F left panels) (Craddock et al., 1997) as well as increased donor chimerism in lethally irradiated congenic recipients post transplantation (FIG. 7G left panels) compared with animals receiving G-CSF alone. However, PB from mutant Ext1 mice mobilized with the combination of G-CSF and Vcam1 neutralizing antibody displayed equivalent number of CFU-Cs (FIG. 7F right panels) and equivalent capacity to reconstitute hematopoiesis in lethally irradiated congenic recipients (FIG. 7G right panels) as G-CSF alone. Comparable results were obtained in response to Vcam1 neutralization without G-CSF administration (FIG. 8D). In summary, deletion of Ext1 and its HSPG products in Mx1+ Skeletal progenitors reduces production of Vcam1 and other adhesion mediators rendering the region less functional as a site of stem cell retention.

Pharmacological Competitive Inhibition of Heparan Sulfate Proteoglycans In Vivo Induces HSPC Mobilization HS mimetics have been shown to induce rapid HSPC mobilization in mice, putatively through competitive inhibition of endogenous HSPGs (Di Giacomo et al., 2012; Frenette and Weiss, 2000; Sweeney et al., 2002). Heparin, a highly sulfated glycosaminoglycan, has been shown to lack the ability to induce mobilization on its own (Frenette and Weiss, 2000). Surprisingly, we observed that heparin administration (100 U/mouse one hour before PB harvest) induces a modest, yet significant increase in the number of circulating HSPCs as measured by CFU assays without a significant change in WBC counts (FIGS. 10A and 10B). Given our observations that the genetic deletion of HS production alters HSPC localization and that heparin is an inexpensive, FDA-approved drug, which competitively inhibits HSPG signaling, we investigated whether it could cooperate with the current G-CSF mobilization regimen (FIG. 9A).

Figures 9A, 9B, 9C, 9D, 9E:
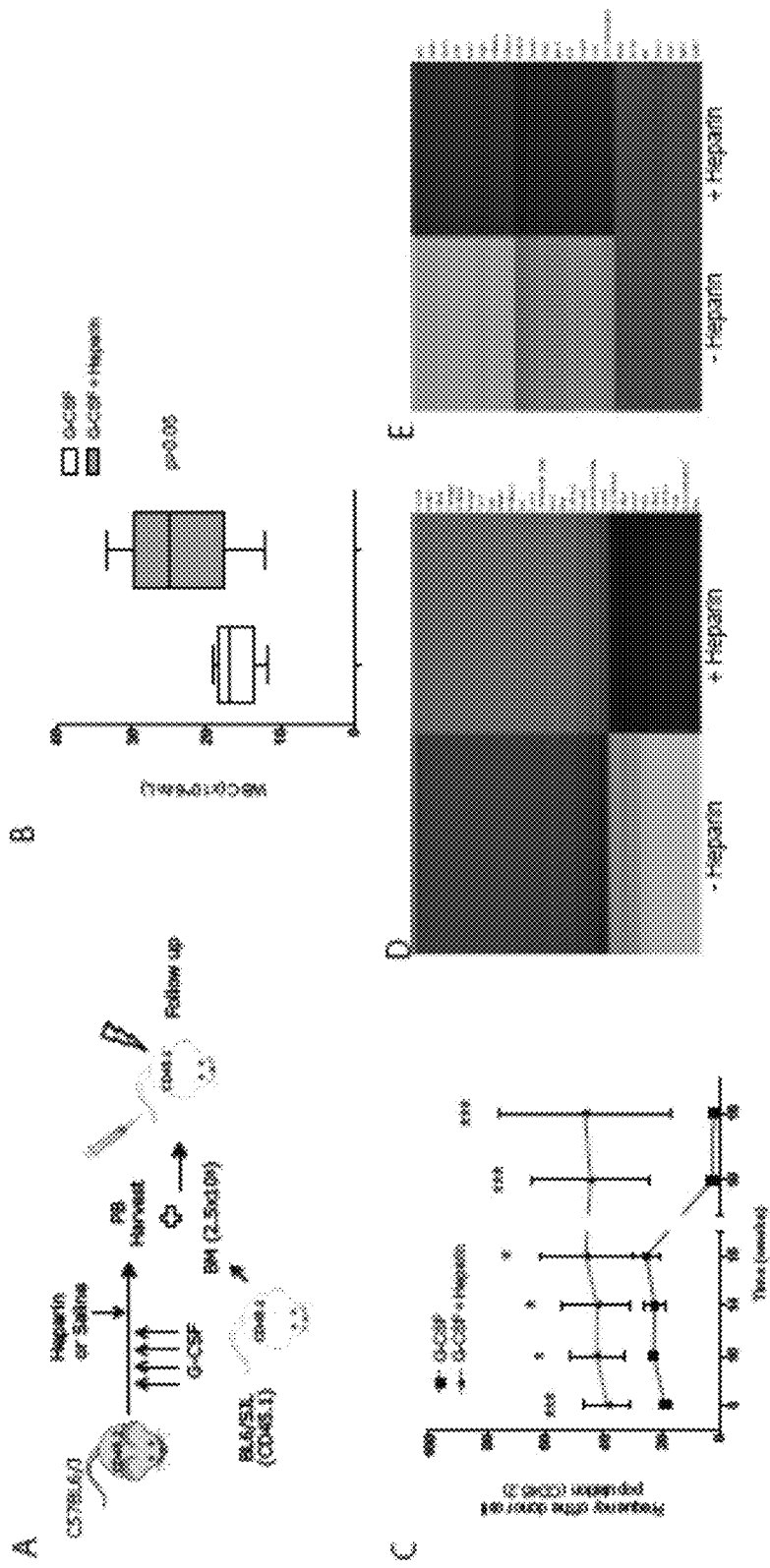
FIGS. 9A, 9B, 9C, 9D, 9E, 9F, 9G, 9H, 9I, 9J, 9K, 9L and 9M demonstrate that pharmacological inhibition of heparan sulfate proteoglycans induces HSPC mobilization.
Figures 9F, 9G, 9H, 9I, 9J, 9K, 9L, 9M:
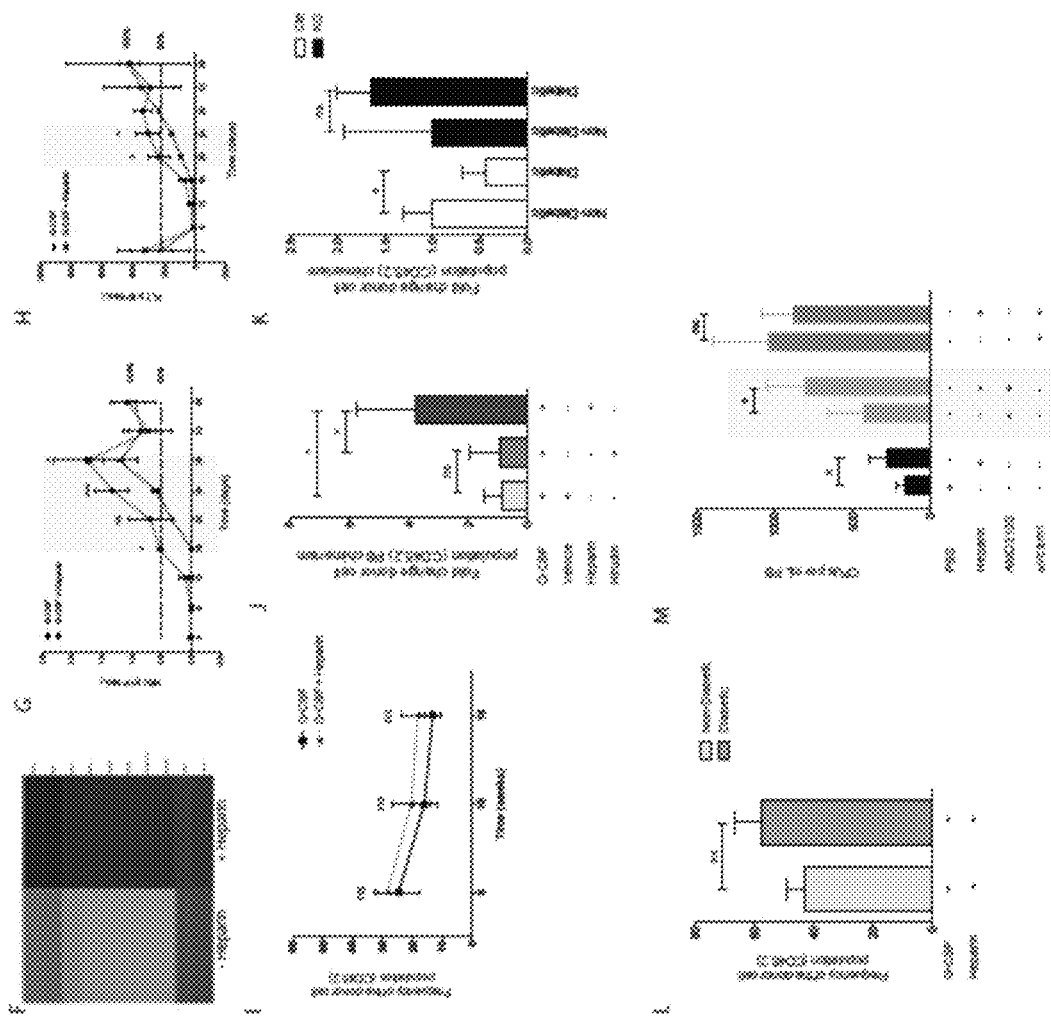
Figures 10A, 10B, 10C, 10D, 10E:
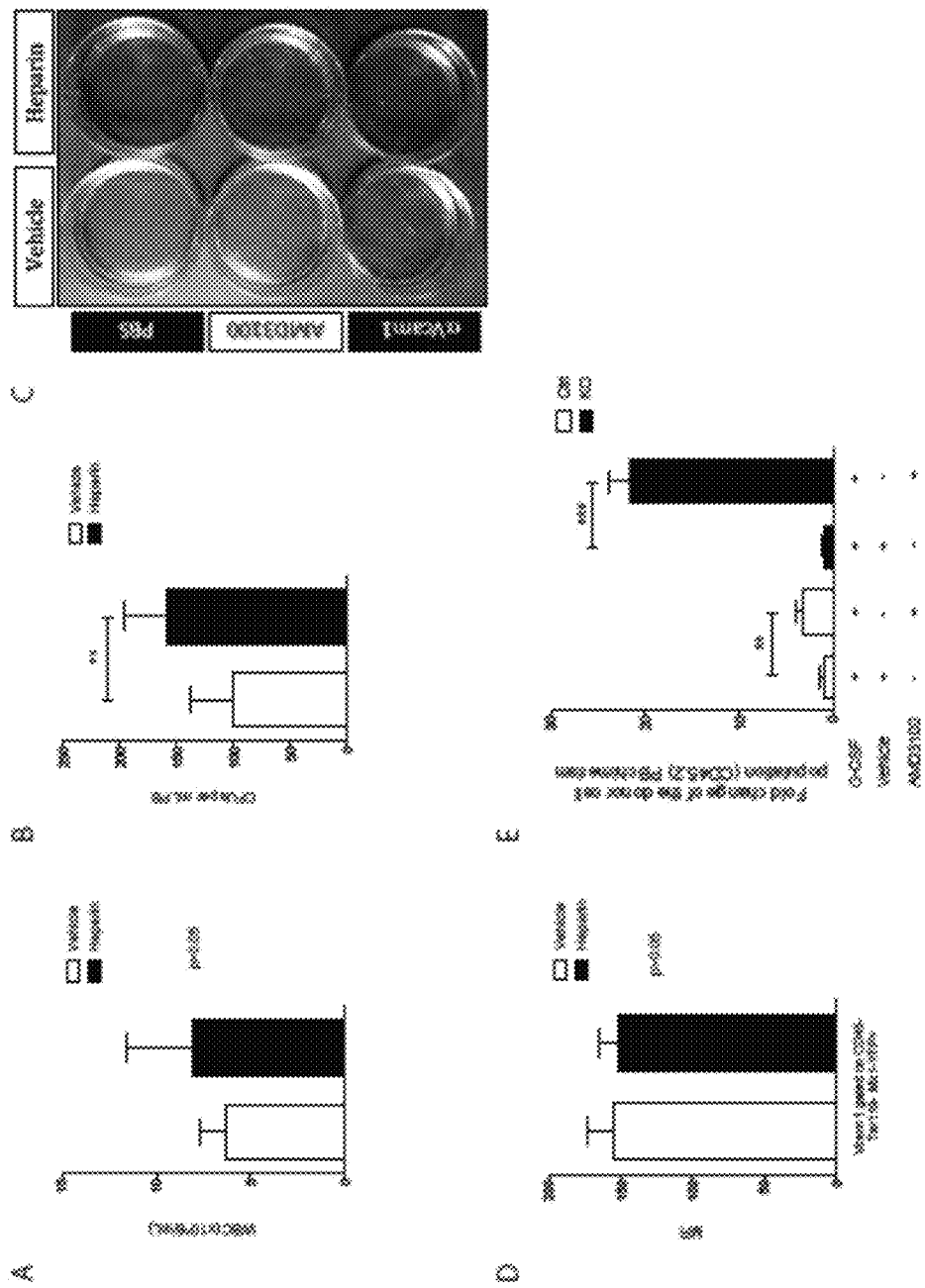
FIGS. 10A, 10B, 10C, 10D and 10E further demonstrate that pharmacological inhibition of heparan sulfate proteoglycans induces HSPC mobilization.

Mice treated with heparin (100 U/mouse one hour before PB harvest) in combination with G-CSF displayed a modest (p>0.05) increase in the WBC count in PB compared to mice treated with G-CSF alone (FIG. 9B). However, the combination of heparin and G-CSF significantly increased the mobilization of long term reconstituting cells as measured by PB competitive transplantation into lethally irradiated congenic mice (FIG. 9C pre-interruption of line graphs). Furthermore, these cells efficiently self-renewed as shown by their ability to engraft secondary recipients (FIG. 9C post-interruption of line graphs). Importantly, administration of heparin and G-CSF mobilize a population of HSCs with a distinct transcriptional signature compared to G-CSF alone (FIGS. 9D, 9E, 9F and Table 3), suggesting that HS competitive inhibition either mobilizes a different population of HSPCs or the mobilization process is sufficiently different to rapidly alter gene expression characteristics. Recovery of neutrophil and platelet counts defines successful engraftment after BM transplantation in clinical settings and time to recovery predicts survival (Davies et al., 2000). Importantly, non-competitive transplantation of PB mobilized by means of co-administration of G-CSF and heparin resulted in four to six day quicker recovery of neutrophils (FIG. 9G) and platelets (FIG. 9H) compared with G-CSF alone. The combination of heparin and G-CSF did not increase HSPC mobilization over G-CSF alone in the Ext1 mutant mice, suggesting that heparin enhances G-CSF-induced mobilization in wild type mice by modulating endogenous HSPGs (FIG. 9I). Also, hirudin, a non-heparin based anticoagulant, did not impact G-CSF-induced HSPC mobilization (FIG. 9J) suggesting that the observed effect was not a consequence of heparin anticoagulation properties.

TABLE 3

Differentially expressed genes in G-CSF plus heparin versus G-CSF alone-mobilized HSPCs.

| Probe | Gene Symbol | Regulation | log-ratio | p-value |
|---|---|---|---|---|
| Cell proliferation | | | | |
| 1416693_at | Foxc2 | DOWN | −1.0062 | 0.0078 |
| 1417155_at | Myon | DOWN | −3.1231 | 0 |
| 1417311_at | Crip2 | UP | 1.5451 | 0.0015 |
| 1417493_at | Bmi1 | UP | 1.4062 | 0.0048 |
| 1417932_at | Il18 | UP | 1.0414 | 0.0025 |
| 1419271_at | Pax6 | DOWN | −1.1718 | 0.0006 |
| 1421066_at | Jak2 | UP | 1.865 | 0 |
| 1421679_a_at | Cdkn1a | UP | 1.224 | 0.0078 |
| 1424638_at | Cdkn1a | UP | 0.9342 | 0.0058 |
| 1424893_at | Ndel1 | UP | 2.2582 | 0 |
| 1426569_a_at | Frk | DOWN | −0.6869 | 0.0055 |
| 1427351_s_at | Igh-6 | UP | 1.136 | 0.0008 |
| 1429615_at | Zfp91 | UP | 1.5046 | 0.0002 |
| 1432459_a_at | Zbtb32 | UP | 2.0602 | 0 |
| 1433489_s_at | Fgfr2 | DOWN | −1.0878 | 0.0029 |
| 1436186_at | E2f8 | UP | 1.6996 | 0.0031 |
| 1437039_at | Cops2 | UP | 1.0689 | 0.0055 |
| 1448834_at | Foxm1 | UP | 1.3727 | 0.0043 |
| 1449044_at | Eef1e1 | DOWN | −1.5725 | 0.0053 |
| 1449145_a_at | Cav1 | UP | 0.6057 | 0.0095 |
| 1449351_s_at | Pdgfc | UP | 0.8549 | 0.0002 |
| 1450923_at | Tgfb2 | DOWN | −0.8205 | 0.0089 |
| 1451651_at | LOC100044885 | UP | 1.8016 | 0.0001 |
| Growth regulation | | | | |
| 1416035_at | Hif1a | UP | 1.4512 | 0.0002 |
| 1418349_at | Hbegf | UP | 1.1121 | 0.0045 |
| 1419988_at | Map3k7 | UP | 1.3737 | 0.0005 |
| 1423753_at | Bambi | UP | 1.0132 | 0.0095 |
| 1427418_a_at | Hif1a | UP | 1.0208 | 0.009 |
| 1433489_s_at | Fgfr2 | DOWN | −1.0878 | 0.0055 |
| 1436736_x_at | D0H4S114 | UP | 1.0423 | 0.0076 |
| 1448183_a_at | Hif1a | UP | 1.0676 | 0.0063 |
| 1451563_at | Emr4 | DOWN | −1.216 | 0.0019 |
| 1451866_a_at | Hgf | UP | 1.1982 | 0.0022 |
| Cell adhesion | | | | |
| 1416808_at | Nid1 | UP | 2.492 | 0.0002 |
| 1418424_at | LOC100044927 | UP | 0.6592 | 0.0033 |
| 1421694_a_at | Vcan | UP | 0.6578 | 0.0034 |
| 1421811_at | LOC640441 | UP | 1.8823 | 0.0038 |
| 1424409_at | Cldn23 | UP | 1.2088 | 0.0049 |
| 1428455_at | Col14a1 | UP | 0.5514 | 0.0061 |
| 1448393_at | Cldn7 | UP | 0.9215 | 0.0046 |
| 1450938_at | Pnn | UP | 1.1524 | 0.0048 |
| 1455056_at | Lmo7 | UP | 1.7536 | 0.0096 |
| 1417123_at | Vav3 | DOWN | −1.0319 | 0 |
| 1417484_at | Ibsp | DOWN | −0.8826 | 0 |
| 1419820_at | Pkhd1 | DOWN | −0.7303 | 0.0006 |
| 1420429_at | Pcdhb3 | DOWN | −0.6167 | 0.004 |

TABLE 3-continued

Differentially expressed genes in G-CSF plus heparin versus G-CSF alone-mobilized HSPCs.

| Probe | Gene Symbol | Regulation | log-ratio | p-value |
|---|---|---|---|---|
| 1420524_a_at | Masp2 | DOWN | −0.6803 | 0.0043 |
| 1421610_at | Cx3cl1 | DOWN | −0.6985 | 0.0011 |
| 1425017_at | Pcdhac1 | DOWN | −1.2135 | 0 |
| 1425935_at | 2900042B11Rik | DOWN | −0.8534 | 0.0008 |
| 1426865_a_at | Ncam1 | DOWN | −2.1841 | 0.0009 |
| 1426911_at | Dsc2 | DOWN | −1.7295 | 0 |
| 1427592_at | Pcdh7 | DOWN | −1.4432 | 0 |
| 1430676_at | Col19a1 | DOWN | −1.8701 | 0.0005 |
| 1436714_at | Lpp | DOWN | −1.2253 | 0 |
| 1437218_at | Fn1 | DOWN | −0.9914 | 0.0001 |
| 1448162_at | Vcam1 | DOWN | −0.6517 | 0.0021 |
| 1449091_at | Cldn8 | DOWN | −1.7035 | 0 |
| 1450758_at | Cntnap2 | DOWN | −1.479 | 0 |
| 1453128_at | Lyve1 | DOWN | −0.9659 | 0.0001 |
| 1453589_a_at | 6820431F20Rik | DOWN | −1.5251 | 0.0076 |

DOWN and UP are referred to heparin treatment. Probes with low intensity and low variance were removed from analysis. FDR (false discovery rate) correction was applied.

Hematopoietic stem cell transplantation remains the gold standard curative therapy for a number of hematological disorders. However, G-CSF mobilization resistance may compromise lifesaving therapy for some individuals. We therefore evaluated whether genetic or pharmacological competitive inhibition of HSPG may facilitate G-CSF-induced HSPC egress from the BM in a murine model of Type I diabetes-induced mobilopathy (Ferraro et al., 2011). G-CSF failed to efficiently mobilize HSPCs in Type I diabetic mice. However, the compromised response to G-CSF was fully corrected in Type I diabetic mice lacking Ext1 expression in Mx1+ mesenchymal cells (FIG. 9K). Furthermore, combination of heparin with G-CSF resulted in normal mobilization of long term reconstituting cells in diabetic animals as measured by PB competitive transplantation into lethally irradiated congenic mice (FIG. 9L). These data demonstrate that functional competitive inhibition of endogenous HSPGs rescues the mobilization abnormalities noted in animals with pharmacologically induced diabetes.

Next, we evaluated whether heparin induced mobilization was abrogated upon Vcam1 inhibition in the absence of G-CSF stimulation since Vcam1 is, at least partially, responsible for the defect observed in the Ext1 mutant mice. Administration of heparin enhanced HSPC mobilization compared to vehicle as measured by CFU assays (FIG. 9M and FIG. 10C). Conversely, co-administration of heparin and Vcam1 neutralizing antibodies failed to improve HSPC mobilization over Vcam1 neutralization alone, suggesting that heparin induces mobilization by modulating Vcam1-dependent adhesion (FIG. 9M and FIG. 10C). However, administration of heparin one hour before PB harvest does not modulate Vcam1 levels in Mx1+ mesenchymal cells (FIG. 10D), suggesting that alternative mechanisms are implicated in the effect of heparin on Vcam1-dependent adhesion such as allosteric interactions affecting the Vcam1-Vla4 interaction as previously shown (Schlesinger et al., 2009). Importantly, our results also show that co-administration of heparin enhances AMD3100-induced mobilization (FIG. 9M, middle shadowed panels and FIG. 10C). Moreover, AMD3100, a Cxcr4 antagonist (Broxmeyer et al., 2005), also augments G-CSF-induced mobilization in Ext1 deficient mice (FIG. 10E), suggesting that the role of HS in HSPC retention is independent of the Cxcl12-Cxcr4 axis.

Mx1+ Mesenchymal Cells Control Engraftment of Transplanted Hematopoietic Stem and Progenitor Cells HSPC engraftment in the BM relies on the efficient evacuation of BM niches, often achieved by means of total body irradiation and high dose chemotherapy (Armitage, 1994). These conditioning methods are toxic and undesirable for patients who do not suffer from a malignancy requiring irradiation or high dose chemotherapy as part of the treatment plan.

Figures 11A, 11B, 11C:
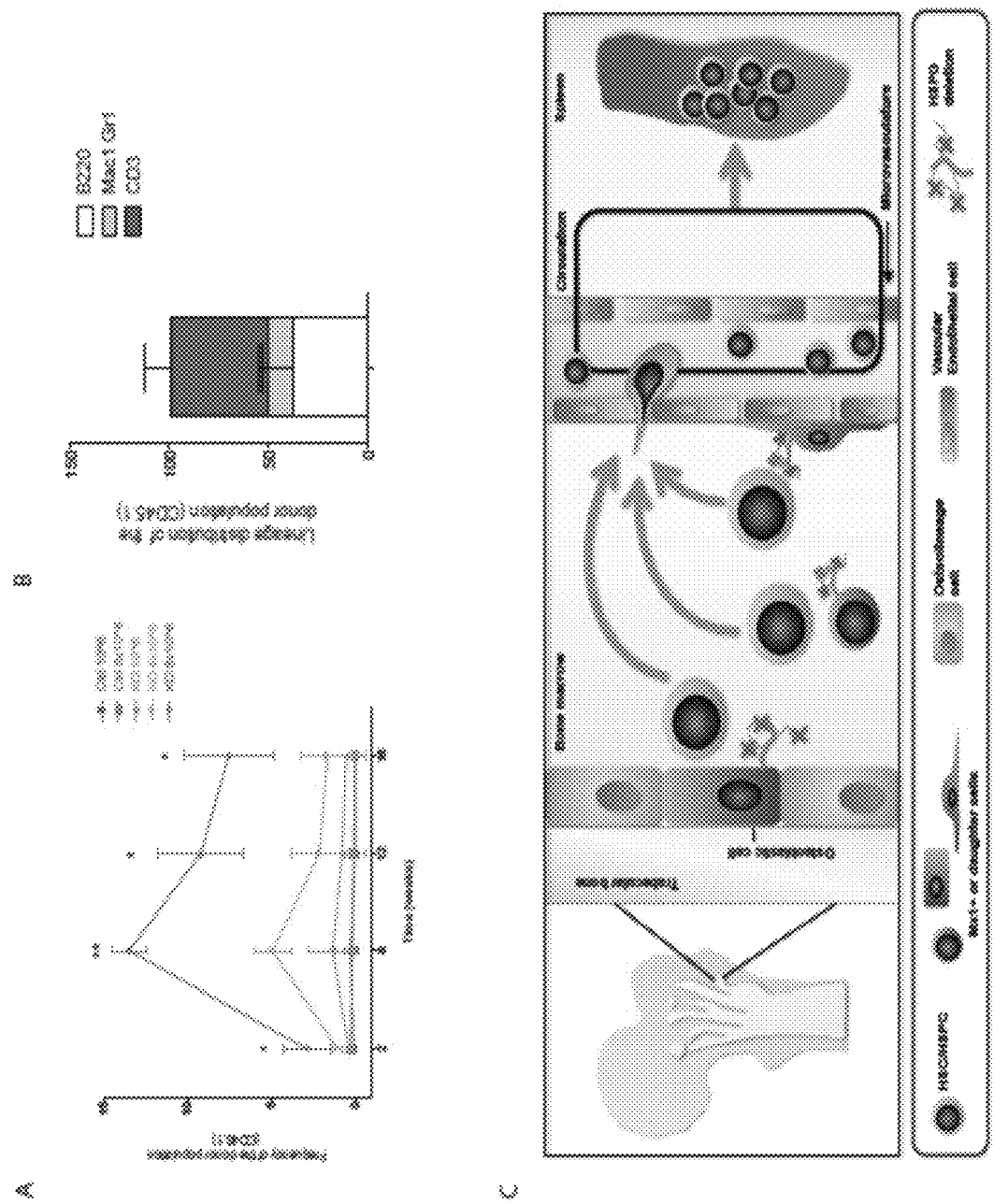
FIGS. 11A, 11B, and 11C demonstrate that Mx1+ mesenchymal cells controls engraftment of transplanted HSPCs.

We evaluated whether abrogation of Ext1 in Mx1+ mesenchymal cells may enable engraftment without cytotoxic conditioning. Three weeks after pIpC induction, control and mutant mice were transplanted with congenic CD45.1 BM cells and followed for 16 weeks. Notably, while control animals failed to engraft independently of the cell dose transplanted, mutant mice showed a significant increase in engraftment in a dose-dependent manner throughout the course of the transplant (FIG. 11A). The engrafting cells demonstrated long-term multi-lineage reconstitution (FIG. 11B). Hence, Mx1+ mesenchymal cell production of HSPGs modulates the process of HSPC engraftment in the BM suggesting that targeting HS may provide a means of enabling engraftment without cytotoxic pre-conditioning.

Discussion

Secreted and membrane bound HSPGs have been implicated in numerous biological processes in organisms from *Drosophila* to mammals creating the microenvironment necessary for heterologous cell interaction to create and maintain tissues (Kraushaar et al., 2012; Vied et al., 2012). In hematopoiesis, several prior reports have indicated the importance of HSPG. For example, HS mimetics were shown to induce hematopoietic stem/progenitor cell (HSPC) mobilization (Di Giacomo et al., 2012; Frenette and Weiss, 2000; Sweeney et al., 2002), while overexpression of the HS-cleaving enzyme heparanase, resulted in HSPCs accumulating in the BM (Spiegel et al., 2008). Moreover, glypican-3, a cell surface HSPG, inhibits the extracellular dipeptidyl peptidase CD26 (Khurana et al., 2013), which affects HSPC homing and egress from the BM (Christopherson et al., 2004). Here, we present evidence that skeletal stem/progenitor cell production of HS control HSPC bone marrow retention, can be inhibited to mobilize more potent HSPC even in settings of mobilization resistance and may be targeted to enable non-toxic conditioning for HSPC engraftment. Through these data we show that Mx1-expressing mesenchymal cells and/or their descendants comprise a population of BM cells that participate in a niche for hematopoietic stem cells (FIG. 11C).

Manipulation of the endogenous HSPGs produced by skeletal stem/progenitor cells can alter localization sufficiently to be of relevance to clinically important issues. First, co-administration of G-CSF and heparin mobilized qualitatively distinct HSPC with more rapid hematopoietic reconstitution and increased secondary transplant ability. These data suggest that combined use of these agents may favor the collection of highly potent HSPCs for transplantation. Second, heparin or Ext1 deletion enhanced G-CSF induced HSPC mobilization even in the setting of G-CSF resistance induced by a diabetic phenotype. Parenthetically, the pathophysiologic basis for the diabetic phenotype includes neuropathy. Since the deletion of Ext1 prevents the development of the mobilization defect, it is intriguing to consider whether HS participates in the neuropathic complications of diabetes. Finally, Ext1 deletion provided a context in which infused HSPC could engraft and achieve levels of chimerism meaningful for some non-malignant clinical conditions. It should be noted that the level of chimerism was more than double that seen when AMD3100 was used as a conditioning regimen by others using 5-fold more bone marrow cells (Chen et al., 2006) Since the induction of Ext1 deletion in animals did not compromise the apparent well-being of the animals over the 3 week interval prior to infusion of the cells, inhibiting Ext1 function may be a strategy to accomplish HSPC engraftment without cytotoxic conditioning. This issue is of increasing importance with the improved success of genetically modifying HSPC for non-malignant diseases. (Aiuti et al., 2013; Biffi et al., 2013).

Experimental Procedures for Example 4

Mice

Ext1flox/flox mice were previously described (Inatani et al., 2003). C57BL/6J, B6.SJL-Ptprca Pep3b/BoyJ (B6.SJL), Mx1-Cre (B6.Cg-Tg(Mx1-cre)1Cgn/J), Rosa26-loxP-stop-loxP-EYFP (Rosa-YFP, B6.129X1-Gt(ROSA)26Sortm1(EYFP)Cos/J) and Col2.3-GFP (B6.Cg-Tg(Col1a1*2.3-GFP)1Rowe/J) mice were purchased from Jackson laboratory. Six to twelve week old male mice were used. Polyinosinic-polycytidylic acid (pIpC) was obtained from Amersham (GE-Healthcare Life Sciences) and administered by intraperitoneal (i.p.) injection at a dose of 25 mg/kg of total body weight (TBW) in PBS every other day for four days. Harvard University Institutional Animal Care and Use Committee (IACUC) and the Subcommittee on Research Animal Care of the Massachusetts General Hospital approved all animal work.

Flow Cytometry Analysis

Immunophenotypic characterization of the hematopoietic and mesenchymal compartments was performed as previously described (Gurumurthy et al., 2010). For details see supplementary information. Vcam1 and Cxcl12 protein levels were evaluated with an anti-Vcam1-APC and an anti-Cxcl12-APC antibody respectively and the corresponding isotype controls (R&D Systems). All data collection was performed on an LSRII or FACS Aria II (Beckon Dickinson) and data analysis was performed with FlowJo (Treestar).

Transplantation Assays

For non-competitive BM transplantation, to create the chimeras described in FIG. 1a, one million whole BM cells from B6.SJL (CD45.1) mice were transplanted into lethally irradiated (9.5 Gy from a Cesium source 4-24 hours before transplantation) Ext1-loxP/loxP-Mx1cre (CD45.2) recipients six-to-eight weeks before pIpC administration. Neutrophil and platelet recovery assay was performed as previously described (Hoggatt et al., 2013). Briefly, 3 million mobilized PB mononuclear cells (MNC) from C57BL/6J (CD45.2) mice were transplanted into lethally irradiated B6.SJL (CD45.1) mice and followed up for at least 36 days. For transplantation without cytotoxic conditioning, 1, 4 or 8 million whole BM cells from B6.SJL mice were transplanted into Ext1-loxP/loxP-Mx1cre recipients three weeks after pIpC administration. For competitive transplantation of mobilized peripheral blood (PB), 150 ul of PB (CD45.2) was mixed with 2×10⁵ congenic BM support cells and injected into lethally irradiated CD45.1 recipients. Cells were infused via lateral tail vein injection. Engraftment was monitored at 4-week intervals by FACS analysis.

Intravital Microscopy

In vivo imaging of HSPCs in the calvaria BM cavity and data analysis was performed as previously described (Lo Celso et al., 2009). Briefly, FACS-sorted HSCs were stained in PBS for 15 min at 37° C. with DiD (Invitrogen) using a 1:200 dilution and injected into lethally irradiated Ext1 control and mutant Col2.3-GFP+ recipients. Mice were imaged 24 hours later. Distance between HSCs, GFP+ osteoblastic cells and bone were measured using Image J software.

HSC Mobilization and Blood Collection

Recombinant human G-CSF (Neupogen, Filgrastrim) was administered at 125 ug/kg of TBW every 12 hours for eight consecutive injections. Heparin Sodium (APP Pharmaceuticals) was injected i.p. at a single dose of 100 U. Hirudin was used at 40 mg/kg of TBW in a single dose. Vcam1 neutralizing antibody and the corresponding isotype control (Rat IgG2a, k) were injected intravenously at 2 mg/kg of TBW every day for three doses and PB samples were obtained through retro-orbital bleeding the day following the last injection. AMD3100 was administered subcutaneously at a single dose of 5 mg/kg TBW. PB samples were obtained through retro-orbital bleeding 3 hours after the last injection of G-CSF and 1 hour after Heparin, AMD3100, or Hirudin injection.

Diabetic Mouse Model

Diabetes was induced in 4 to 6 week-old C57BL/6J or Ext1-loxP/loxP-Mx1cre male mice as previously described (Ferraro et al., 2011). Only animals with glucose values higher than 300 mg/dl were used for experiments.

Statistical Analysis

Unpaired, two-tailed Student's t test or one-way ANOVA followed by the appropriate post-hoc test were used. Data have been plotted as average±SD for samples following a normal (Gaussian) distribution. Alternatively, Mann-Whitney U test was used and data have been plotted as median±IQR (interquartile range). Statistical significance is indicated as follows: ns: non-significant; $*P<0.05$; $P<0.01$; $*P<0.001$.

Flow Cytometry Analysis

Hematopoietic stem and progenitor cells were identified by lineage markers as well as the following markers conjugated to fluorochromes: c-Kit-APC, CD34-FITC, CD16/32-PE-Cy7, CD127-APC-Cy7, CD48-PacificBlue, CD150-PE and Sca-1-PE-Cy7. Lineage staining was performed with a cocktail of biotinylated anti-mouse antibodies against Mac-1a (CD11b), Gr-1 (Ly-6G/C), Ter119 (Ly-76), CD3, CD4, CD8a (Ly-2) and B220 followed by detection with streptavidin conjugated to Pacific Orange (Invitrogen). For congenic strain discrimination, anti-CD45.1-PE-Cy7 and anti-CD45.2-FITC antibodies were used. Mature lymphoid and myeloid cells were identified by: B220-PacificBlue (B-cells), Mac-1a-PE and Gr1-APC or FITC (myeloid cells) and CD3-PE-Cy5 or Alexa700 (T-Cells).

Evaluation of circulating neutrophils was performed as previously described (Casanova-Acebes et al., 2013). Neutrophils were identified by their expression of Mac1 (PE-Cy7), Gr1 (FITC), CD62 (APC) and Cxcr4 (PE) as well as the lack of expression of B220 (PacificBlue), CD3, CD4, CD8, Ter119, CD115, CD117, CD49b and F4/80 (all biotinylated and followed by detection with streptavidin conjugated to Pacific Orange). For cell cycle analysis, bone marrow cells were first stained for HSC cell surface markers (Lineage-APC-Cy7, c-Kit-APC, Sca-1-PE-Cy7, CD48-PE and CD150-PE-Cy5), fixed and permeabilized using the BD Cytofix/Cytoperm Kit (BD Biosciences) and stained with Ki-67-FITC (BD Biosciences) for 45 min at 4° C. followed by DNA staining with DAPI (2 pg/mL)(Invitrogen). For apoptosis, 7-AAD and AnnexinV-FITC (BD Biosciences) stains were used according to manufacturer's instructions.

Mesenchymal stem cells were identified by the expression of CD105 (PE), CD140 (APC), Sca1 (PacificBlue) and Mx1 (Rosa26-loxP-stop-loxP-EYFP) amongst the CD45−Ter119− (both PE-Cy7) BM cells (Chan et al., 2009; Morikawa et al., 2009; Park et al., 2012).

Evaluation of heparan sulfate production upon Ext1 deletion in Mx1+ mesenchymal cells was performed with the anti-HS antibody 10E4 (Seikagaku Corporation) followed by incubation with a PE-conjugated anti-mouse IgM according to manufacturer's instruction.

All antibodies were purchased from BD Biosciences, BioLegend or eBiosciences unless stated otherwise.

Complete Blood Count (CBC)

Blood counts were performed with the automatic Vetscan HM2 (Abaxis).

Colony Forming Unit (CFU) Assays

CFU assays were performed as previously described (Ferraro et al., 2011). Equal volumes of PB (50 to 200 juL depending upon the experiment) were subjected to red blood cell lysis with ammonium-chloride-potassium buffer, resuspended in 4 ml of methocult M3434 (Stem Cell Technologies), plated in 35 mm culture dishes (1 mL/dish) and cultured at 37° C. for 8 days before scoring for colony formation.

MicroCT

Microarchitecture of cancellous bone and cortical bone was analyzed in femora by high-resolution micro-computed tomography (resolution 7 Um, microCT35, Scanco Medical AG, Bassersdorf, Switzerland). Bones were scanned at energy level of 55 kVp, and intensity of 145 jA. The microCT35 is calibrated weekly using a phantom provided by Scanco. Cancellous bone volume fraction and microarchitecture were evaluated in the secondary spongiosa, starting at 0.15 mm proximal to the distal femoral growth plate, and extending proximally 3.2 mm. Approximately 460 consecutive slices were made at 7 jm interval at the distal end of the growth plate and extending in a proximal direction, and 300 contiguous slices were selected for analysis. A fixed threshold at 29% of maximal gray scale value was used to separate bone from soft tissue in all samples. Scans for the cortical region were measured at the mid-point of each femur, with an isotropic voxel size of 7 jm. For mid-shaft analysis, the cortical shell was contoured by user-defined threshold at 35% of maximal gray scale and iterated through all 86 slices. All scans were analyzed using manufacturer software (Scanco, version 4.05). Acquisition and analysis of microCT data were performed in accordance with recently published guidelines (Bouxsein et al., 2010).

Bone Histomorphometry

Control and mutant mice were lethally irradiated and transplanted with 106 BM cells at 6 weeks of age. Ext1 deletion was induced 3 weeks post transplantation by pIpC injection. Static and dynamic histomorphometric measurements were analyzed between mutant and control mice at 12 weeks of age (6 weeks after BM transplantation). Mice were injected with 20 mg/kg calcein and demeclocycline i.p. 7 days and 2 days, respectively, before sample collection. Tibiae were analyzed as described previously (Liu et al., 2012) and standard nomenclature was used for description of parameters (Dempster et al., 2013).

Bone Histology

Histological preparation and analysis was performed as previously described (Guo et al., 2010).

RNA isolation, quantitative real-time PCR and microarray gene expression profiling YFP+CD45−Ter119−PI− (Propidium iodide) cells from Ext1−loxP/loxP−Mx1cre+−Rosa−YFP+ and Ext1−loxP/loxP−Mx1cre+−Rosa−YFP+ mice were FACS sorted directly into Trizol Reagent (Invitrogen) and mRNA was extracted following manufacturer's instruction. cDNA synthesis was performed with the RET- ROscript reverse transcription kit (Ambion). Real-time PCR was performed using SYBR green (Applied Biosystems) technology according to manufacturer's instruction. Primers used for SYBR-Green real-time PCR in the present study have been previously published (Ding and Morrison, 2013; Mendez-Ferrer et al., 2010; Pomyje et al., 2001; Zerfaoui et al., 2008) (all 5' to 3'):

```
VCAM1:
                                          (SEQ ID NO: 1)
TGCCGAGCTAAATTACACATTG
and (SEQ ID NO: 2)
CCTTGTGGAGGGATGTACAGA.

CXCL12:
                                          (SEQ ID NO: 3)
TGCATCAGTGACGGTAAACCA
and (SEQ ID NO: 4)
CACAGTTTGGAGTGTTGAGGAT, Angpt1:
                                          (SEQ ID NO: 5)
GCGCTGGCAGTACAATGACAGT
and (SEQ ID NO: 6)
ATTTTCCATCACATGCTCCAGAT.

SCF1:
                                          (SEQ ID NO: 7)
CCCTGAAGACTCGGGCCTA
and (SEQ ID NO: 8)
CAATTACAAGCGAAATGAGAGCC.

EXT-1:
                                          (SEQ ID NO: 9)
GCCCTTTTGTTTATTTTGG
and (SEQ ID NO: 10)
TCTTGCCTTTGTAGATGCTC.

Frizzled-1:
                                          (SEQ ID NO: 11)
CAGCAGTACAACGGCGAAC
and (SEQ ID NO: 12)
GTCCTCCTGATTCGTGTGGC.
```

For micro-array analysis, PB from mice mobilized with G-CSF alone or in combination with heparin was collected as described in the main body of the text. Mononuclear cells were isolated by means of gradient centrifugation, stained for HSPC markers (Linegae−, c-kit+, Sca-1+) and sorted directly into Trizol (Invitrogen). RNA was extracted according to the manufacturer's instructions. Amplified cDNA was prepared from total RNA using the NuGEN Ovation V2 amplification system following manufacturer's instruction. Amplified cDNA was purified using the Zymo Research DNA Clean & Concentrator system. The purified cDNA was hybridized to the Mouse430A microarray chip following manufacturer's instruction. Data were analyzed using Nexus Expression v2.0 (Biodiscovery). Low variance, low intensity and false discovery (FDR) rate correction was applied for data analysis.

Western Blotting

YFP+CD45−Ter119−PI− (Propidium iodide) cells from Ext1−loxP/loxP−Mx1cre+−Rosa−YFP+ and Ext1−loxP/loxP−Mx1cre+−Rosa−YFP+ mice were FACS sorted and expanded ex vivo for 10 days in alpha-MEM media without ribonucleosides and deoxyribonucleosides and supplemented with 20% FBS, 2.2 g/L sodium bicarbonate and 2.5 mL of 2-mercaptoethanol (100×, Millipore ES-007-E). Cells were lysed in RIPA buffer (Boston Bioproducts) supplemented with protease and phosphate inhibitors (10 mM NaF, 1 mM Na3VO4 and 1× protease cocktail (Roche). Protein extracts (20 jug) were resolved by SDS-PAGE on a 12.5% polyacrylamide gel, immunoblotted onto nitrocellulose membranes (Bio-Rad) and visualized by chemiluminescence using standard protocols. The following antibodies were used: anti-Ext1 (Sigma, wh0002131m1) and anti-rabbit Gapdh (abeam, ab9485). Films were scanned and densitometric measurements were performed using ImageJ software (NIH). The optical density of Ext1 bands was normalized to that of Gapdh. The level of Ext1 protein was expressed as the ratio of its optical density relative to that of Gapdh.

Example 4 References

1. Aiuti, A., Blasco, L., Scaramuzza, S., Ferrua, F., Cicalese, M. P., Baricordi, C., Dionisio, F., Calabria, A., Giannelli, S., Castiello, M. C., et al. (2013). Lentiviral hematopoietic stem cell gene therapy in patients with Wiskott-Aldrich syndrome. Science 341, 1233151.
2. Akiyama, T., Kamimura, K., Firkus, C., Takeo, S., Shimmi, O., and Nakato, H. (2008). Dally regulates Dpp morphogen gradient formation by stabilizing Dpp on the cell surface. Dev Biol 313, 408-419.
3. Arai, F., Hirao, A., Ohmura, M., Sato, H., Matsuoka, S., Takubo, K., Ito, K., Koh, G. Y., and Suda, T. (2004). Tie2/angiopoietin-1 signaling regulates hematopoietic stem cell quiescence in the bone marrow niche. Cell 118, 149-161.
4. Armitage, J. O. (1994). Bone marrow transplantation. N Engl J Med 330, 827-838.
5. Biffi, A., Montini, E., Lorioli, L., Cesani, M., Fumagalli, F., Plati, T., Baldoli, C., Martino, S., Calabria, A., Canale, S., et al. (2013). Lentiviral hematopoietic stem cell gene therapy benefits metachromatic leukodystrophy. Science 341, 1233158.
6. Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human hematopoietic stem and progenitor cells with AMD3100, a CXCR4 antagonist. J Exp Med 201, 1307-1318.
7. Casanova-Acebes, M., Pitaval, C., Weiss, L. A., Nombela-Arrieta, C., Chevre, R., N, A. G., Kunisaki, Y., Zhang, D., van Rooijen, N., Silberstein, L. E., et al. (2013). Rhythmic modulation of the hematopoietic niche through neutrophil clearance. Cell 153, 1025-1035.
8. Chen, J., Larochelle, A., Fricker, S., Bridger, G., Dunbar, C. E., and Abkowitz, J. L. (2006). Mobilization as a preparative regimen for hematopoietic stem cell transplantation. Blood 107, 3764-3771.
9. Christopherson, K. W., 2nd, Hangoc, G., Mantel, C. R., and Broxmeyer, H. E. (2004). Modulation of hematopoietic stem cell horning and engraftment by CD26. Science 305, 1000-1003.
10. Craddock, C. F., Nakamoto, B., Andrews, R. G., Priestley, C. V., and Papayannopoulou, T. (1997). Antibodies to VLA4 integrin mobilize long-term repopulating cells and augment cytokine-induced mobilization in primates and mice. Blood 90, 4779-4788.

11. Davies, S. M., Kollman, C., Anasetti, C., Antin, J. H., Gajewski, J., Casper, J. T., Nademanee, A., Noreen, H., King, R., Confer, D., et al. (2000). Engraftment and survival after unrelated-donor bone marrow transplantation: a report from the national marrow donor program. Blood 96, 4096-4102.

12. Di Giacomo, F., Lewandowski, D., Cabannes, E., Nancy-Portebois, V., Petitou, M., Fichelson, S., and Romeo, P. H. (2012). Heparan sulfate mimetics can efficiently mobilize long-term hematopoietic stem cells. Haematologica 97, 491-499.

13. Ding, L., and Morrison, S. J. (2013). Haematopoietic stem cells and early lymphoid progenitors occupy distinct bone marrow niches. Nature 495, 231-235.

14. Ding, L., Saunders, T. L., Enikolopov, G., and Morrison, S. J. (2012). Endothelial and perivascular cells maintain haematopoietic stem cells. Nature 481, 457-462.

15. Ferraro, F., Lymperi, S., Mendez-Ferrer, S., Saez, B., Spencer, J. A., Yeap, B. Y., Masselli, E., Graiani, G., Prezioso, L., Rizzini, E. L., et al. (2011). Diabetes impairs hematopoietic stem cell mobilization by altering niche function. Sci Transl Med 3, 104ra101.

16. Frenette, P. S., and Weiss, L. (2000). Sulfated glycans induce rapid hematopoietic progenitor cell mobilization: evidence for selectin-dependent and independent mechanisms. Blood 96, 2460-2468.

17. Gordon, M. Y., Riley, G. P., Watt, S. M., and Greaves, M. F. (1987). Compartmentalization of a haematopoietic growth factor (GM-CSF) by glycosaminoglycans in the bone marrow microenvironment. Nature 326, 403-405.

18. Greenbaum, A., Hsu, Y. M., Day, R. B., Schuettpelz, L. G., Christopher, M. J., Borgerding, J. N., Nagasawa, T., and Link, D. C. (2013). CXCL12 in early mesenchymal progenitors is required for haematopoietic stem-cell maintenance. Nature 495, 227-230.

19. Gurumurthy, S., Xie, S. Z., Alagesan, B., Kim, J., Yusuf, R. Z., Saez, B., Tzatsos, A., Ozsolak, F., Milos, P., Ferrari, F., et al. (2010). The Lkb1 metabolic sensor maintains haematopoietic stem cell survival. Nature 468, 659-663.

20. Hoggatt, J., Mohammad, K. S., Singh, P., Hoggatt, A. F., Chitteti, Speth, J. M., Hu, P., Poteat, B. A., Stilger, K. N., Ferraro, F., et al. (2013). Differential stem- and progenitor-cell trafficking by prostaglandin E2. Nature 495, 365-369.

21. Inatani, M., Irie, F., Plump, A. S., Tessier-Lavigne, M., and Yamaguchi, Y. (2003). Mammalian brain morphogenesis and midline axon guidance require heparan sulfate. Science 302, 1044-1046.

22. Khurana, S., Margamuljana, L., Joseph, C., Schouteden, S., Buckley, S. M., and Verfaillie, C. M. (2013). Glypican-3-mediated inhibition of CD26 by TFPI: a novel mechanism in hematopoietic stem cell homing and maintenance. Blood 121, 2587-2595.

23. Kraushaar, D. C., Rai, S., Condac, E., Nairn, A., Zhang, S., Yamaguchi, Y., Moremen, K., Dalton, S., and Wang, L. (2012). Heparan sulfate facilitates FGF and BMP signaling to drive mesoderm differentiation of mouse embryonic stem cells. J Biol Chem 287, 22691-22700.

24. Kuhn, R., Schwenk, F., Aguet, M., and Rajewsky, K. (1995). Inducible gene targeting in mice. Science 269, 1427-1429.

25. Lo Celso, C., Fleming, H. E., Wu, J. W., Zhao, C. X., Miake-Lye, S., Fujisaki, J., Cote, D., Rowe, D. W., Lin, C. P., and Scadden, D. T. (2009). Live-animal tracking of individual haematopoietic stem/progenitor cells in their niche. Nature 457, 92-96.

26. McCormick, C., Leduc, Y., Martindale, D., Mattison, K., Esford, L. E., Dyer, A. P., and Tufaro, F. (1998). The putative tumour suppressor EXT1 alters the expression of cell-surface heparan sulfate. Nat Genet 19, 158-161.

27. Mendez-Ferrer, S., Michurina, T. V., Ferraro, F., Mazloom, A. R., Macarthur, B. D., Lira, S. A., Scadden, D. T., Ma'ayan, A., Enikolopov, G. N., and Frenette, P. S. (2010). Mesenchymal and haematopoietic stem cells form a unique bone marrow niche. Nature 466, 829-834.

28. Mercier, F. E., Ragu, C., and Scadden, D. T. (2012). The bone marrow at the crossroads of blood and immunity. Nat Rev Immunol 12, 49-60.

29. Papayannopoulou, T., Craddock, C., Nakamoto, B., Priestley, G. V., and Wolf, N. S. (1995). The VLA4/VCAM-1 adhesion pathway defines contrasting mechanisms of lodgement of transplanted murine hemopoietic progenitors between bone marrow and spleen. Proc Natl Acad Sci USA 92, 9647-9651.

30. Park, D., Spencer, J. A., Koh, B. I., Kobayashi, T., Fujisaki, J., Clemens, T. L., Lin, C. P., Kronenberg, H. M., and Scadden, D. T. (2012). Endogenous bone marrow MSCs are dynamic, fate-restricted participants in bone maintenance and regeneration. Cell Stem Cell 10, 259-272.

31. Roberts, R., Gallagher, J., Spooncer, E., Allen, T. D., Bloomfield, F., and Dexter, T. M. (1988). Heparan sulphate bound growth factors: a mechanism for stromal cell mediated haemopoiesis. Nature 332, 376-378.

32. Schlesinger, M., Simonis, D., Schmitz, P., Fritzsche, J., and Bendas, G. (2009). Binding between heparin and the integrin VLA-4. Thromb Haemost 102, 816-822, 33. Spiegel, A., Zcharia, E., Vagima, Y., Itkin, T., Kalinkovich, A., Dar, A., Kollet, O., Netzer, N., Golan, K., Shafat, I., et al. (2008). Heparanase regulates retention and proliferation of primitive Sca-1+/c-Kit+/Lin− cells via modulation of the bone marrow microenvironment. Blood 111, 4934-4943.

34. Sweeney, E. A., Lortat-Jacob, H., Priestley, G. V., Nakamoto, B., and Papayannopoulou, T. (2002). Sulfated polysaccharides increase plasma levels of SDF-1 in monkeys and mice: involvement in mobilization of stem/progenitor cells. Blood 99, 44-51.

35. Vied, C., Reilein, A., Field, N. S., and Kalderon, D. (2012). Regulation of stem cells by intersecting gradients of long-range niche signals. Dev Cell 23, 836-848.

36. Bouxsein, M. L., Boyd, S. K., Christiansen, B. A., Guldberg, R. E., Jepsen, K. J., and Muller, R. (2010). Guidelines for assessment of bone microstructure in rodents using micro-computed tomography. J Bone Miner Res 25, 1468-1486.

37. Casanova-Acebes, M., Pitaval, C., Weiss, L. A., Nombela-Arrieta, C., Chevre, R., N, A. G., Kunisaki, Y., Zhang, D., van Rooijen, N., Silberstein, L E., et al. (2013). Rhythmic modulation of the hematopoietic niche through neutrophil clearance. Cell 153, 1025-1035.

38. Chan, C. K., Chen, C. C., Luppen, C. A., Kim, J. B., DeBoer, A. T., Wei, K., Helms, J. A., Kuo, C. J., Kraft, D. L., and Weissman, I. L. (2009). Endochondral ossification is required for haematopoietic stem-cell niche formation. Nature 457, 490-494.

39. Dempster, D. W., Compston, J. E., Drezner, M. K., Glorieux, F. H., Kanis, J. A., Malluche, H., Meunier, P. J., Ott, S. M., Recker, R. R., and Parfitt, A. M. (2013). Standardized nomenclature, symbols, and units for bone histomorphometry: a 2012 update of the report of the ASBMR Histomorphometry Nomenclature Committee. J Bone Miner Res 28, 2-17.

40. Ding, L., and Morrison, S. J. (2013). Haematopoietic stem cells and early lymphoid progenitors occupy distinct bone marrow niches. Nature 495, 231-235.
41. Ferraro, F., Lymperi, S., Mendez-Ferrer, S., Saez, B., Spencer, J. A., Yeap, B. Y., Masselli, E., Graiani, G., Prezioso, L., Rizzini, et al. (2011). Diabetes impairs hematopoietic stem cell mobilization by altering niche function. Sci Transl Med 3, 104ra101.
42. Guo, J., Lu, M., Yang, D., Bouxsein, M. L., Thomas, C. C., Schipani, E., Bringhurst, F. R., and Kronenberg, H. M. (2010). Phospholipase C signaling via the parathyroid hormone (PTH)/PTH-related peptide receptor is essential for normal bone responses to PTH. Endocrinology 151, 3502-3513.
43. Liu, Y., Berendsen, A. D., Jia, S., Lotinun, S., Baron, R., Ferrara, N., and Olsen, B. R. (2012). Intracellular VEGF regulates the balance between osteoblast and adipocyte differentiation. J Clin Invest 122, 3101-3113.
44. Mendez-Ferrer, S., Michurina, T. V., Ferraro, F., Mazloom, A. R., Macarthur, B. D., Lira, S. A., Scadden, D. T., Ma'ayan, A., Enikolopov, O. N., and Frenette, P. S. (2010). Mesenchymal and haematopoietic stem cells form a unique bone marrow niche. Nature 466, 829-834.
45. Morikawa, S., Mabuchi, Y., Kubota, Y., Nagai, Y., Niibe, K., Hiratsu, E., Suzuki, S., Miyauchi-Hara, C., Nagoshi, N., Sunabori, T., et al. (2009). Prospective identification, isolation, and systemic transplantation of multipotent mesenchymal stem cells in murine bone marrow. J Exp Med 206, 2483-2496.
46. Park, D., Spencer, J. A., Koh, B. L, Kobayashi, T., Fujisaki, J., Clemens, T. L., Lin, C. P., Kronenberg, H. M., and Scadden, D. T. (2012). Endogenous bone marrow MSCs are dynamic, fate-restricted participants in bone maintenance and regeneration. Cell Stem Cell 10, 259-272.
47. Pomyje, J., Zivny, J. H., Stopka, T., Simak, J., Vankova, H., and Necas, E. (2001). Angiopoietin-1, angiopoietin-2 and Tie-2 in tumour and non-tumour tissues during growth of experimental melanoma. Melanoma Res 11, 639-643.
48. Zerfaoui, M., Suzuki, Y., Naura, A. S., Hans, C. P., Nichols, C., and Boulares, A. H. (2008). Nuclear translocation of p65 NF-kappaB is sufficient for VCAM-1, but not ICAM-1, expression in TNF-stimulated smooth muscle cells: Differential requirement for PARP-1 expression and interaction. Cell Signal 20, 186-194.

All patents and other publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method of conditioning a subject for engraftment of transplanted hematopoietic stem cells and/or progenitor cells in the absence of cytotoxic conditioning, comprising administering to the subject a C-X-C chemokine receptor type 2 (CXCR2) agonist or a C-X-C chemokine receptor type 4 (CXCR4) antagonist, in combination with an agent that decreases the level or activity of EXT-1, or heparin, in amounts effective to deplete hematopoietic stem cells from the subject's stem cell niche for subsequent engraftment of transplanted hematopoietic stem cells and/or progenitor cells in the absence of cytotoxic conditioning, wherein the subject is not administered G-CSF, wherein the subject is in need of a hematopoietic stem cell and/or progenitor cell transplant, and wherein the subject is a patient presenting with a hematological malignancy or with HIV, thereby conditioning the subject for engraftment of transplanted hematopoietic stem cells and/or progenitor cells in the absence of cytotoxic conditioning.

2. The method according to claim 1, wherein the CXCR2 agonist is selected from the group consisting of Gro-beta, Gro-betaΔ4 and analogs or derivatives thereof.

3. The method according to claim 1, wherein the CXCR4 antagonist is selected from the group consisting of Plerixafor and analogs or derivatives thereof.

4. The method according to claim 1, wherein the CXCR2 agonist is selected from the group consisting of Gro-beta, Gro-betaΔ4 and analogs or derivatives thereof; and wherein the CXCR4 antagonist is selected from the group consisting of Plerixafor and analogs or derivatives thereof.

5. The method according to claim 1, further comprising administering to the subject a cytokine selected from the group consisting of granulocyte-macrophage colony-stimulating factor (GM-CSF), interleukin-3 (IL-3), and glycosylated or pegylated forms thereof.

6. The method according to claim 1, wherein the hematological malignancy is selected from the group consisting of acute lymphoid leukemia, acute myeloid leukemia, chronic lymphoid leukemia, chronic myeloid leukemia, diffuse large B-cell non-Hodgkin's lymphoma, mantle cell lymphoma, lymphoblastic lymphoma, Burkitt's lymphoma, follicular B-cell non-Hodgkin's lymphoma, T-cell non-Hodgkin's lymphoma, lymphocyte predominant nodular Hodgkin's lymphoma, multiple myeloma, and juvenile myelomonocytic leukemia.

7. The method according to claim 1, wherein both a C-X-C chemokine receptor type 2 (CXCR2) agonist and a C-X-C chemokine receptor type 4 (CXCR4) antagonist are administered to the subject.

8. The method of claim 1, further comprising administering to the subject a transplant of hematopoietic stem cells and/or progenitor cells.

9. The method of claim 1, wherein the C-X-C chemokine receptor type 2 (CXCR2) agonist or the C-X-C chemokine receptor type 4 (CXCR4) antagonist is administered in combination with an agent that decreases the level or activity of EXT-1.

10. The method of claim 1, wherein the C-X-C chemokine receptor type 2 (CXCR2) agonist or the C-X-C chemokine receptor type 4 (CXCR4) antagonist is administered in combination with heparin.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial
<220> FEATURE:
<223> OTHER INFORMATION: PCR primer

<400> SEQUENCE: 1
tgccgagcta aattacacat tg    22

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
ccttgtggag ggatgtacag a    21

```
<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
tgcatcagtg acggtaaacc a                                            21

<210> SEQ ID NO 4
<211> LENGTH: 22
<212> TYPE: DNA
<213> ORGANISM: Artificial
<220> FEATURE:
<223> OTHER INFORMATION: PCR primer

<400> SEQUENCE: 4
cacagtttgg agtgttgagg at                                           22

<210> SEQ ID NO 5
<211> LENGTH: 22
<212> TYPE: DNA
<213> ORGANISM: Artificial
<220> FEATURE:
<223> OTHER INFORMATION: PCR primer

<400> SEQUENCE: 5
gcgctggcag tacaatgaca gt                                           22

<210> SEQ ID NO 6
<211> LENGTH: 23
<212> TYPE: DNA
<213> ORGANISM: Artificial
<220> FEATURE:
<223> OTHER INFORMATION: PCR primer

<400> SEQUENCE: 6
attttccatc acatgctcca gat                                          23

<210> SEQ ID NO 7
<211> LENGTH: 19
<212> TYPE: DNA
<213> ORGANISM: Artificial
<220> FEATURE:
<223> OTHER INFORMATION: PCR primer

<400> SEQUENCE: 7
ccctgaagac tcgggccta                                               19

<210> SEQ ID NO 8
<211> LENGTH: 23
<212> TYPE: DNA
<213> ORGANISM: Artificial
<220> FEATURE:
<223> OTHER INFORMATION: PCR primer

<400> SEQUENCE: 8
caattacaag cgaaatgaga gcc                                          23

<210> SEQ ID NO 9
<211> LENGTH: 20
<212> TYPE: DNA
<213> ORGANISM: Artificial
<220> FEATURE:
<223> OTHER INFORMATION: PCR primer
```

```
<400> SEQUENCE: 9 gccctttgt tttattttgg                                              20

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
tcttgccttt gtagatgctc                                             20

<210> SEQ ID NO 11
<211> LENGTH: 19
<212> TYPE: DNA
<213> ORGANISM: Artificial
<220> FEATURE:
<223> OTHER INFORMATION: PCR primer

<400> SEQUENCE: 11
cagcagtaca acggcgaac                                              19

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
gtcctcctga ttcgtgtggc                                             20
```